(12) United States Patent
Chappell et al.

(10) Patent No.: US 9,821,037 B1
(45) Date of Patent: Nov. 21, 2017

(54) COMPOUNDS AND METHOD OF USE AS ANTI-INFECTION COMPOUNDS AND THERAPEUTIC AGENTS TO REGULATE CHOLESTEROL METABOLISM

(71) Applicant: University of Kentucky Research Foundation, Lexington, KY (US)

(72) Inventors: Joe Chappell, Lexington, KY (US); Tom D. Niehaus, Lexington, KY (US); Kristin Linscott, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 312 days.

(21) Appl. No.: 14/257,598

(22) Filed: Apr. 21, 2014

Related U.S. Application Data

(60) Provisional application No. 61/814,067, filed on Apr. 19, 2013.

(51) Int. Cl.
| | | |
|---|---|---|
| *A61K 38/16* | (2006.01) | |
| *C07K 14/00* | (2006.01) | |
| *A61K 38/45* | (2006.01) | |
| *C12N 9/10* | (2006.01) | |

(52) U.S. Cl.
CPC ........... *A61K 38/45* (2013.01); *C12N 9/1085* (2013.01); *C12Y 205/01021* (2013.01)

(58) Field of Classification Search
CPC ................. A61K 38/45; C12N 9/1085; C12Y 205/01021
See application file for complete search history.

(56) References Cited

U.S. PATENT DOCUMENTS

2003/0114366 A1* 6/2003 Martin .................... A61K 38/17
424/489
2010/0151519 A1* 6/2010 Julien .................. C12N 9/1085
435/69.1

OTHER PUBLICATIONS

De Lucca et al, Fungicidal and binding properties of the natural peptides cecropin B and dermaseptin, Medical Mycology, 1998, 36, pp. 291-298.*
Jenssen et al, Peptide Antimicrobial Agents, Clinical Microbiology Reviews, 2006, 19, pp. 491-511.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BloL (2002) 324, 373-386.*
Water, from http://www.biology-online.org/dictionary/Water, pp. 1-3, accessed Apr. 24, 2014.*
Source of Sucrose Sugar, from http://www.livestrong.com/article/119325-sources-sucrose-sugar/, Jul. 18, 2015, pp. 1-3.*
Potato Dextrose Broth, from HiMedia Laboratories, Feb. 2015, pp. 1-2.*
Potato Dextrose Agar, from http://www.fda.gov/Food/FoodScienceResearch/LaboratoryMethods/ucm063519.htm, Jan. 2001, pp. 1-2.*

* cited by examiner

*Primary Examiner* — Julie Ha
*Assistant Examiner* — Li Ni Komatsu
(74) *Attorney, Agent, or Firm* — Stites & Harbison PLLC; Stephen Weyer; Mandy Wilson Decker

(57) ABSTRACT

A compound is provided which comprises at least a portion of an amino acid linker-domain from squalene synthase. In alternative forms, the compound can include the amino-acid linker-domain from various fungus, including *S. cerevisiae* or the compound can be the functional equivalent and/or mimics an amino acid linker-domain from squalene synthase. A pharmaceutical composition includes the compound and may further include a pharmaceutical carrier. A method is provided for treating or controlling cholesterol metabolism and ergosterol metabolism in non-fungal organisms. One method includes a therapeutic treatment in humans by administering a therapeutically effective amount of the compound or pharmaceutical composition, to a patient in need of treatment, therefrom.

3 Claims, 7 Drawing Sheets

| name | depiction | complement erg9 KO | squalene (μg/ml) | enzyme activity (% YSS) |
|---|---|---|---|---|
| k | empty vector control | | N.D. | N.D. |
| YSS | 1 — 444 | | 21.0 ± 1.5 | 100.0 ± 7.9 |
| YSStr | 1 — 420 | | 41.6 ± 4.3 | 77.0 ± 0.9 |
| BSS | 1 — 461 | | 81.3 ± 8.0 | 170.1 ± 1.4 |
| RSS | 1 — 416 | | 63.1 ± 2.8 | 120.6 ± 3.5 |
| TSS | 1 — 411 | | 62.5 ± 8.0 | 158.3 ± 4.0 |
| ASS | 1 — 410 | | 69.0 ± 7.9 | 151.0 ± 3.9 |

FIGURE 1

| name | depiction | complement erg9 KO | squalene (µg/ml) | enzyme activity (% YSS) |
|---|---|---|---|---|
| BSS-YSS | 1, 352, 444 (92AA) | | 54.6 ± 7.9 | 101.5 ± 9.9 |
| BSS-YSStr | 1, 420 (68AA) | | 70.5 ± 9.5 | 75.5 ± 6.7 |
| YSS-BSS | 1, 352, 461 (109AA) | | 71.7 ± 6.0 | 55.8 ± 6.7 |
| ASS-YSS | 1, 344, 436 (92AA) | | 54.5 ± 2.3 | 70.4 ± 1.7 |
| YSS-ASS | 1, 352, 418 (66AA) | | 50.2 ± 2.0 | 104.4 ± 2.2 |
| TSS-YSS | 1, 342, 434 (92AA) | | 43.9 ± 5.1 | 55.9 ± 2.5 |
| YSS-TSS | 1, 352, 421 (69AA) | | 59.2 ± 1.8 | 96.0 ± 2.9 |

FIGURE 2

| name | depiction | complement erg9 KO | squalene (μg/ml) | enzyme activity (% YSS) |
|---|---|---|---|---|
| Native YSS | 1  352 378 444 | | 21.0 ± 1.5 | 100.0 ± 7.9 |
| M(a) | KTKVDKNDPNASKLNIQISKIEQFME (SEQ ID NO: 25) | | 65.4 ± 3.1 | 160.5 ± 3.8 |
| M(b) | KSKLAVQDPNFLKTLNRLEAVQKLCR (SEQ ID NO: 26) | | 46.6 ± 9.7 | 152.7 ± 1.6 |
| M(c) | KSKLAVQDPNFLKLNIQISAVQKFME (SEQ ID NO: 27) | | 28.0 ± 1.3 | 156.1 ± 5.8 |
| M(d) | KSKLAVQDPNASKTLNRISKIEQFME (SEQ ID NO: 28) | | 50.7 ± 13.5 | 161.8 ± 5.3 |
| M(e) | KSKLAVQDPNASKTLNRLEAVQKFME (SEQ ID NO: 29) | | 69.1 ± 7.1 | 123.1 ± 6.0 |
| Native ASS | 1  344 371 410 | | 69.0 ± 7.9 | 151.0 ± 3.9 |
| M(f) | KSKLAVQDPNFLKTLNRLEAVQKLCR (SEQ ID NO: 30) | | 82.8 ± 10.3 | 137.4 ± 8.6 |
| M(g) | KTKVDKNDPNASKLNIQISKIEQFME (SEQ ID NO: 31) | | 47.9 ± 6.0 | 151.4 ± 4.0 |
| M(h) | KTKVDKNDPNASKTLNRLEKIEQLCR (SEQ ID NO: 32) | | 64.9 ± 8.9 | 166.1 ± 1.3 |
| M(i) | KTKVDKNDPNFLKLNIQLEAVQKLCR (SEQ ID NO: 33) | | 85.2 ± 5.6 | 170.8 ± 1.2 |
| M(j) | KTKVDKNDPNFLKLNIQISKIEQLCR (SEQ ID NO: 34) | | 41.7 ± 1.6 | 159.7 ± 5.8 |

FIGURE 5

```
                       SEQUENCE LISTING

<160> NUMBER OF SEQ ID NOS: 161

<210> SEQ ID NO 1
<211> LENGTH: 26
<212> TYPE: PRT
<213> ORGANISM: Saccharomyces cerevisiae

<400> SEQUENCE: 1

Lys Ser Lys Leu Ala Val Gln Asp Pro Asn Phe Leu Lys Leu Asn Ile
1               5                   10                  15

Gln Ile Ser Lys Ile Glu Gln Phe Met Glu
            20                  25

<210> SEQ ID NO 2
<211> LENGTH: 26
<212> TYPE: PRT
<213> ORGANISM: Schizosaccharomyces pombe

<400> SEQUENCE: 2

His Tyr Lys Asn Thr Pro Lys Asp Pro Asn Phe Leu Lys Ile Ser Ile
1               5                   10                  15

Glu Cys Gly Lys Ile Glu Gln Val Ser Glu
            20                  25

<210> SEQ ID NO 3
<211> LENGTH: 26
<212> TYPE: PRT
<213> ORGANISM: Yarrowia lipolytica

<400> SEQUENCE: 3

Tyr Lys Lys Ser Asp Pro Asn Asp Pro Asn Tyr Phe Arg Val Ser Val
1               5                   10                  15

Leu Cys Gly Lys Ile Glu Gln His Ala Ala
            20                  25

<210> SEQ ID NO 4
<211> LENGTH: 29
<212> TYPE: PRT
<213> ORGANISM: Botryococcus braunii

<400> SEQUENCE: 4

Glu Val Arg Cys Asn Thr Glu Thr Ser Glu Asp Pro Ser Val Thr Thr
1               5                   10                  15
```

Thr Leu Glu His Leu His Lys Ile Lys Ala Ala Cys Lys
            20                  25

<210> SEQ ID NO 5
<211> LENGTH: 26
<212> TYPE: PRT
<213> ORGANISM: Chlamydomonas reinhardtii

<400> SEQUENCE: 5

Glu Ala Lys Val Asp Pro Thr Asp Pro Ser Leu Pro Leu Thr Arg Gln
1               5                   10                  15

Arg Ile Ala Glu Ala Arg Lys Ala Cys Ala
            20                  25

<210> SEQ ID NO 6
<211> LENGTH: 26
<212> TYPE: PRT
<213> ORGANISM: Arabidopsis thaliana

<400> SEQUENCE: 6

Lys Thr Lys Val Asp Lys Asn Asp Pro Asn Ala Ser Lys Thr Leu Asn
1               5                   10                  15

Arg Leu Glu Ala Val Gln Lys Leu Cys Arg
            20                  25

<210> SEQ ID NO 7
<211> LENGTH: 26
<212> TYPE: PRT
<213> ORGANISM: Nicotiana benthamiana

<400> SEQUENCE: 7

Lys Ser Lys Val Asn Asn Asn Asp Pro Asn Ala Thr Lys Thr Leu Lys
1               5                   10                  15

Arg Leu Glu Val Ile Leu Lys Thr Cys Arg
            20                  25

<210> SEQ ID NO 8
<211> LENGTH: 26
<212> TYPE: PRT
<213> ORGANISM: Homo sapiens

<400> SEQUENCE: 8

Tyr His Arg Ile Pro Asp Ser Asn Pro Ser Ser Lys Thr Arg Gln
1               5                   10                  15

Ile Ile Ser Thr Ile Arg Thr Gln Asn Leu
            20                  25

<210> SEQ ID NO 9
<211> LENGTH: 26
<212> TYPE: PRT
<213> ORGANISM: Rattus norvegicus

<400> SEQUENCE: 9

Tyr His Arg Val Pro Asn Ser Asp Pro Ser Ala Ser Lys Ala Lys Gln
1               5                   10                  15

Leu Ile Ser Asn Ile Arg Thr Gln Ser Leu
            20                  25

<210> SEQ ID NO 10
<211> LENGTH: 26
<212> TYPE: PRT
<213> ORGANISM: Saccharomyces cerevisiae

<400> SEQUENCE: 10

Lys Ser Lys Leu Ala Val Gln Asp Pro Asn Phe Leu Lys Leu Asn Ile
1               5                   10                  15

Gln Ile Ser Lys Ile Glu Gln Phe Met Glu
            20                  25

<210> SEQ ID NO 11
<211> LENGTH: 26
<212> TYPE: PRT
<213> ORGANISM: Schizosaccharomyces pombe

<400> SEQUENCE: 11

His Tyr Lys Asn Thr Pro Lys Asp Pro Asn Phe Leu Lys Ile Ser Ile
1               5                   10                  15

Glu Cys Gly Lys Ile Glu Gln Val Ser Glu
            20                  25

<210> SEQ ID NO 12
<211> LENGTH: 26
<212> TYPE: PRT
<213> ORGANISM: Yarrowia lipolytica

<400> SEQUENCE: 12

Tyr Lys Lys Ser Asp Pro Asn Asp Pro Asn Tyr Phe Arg Val Ser Val
1               5                   10                  15

Leu Cys Gly Lys Ile Glu Gln His Ala Ala
            20                  25

<210> SEQ ID NO 13
<211> LENGTH: 67
<212> TYPE: PRT
<213> ORGANISM: Saccharomyces cerevisiae

<400> SEQUENCE: 13

Lys Ser Lys Leu Ala Val Gln Asp Pro Asn Phe Leu Lys Leu Asn Ile
1               5                   10                  15

Gln Ile Ser Lys Ile Glu Gln Phe Met Glu Glu Met Tyr Gln Asp Lys
            20                  25                  30

Leu Pro Pro Asn Val Lys Pro Asn Glu Thr Pro Ile Phe Leu Lys Val
        35                  40                  45

Lys Glu Arg Ser Arg Tyr Asp Asp Glu Leu Val Pro Thr Gln Gln Glu
    50                  55                  60

Glu Glu Tyr
65

<210> SEQ ID NO 14
<211> LENGTH: 67
<212> TYPE: PRT
<213> ORGANISM: Schizosaccharomyces pombe

<400> SEQUENCE: 14

His Tyr Lys Asn Thr Pro Lys Asp Pro Asn Phe Leu Lys Ile Ser Ile
1               5                   10                  15

Glu Cys Gly Lys Ile Glu Gln Val Ser Glu Ser Leu Phe Pro Arg Arg
            20                  25                  30

Phe Arg Glu Met Tyr Glu Lys Ala Tyr Val Ser Lys Leu Ser Glu Gln
        35                  40                  45

Lys Lys Gly Asn Gly Thr Gln Lys Ala Ile Leu Asn Asp Glu Gln Lys
    50                  55                  60

Glu Leu Tyr
65

<210> SEQ ID NO 15
<211> LENGTH: 67
<212> TYPE: PRT
<213> ORGANISM: Yarrowia lipolytica

<400> SEQUENCE: 15

Tyr Lys Lys Ser Asp Pro Asn Asp Pro Asn Tyr Phe Arg Val Ser Val
1               5                   10                  15

Leu Cys Gly Lys Ile Glu Gln His Ala Ala Leu Ile Lys Arg Gln Arg
            20                  25                  30

Gly Pro Pro Ala Lys Thr Ile Ala Gln Leu Glu Gly Glu Arg Lys Glu
        35                  40                  45

Met Ala Leu Ser Leu Ile Val Cys Leu Ala Val Ile Phe Ser Met Ser
    50                  55                  60

Gly Leu Met
65

<210> SEQ ID NO 16
<211> LENGTH: 70
<212> TYPE: PRT
<213> ORGANISM: Botryococcus braunii

<400> SEQUENCE: 16

Glu Val Arg Cys Asn Thr Glu Thr Ser Glu Asp Pro Ser Val Thr Thr
1               5                   10                  15

Thr Leu Glu His Leu His Lys Ile Lys Ala Ala Cys Lys Ala Gly Leu
            20                  25                  30

Ala Arg Thr Lys Asp Asp Thr Phe Asp Glu Leu Arg Ser Arg Leu Leu
        35                  40                  45

Ala Leu Thr Gly Gly Ser Phe Tyr Leu Ala Trp Thr Tyr Asn Phe Leu
    50                  55                  60

Asp Leu Arg Gly Pro Gly
65                  70

<210> SEQ ID NO 17
<211> LENGTH: 34
<212> TYPE: PRT
<213> ORGANISM: Chlamydomonas reinhardtii

<400> SEQUENCE: 17

Glu Ala Lys Val Asp Pro Thr Asp Pro Ser Leu Pro Leu Thr Arg Gln
1               5                   10                  15

Arg Ile Ala Glu Ala Arg Lys Ala Cys Ala Ala Lys Leu Thr Glu Val
            20                  25                  30

Ser Val

<210> SEQ ID NO 18
<211> LENGTH: 65
<212> TYPE: PRT
<213> ORGANISM: Arabidopsis thaliana

<400> SEQUENCE: 18

Lys Thr Lys Val Asp Lys Asn Asp Pro Asn Ala Ser Lys Thr Leu Asn
1               5                   10                  15

Arg Leu Glu Ala Val Gln Lys Leu Cys Arg Asp Ala Gly Val Leu Gln
            20                  25                  30

Asn Arg Lys Ser Tyr Val Asn Asp Lys Gly Gln Pro Asn Ser Val Phe
            35                  40                  45

Ile Ile Met Val Val Ile Leu Leu Ala Ile Val Phe Ala Tyr Leu Arg
 50                  55                  60

Ala
 65

<210> SEQ ID NO 19
<211> LENGTH: 66
<212> TYPE: PRT
<213> ORGANISM: Nicotiana benthamiana

<400> SEQUENCE: 19

Lys Ser Lys Val Asn Asn Asp Pro Asn Ala Thr Lys Thr Leu Lys
 1               5                  10                  15

Arg Leu Glu Val Ile Leu Lys Thr Cys Arg Asp Ser Gly Thr Leu Asn
            20                  25                  30

Lys Arg Lys Ser Tyr Ile Ile Arg Ser Glu Pro Asn Tyr Ser Pro Val
            35                  40                  45

Leu Ile Val Val Ile Phe Ile Ile Leu Ala Ile Leu Ala Gln Leu
 50                  55                  60

Ser Gly
 65

<210> SEQ ID NO 20
<211> LENGTH: 67
<212> TYPE: PRT
<213> ORGANISM: Homo sapiens

<400> SEQUENCE: 20

Tyr His Arg Ile Pro Asp Ser Asn Pro Ser Ser Lys Thr Arg Gln
 1               5                  10                  15

Ile Ile Ser Thr Ile Arg Thr Gln Asn Leu Pro Asn Cys Gln Leu Ile
            20                  25                  30

Ser Arg Ser His Tyr Ser Pro Ile Tyr Leu Ser Phe Val Met Leu Leu
            35                  40                  45

Ala Ala Leu Ser Trp Gln Tyr Leu Thr Thr Leu Ser Gln Val Thr Glu
 50                  55                  60

Asp Tyr Val
 65

<210> SEQ ID NO 21
<211> LENGTH: 67
<212> TYPE: PRT
<213> ORGANISM: Rattus norvegicus

<400> SEQUENCE: 21

Tyr His Arg Val Pro Asn Ser Asp Pro Ser Ala Ser Lys Ala Lys Gln
 1               5                  10                  15

Leu Ile Ser Asn Ile Arg Thr Gln Ser Leu Pro Asn Cys Gln Leu Ile
            20                  25                  30

Ser Arg Ser His Tyr Ser Pro Ile Tyr Leu Ser Phe Ile Met Leu Leu
            35                  40                  45

Ala Ala Leu Ser Trp Gln Tyr Leu Ser Thr Leu Ser Gln Val Thr Glu
 50                  55                  60

Asp Tyr Val
 65

<210> SEQ ID NO 22
<211> LENGTH: 67
<212> TYPE: PRT
<213> ORGANISM: Saccharomyces cerevisiae

<400> SEQUENCE: 22

Lys Ser Lys Leu Ala Val Gln Asp Pro Asn Phe Leu Lys Leu Asn Ile
1               5                   10                  15

Gln Ile Ser Lys Ile Glu Gln Phe Met Glu Glu Met Tyr Gln Asp Lys
            20                  25                  30

Leu Pro Pro Asn Val Lys Pro Asn Glu Thr Pro Ile Phe Leu Lys Val
        35                  40                  45

Lys Glu Arg Ser Arg Tyr Asp Asp Glu Leu Val Pro Thr Gln Gln Glu
    50                  55                  60

Glu Glu Tyr
65

<210> SEQ ID NO 23
<211> LENGTH: 67
<212> TYPE: PRT
<213> ORGANISM: Schizosaccharomyces pombe

<400> SEQUENCE: 23

His Tyr Lys Asn Thr Pro Lys Asp Pro Asn Phe Leu Lys Ile Ser Ile
1               5                   10                  15

Glu Cys Gly Lys Ile Glu Gln Val Ser Glu Ser Leu Phe Pro Arg Arg
            20                  25                  30

Phe Arg Glu Met Tyr Glu Lys Ala Tyr Val Ser Lys Leu Ser Glu Gln
        35                  40                  45

Lys Lys Gly Asn Gly Thr Gln Lys Ala Ile Leu Asn Asp Glu Gln Lys
    50                  55                  60

Glu Leu Tyr
65

<210> SEQ ID NO 24
<211> LENGTH: 67
<212> TYPE: PRT
<213> ORGANISM: Yarrowia lipolytica

<400> SEQUENCE: 24

Tyr Lys Lys Ser Asp Pro Asn Asp Pro Asn Tyr Phe Arg Val Ser Val
1               5                   10                  15

Leu Cys Gly Lys Ile Glu Gln His Ala Ala Leu Ile Lys Arg Gln Arg
            20                  25                  30

Gly Pro Pro Ala Lys Thr Ile Ala Gln Leu Glu Gly Glu Arg Lys Glu
        35                  40                  45

Met Ala Leu Ser Leu Ile Val Cys Leu Ala Val Ile Phe Ser Met Ser
    50                  55                  60

Gly Leu Met
65

<210> SEQ ID NO 25
<211> LENGTH: 26
<212> TYPE: PRT
<213> ORGANISM: Saccharomyces cerevisiae

<400> SEQUENCE: 25

Lys Thr Lys Val Asp Lys Asn Asp Pro Asn Ala Ser Lys Leu Asn Ile
1               5                   10                  15

Gln Ile Ser Lys Ile Glu Gln Phe Met Glu
            20                  25

<210> SEQ ID NO 26
<211> LENGTH: 26
<212> TYPE: PRT
<213> ORGANISM: Saccharomyces cerevisiae

<400> SEQUENCE: 26

Lys Ser Lys Leu Ala Val Gln Asp Pro Asn Phe Leu Lys Thr Leu Asn
1               5                   10                  15

Arg Leu Glu Ala Val Gln Lys Leu Cys Arg
            20                  25

<210> SEQ ID NO 27
<211> LENGTH: 26
<212> TYPE: PRT
<213> ORGANISM: Saccharomyces cerevisiae

<400> SEQUENCE: 27

Lys Ser Lys Leu Ala Val Gln Asp Pro Asn Phe Leu Lys Leu Asn Ile
1               5                   10                  15

Gln Ile Ser Ala Val Gln Lys Phe Met Glu
            20                  25

<210> SEQ ID NO 28
<211> LENGTH: 26
<212> TYPE: PRT
<213> ORGANISM: Saccharomyces cerevisiae

<400> SEQUENCE: 28

Lys Ser Lys Leu Ala Val Gln Asp Pro Asn Ala Ser Lys Thr Leu Asn
1               5                   10                  15

Arg Ile Ser Lys Ile Glu Gln Phe Met Glu
            20                  25

<210> SEQ ID NO 29
<211> LENGTH: 26
<212> TYPE: PRT
<213> ORGANISM: Saccharomyces cerevisiae

<400> SEQUENCE: 29

Lys Ser Lys Leu Ala Val Gln Asp Pro Asn Ala Ser Lys Thr Leu Asn
1               5                   10                  15

Arg Leu Glu Ala Val Gln Lys Phe Met Glu
            20                  25

<210> SEQ ID NO 30
<211> LENGTH: 26
<212> TYPE: PRT
<213> ORGANISM: Arabidopsis thaliana

<400> SEQUENCE: 30

Lys Ser Lys Leu Ala Val Gln Asp Pro Asn Phe Leu Lys Thr Leu Asn
1               5                   10                  15

Arg Leu Glu Ala Val Gln Lys Leu Cys Arg
            20                  25

<210> SEQ ID NO 31
<211> LENGTH: 26
<212> TYPE: PRT
<213> ORGANISM: Arabidopsis thaliana -continued

<400> SEQUENCE: 31

Lys Thr Lys Val Asp Lys Asn Asp Pro Asn Ala Ser Lys Leu Asn Ile
1               5                   10                  15
Gln Ile Ser Lys Ile Glu Gln Phe Met Glu
            20                  25

<210> SEQ ID NO 32
<211> LENGTH: 26
<212> TYPE: PRT
<213> ORGANISM: Arabidopsis thaliana

<400> SEQUENCE: 32

Lys Thr Lys Val Asp Lys Asn Asp Pro Asn Ala Ser Lys Thr Leu Asn
1               5                   10                  15
Arg Leu Glu Lys Ile Glu Gln Leu Cys Arg
            20                  25

<210> SEQ ID NO 33
<211> LENGTH: 26
<212> TYPE: PRT
<213> ORGANISM: Arabidopsis thaliana

<400> SEQUENCE: 33

Lys Thr Lys Val Asp Lys Asn Asp Pro Asn Phe Leu Lys Leu Asn Ile
1               5                   10                  15
Gln Leu Glu Ala Val Gln Lys Leu Cys Arg
            20                  25

<210> SEQ ID NO 34
<211> LENGTH: 26
<212> TYPE: PRT
<213> ORGANISM: Arabidopsis thaliana

<400> SEQUENCE: 34

Lys Thr Lys Val Asp Lys Asn Asp Pro Asn Phe Leu Lys Leu Asn Ile
1               5                   10                  15
Gln Ile Ser Lys Ile Glu Gln Leu Cys Arg
            20                  25

<210> SEQ ID NO 35
<211> LENGTH: 4
<212> TYPE: PRT
<213> ORGANISM: Saccharomyces cerevisiae

<400> SEQUENCE: 35

Lys Ile Glu Gln
1

<210> SEQ ID NO 36
<211> LENGTH: 7
<212> TYPE: PRT
<213> ORGANISM: Saccharomyces cerevisiae

<400> SEQUENCE: 36

Phe Leu Lys Leu Asn Ile Gln
1               5

<210> SEQ ID NO 37
<211> LENGTH: 37
<212> TYPE: DNA
<213> ORGANISM: Artificial Sequence
<220> FEATURE:

```
<223> OTHER INFORMATION: Squalene synthases from S. cerevisiae cloned
      into the Yep352 vector
<220> FEATURE:
<221> NAME/KEY: misc_binding
<222> LOCATION: (2)..(9)

<400> SEQUENCE: 37
aggcgcgcca aaacaatggg aaagctatta caatggc                            37

<210> SEQ ID NO 38
<211> LENGTH: 37
<212> TYPE: DNA
<213> ORGANISM: Artificial Sequence
<220> FEATURE:
<223> OTHER INFORMATION: Squalene synthases from S. cerevisiae cloned
      into the Yep352 vector
<220> FEATURE:
<221> NAME/KEY: misc_binding
<222> LOCATION: (4)..(9)

<400> SEQUENCE: 38
cgcggatcca aaacaatggg aaagctatta caatggc                            37

<210> SEQ ID NO 39
<211> LENGTH: 32
<212> TYPE: DNA
<213> ORGANISM: Artificial Sequence
<220> FEATURE:
<223> OTHER INFORMATION: Squalene synthases from S. cerevisiae cloned
      into the Yep352 vector
<220> FEATURE:
<221> NAME/KEY: misc_binding
<222> LOCATION: (3)..(8)

<400> SEQUENCE: 39
gctctagatc acgctctgtg taaagtgtat at                                 32

<210> SEQ ID NO 40
<211> LENGTH: 35
<212> TYPE: DNA
<213> ORGANISM: Artificial Sequence
<220> FEATURE:
<223> OTHER INFORMATION: Squalene synthases from S. cerevisiae cloned
      into the Yep352 vector
<220> FEATURE:
<221> NAME/KEY: misc_binding
<222> LOCATION: (9)..(16)

<400> SEQUENCE: 40
ataagaatgc ggccgctcac gctctgtgta aagtg                              35

<210> SEQ ID NO 41
<211> LENGTH: 26
<212> TYPE: DNA
<213> ORGANISM: Artificial Sequence
<220> FEATURE:
<223> OTHER INFORMATION: Squalene synthases from S. cerevisiae cloned
      into the Yep352 vector
<220> FEATURE:
<221> NAME/KEY: misc_binding
<222> LOCATION: (3)..(8)

<400> SEQUENCE: 41
gctctagatc acttgtactc ttcttc                                        26

<210> SEQ ID NO 42
<211> LENGTH: 27
<212> TYPE: DNA
<213> ORGANISM: Artificial Sequence
```

<220> FEATURE:
<223> OTHER INFORMATION: Squalene synthases from S. cerevisiae cloned
     into the Yep352 vector
<220> FEATURE:
<221> NAME/KEY: misc_binding
<222> LOCATION: (4)..(9)

<400> SEQUENCE: 42
gggctcgagt cacttgtact cttcttc                                           27

<210> SEQ ID NO 43
<211> LENGTH: 37
<212> TYPE: DNA
<213> ORGANISM: Artificial Sequence
<220> FEATURE:
<223> OTHER INFORMATION: Squalene synthases from S. cerevisiae cloned
     into the Yep352 vector
<220> FEATURE:
<221> NAME/KEY: misc_binding
<222> LOCATION: (9)..(16)

<400> SEQUENCE: 43
ataagaatgc ggccgctcac ttgtactctt cttcttg                                37

<210> SEQ ID NO 44
<211> LENGTH: 40
<212> TYPE: DNA
<213> ORGANISM: Artificial Sequence
<220> FEATURE:
<223> OTHER INFORMATION: Squalene synthases from B. braunii cloned into
     the Yep352 vector
<220> FEATURE:
<221> NAME/KEY: misc_binding
<222> LOCATION: (4)..(9)

<400> SEQUENCE: 44
ccggaattca aaacaatggg gatgcttcgc tggggagtgg                              40

<210> SEQ ID NO 45
<211> LENGTH: 35
<212> TYPE: DNA
<213> ORGANISM: Artificial Sequence
<220> FEATURE:
<223> OTHER INFORMATION: Squalene synthases from B. braunii cloned into
     the Yep352 vector
<220> FEATURE:
<221> NAME/KEY: misc_binding
<222> LOCATION: (6)..(11)

<400> SEQUENCE: 45
atcccaagct tttaggcgct gagtgtgggt ctagg                                  35

<210> SEQ ID NO 46
<211> LENGTH: 40
<212> TYPE: DNA
<213> ORGANISM: Artificial Sequence
<220> FEATURE:
<223> OTHER INFORMATION: Squalene synthases from B. braunii cloned into
     the Yep352 vector
<220> FEATURE:
<221> NAME/KEY: misc_binding
<222> LOCATION: (9)..(16)

<400> SEQUENCE: 46
ataagaatgc ggccgcttag gcgctgagtg tgggtctagg                              40

<210> SEQ ID NO 47
<211> LENGTH: 38
<212> TYPE: DNA

<213> ORGANISM: Artificial Sequence
<220> FEATURE:
<223> OTHER INFORMATION: Squalene synthases from R. norvegicus cloned
      into the Yep352 vector
<220> FEATURE:
<221> NAME/KEY: misc_binding
<222> LOCATION: (2)..(7)

<400> SEQUENCE: 47
ggaattcaaa acaatggagt tcgtgaagtg tctaggcc                               38

<210> SEQ ID NO 48
<211> LENGTH: 30
<212> TYPE: DNA
<213> ORGANISM: Artificial Sequence
<220> FEATURE:
<223> OTHER INFORMATION: Squalene synthases from R. norvegicus cloned
      into the Yep352 vector
<220> FEATURE:
<221> NAME/KEY: misc_binding
<222> LOCATION: (4)..(9)

<400> SEQUENCE: 48
cgcggatcca tggaccggaa ctcgctcagc                                        30

<210> SEQ ID NO 49
<211> LENGTH: 40
<212> TYPE: DNA
<213> ORGANISM: Artificial Sequence
<220> FEATURE:
<223> OTHER INFORMATION: Squalene synthases from R. norvegicus cloned
      into the Yep352 vector
<220> FEATURE:
<221> NAME/KEY: misc_binding
<222> LOCATION: (9)..(16)

<400> SEQUENCE: 49
ataagaatgc ggccgctcag tgttctctct ggacatagtc                             40

<210> SEQ ID NO 50
<211> LENGTH: 34
<212> TYPE: DNA
<213> ORGANISM: Artificial Sequence
<220> FEATURE:
<223> OTHER INFORMATION: Squalene synthases from R. norvegicus cloned
      into the Yep352 vector
<220> FEATURE:
<221> NAME/KEY: misc_binding
<222> LOCATION: (4)..(9)

<400> SEQUENCE: 50
ccgctcgagt cagctctgcg tcctgatgtt ggag                                   34

<210> SEQ ID NO 51
<211> LENGTH: 29
<212> TYPE: DNA
<213> ORGANISM: Artificial Sequence
<220> FEATURE:
<223> OTHER INFORMATION: Squalene synthases from N. benthamiana cloned
      into the Yep352 vector
<220> FEATURE:
<221> NAME/KEY: misc_binding
<222> LOCATION: (2)..(7)

<400> SEQUENCE: 51
ggaattcatg gggagtttga gggctattc                                         29

<210> SEQ ID NO 52
<211> LENGTH: 30

-continued

```
<212> TYPE: DNA
<213> ORGANISM: Artificial Sequence
<220> FEATURE:
<223> OTHER INFORMATION: Squalene synthases from N. benthamiana cloned
      into the Yep352 vector
<220> FEATURE:
<221> NAME/KEY: misc_binding
<222> LOCATION: (3)..(8)

<400> SEQUENCE: 52
gctctagact aagatcggtt tccggatagc                                    30

<210> SEQ ID NO 53
<211> LENGTH: 38
<212> TYPE: DNA
<213> ORGANISM: Artificial Sequence
<220> FEATURE:
<223> OTHER INFORMATION: Squalene synthases from N. benthamiana cloned
      into the Yep352 vector
<220> FEATURE:
<221> NAME/KEY: misc_binding
<222> LOCATION: (9)..(16)

<400> SEQUENCE: 53
ataagaatgc ggccgcctaa gatcggtttc cggatagc                           38

<210> SEQ ID NO 54
<211> LENGTH: 39
<212> TYPE: DNA
<213> ORGANISM: Artificial Sequence
<220> FEATURE:
<223> OTHER INFORMATION: Squalene synthases from A. thaliana cloned into
      the Yep352 vector
<220> FEATURE:
<221> NAME/KEY: misc_binding
<222> LOCATION: (4)..(9)

<400> SEQUENCE: 54
ccggaattca aaacaatggg gagcttgggg acgatgctg                          39

<210> SEQ ID NO 55
<211> LENGTH: 29
<212> TYPE: DNA
<213> ORGANISM: Artificial Sequence
<220> FEATURE:
<223> OTHER INFORMATION: Squalene synthases from A. thaliana cloned into
      the Yep352 vector
<220> FEATURE:
<221> NAME/KEY: misc_binding
<222> LOCATION: (2)..(7)

<400> SEQUENCE: 55
gctctagatc agtttgctct gagatatgc                                     29

<210> SEQ ID NO 56
<211> LENGTH: 41
<212> TYPE: DNA
<213> ORGANISM: Artificial Sequence
<220> FEATURE:
<223> OTHER INFORMATION: Squalene synthases from A. thaliana cloned into
      the Yep352 vector
<220> FEATURE:
<221> NAME/KEY: misc_binding
<222> LOCATION: (9)..(16)

<400> SEQUENCE: 56
ataagaatgc ggccgctcag tttgctctga gatatgcaaa g                       41

<210> SEQ ID NO 57
```

```
<211> LENGTH: 27
<212> TYPE: DNA
<213> ORGANISM: Artificial Sequence
<220> FEATURE:
<223> OTHER INFORMATION: Reverse primer is designed to pair with the
      Squalene synthases B. braunii EcoRI
<220> FEATURE:
<221> NAME/KEY: mutation
<222> LOCATION: (6)..(11)

<400> SEQUENCE: 57
atcccaagct tctctgctaa tttgagg                                          27

<210> SEQ ID NO 58
<211> LENGTH: 29
<212> TYPE: DNA
<213> ORGANISM: Artificial Sequence
<220> FEATURE:
<223> OTHER INFORMATION: Primer is designed to pair with the Squalene
      synthases S. cerevisiae
<220> FEATURE:
<221> NAME/KEY: misc_binding
<222> LOCATION: (5)..(10)

<400> SEQUENCE: 58
atccaagctt aaatctaaat tggctgtgc                                        29

<210> SEQ ID NO 59
<211> LENGTH: 50
<212> TYPE: DNA
<213> ORGANISM: Artificial Sequence
<220> FEATURE:
<223> OTHER INFORMATION: Primer is designed to pair with primer squalene
      synthases B. braunii EcoRI to amplify a fragment of the BSS-YSS
      construct with NgoMIV and NotI restriction sites
<220> FEATURE:
<221> NAME/KEY: misc_binding
<222> LOCATION: (10)..(17)
<220> FEATURE:
<221> NAME/KEY: misc_binding
<222> LOCATION: (22)..(27)

<400> SEQUENCE: 59
ataaagaatg cggccgcgaa tgccggcttc cataaactgt tcgatcttgg                 50

<210> SEQ ID NO 60
<211> LENGTH: 39
<212> TYPE: DNA
<213> ORGANISM: Artificial Sequence
<220> FEATURE:
<223> OTHER INFORMATION: Primer is designed to pair with primer squalene
      synthases B. braunii NotI Rev
<220> FEATURE:
<221> NAME/KEY: mutation
<222> LOCATION: (10)..(15)

<400> SEQUENCE: 60
gcaaagaatg ccggcctggc acgcacaaaa gatgacacc                             39

<210> SEQ ID NO 61
<211> LENGTH: 49
<212> TYPE: DNA
<213> ORGANISM: Artificial Sequence
<220> FEATURE:
<223> OTHER INFORMATION: Construction of chimeric squalene synthase
      primer sequence of S. cerevisiae and B. braunii
<220> FEATURE:
<221> NAME/KEY: misc_binding
<222> LOCATION: (1)..(49)

<400> SEQUENCE: 61
```
cttacgtgat atcgaagtca gatgcaacac cgagaccagc gaggatccc           49

<210> SEQ ID NO 62
<211> LENGTH: 51
<212> TYPE: DNA
<213> ORGANISM: Artificial Sequence
<220> FEATURE:
<223> OTHER INFORMATION: Construction of chimeric squalene synthase
      primer sequence of S. cerevisiae and B. braunii
<220> FEATURE:
<221> NAME/KEY: misc_binding
<222> LOCATION: (1)..(51)

<400> SEQUENCE: 62
gcatctgact tcgatatcac gtaagtaata gtcaaaaatc tcgacacagc c         51

<210> SEQ ID NO 63
<211> LENGTH: 48
<212> TYPE: DNA
<213> ORGANISM: Artificial Sequence
<220> FEATURE:
<223> OTHER INFORMATION: Construction of chimeric squalene synthase
      primer sequence of S. cerevisiae and A. thaliana
<220> FEATURE:
<221> NAME/KEY: misc_binding
<222> LOCATION: (1)..(48)

<400> SEQUENCE: 63
cttacgtgat atcaagacaa aggttgacaa gaacgatcca aatgccag             48

<210> SEQ ID NO 64
<211> LENGTH: 48
<212> TYPE: DNA
<213> ORGANISM: Artificial Sequence
<220> FEATURE:
<223> OTHER INFORMATION: Construction of chimeric squalene synthase
      primer sequence of S. cerevisiae and A. thaliana
<220> FEATURE:
<221> NAME/KEY: misc_binding
<222> LOCATION: (1)..(48)

<400> SEQUENCE: 64
caacctttgt cttgatatca cgtaagtaat agtcaaaaat ctcgacac             48

<210> SEQ ID NO 65
<211> LENGTH: 47
<212> TYPE: DNA
<213> ORGANISM: Artificial Sequence
<220> FEATURE:
<223> OTHER INFORMATION: Construction of chimeric squalene synthase
      primer sequence of A. thaliana and S. cerevisiae
<220> FEATURE:
<221> NAME/KEY: misc_binding
<222> LOCATION: (1)..(47)

<400> SEQUENCE: 65
cctgcatgct gaaatctaaa ttggctgtgc aagatccaaa tttctta              47

<210> SEQ ID NO 66
<211> LENGTH: 48
<212> TYPE: DNA
<213> ORGANISM: Artificial Sequence
<220> FEATURE:
<223> OTHER INFORMATION: Construction of chimeric squalene synthase
      primer sequence of A. thaliana and S. cerevisiae
<220> FEATURE:
<221> NAME/KEY: misc_binding
<222> LOCATION: (1)..(48)

<400> SEQUENCE: 66
gccaatttag atttcagcat gcaggaaaaa tcatagaaag caccatag    48

<210> SEQ ID NO 67
<211> LENGTH: 48
<212> TYPE: DNA
<213> ORGANISM: Artificial Sequence
<220> FEATURE:
<223> OTHER INFORMATION: Construction of chimeric squalene synthase
      primer sequence of S. cerevisiae and N. benthamiana
<220> FEATURE:
<221> NAME/KEY: misc_binding
<222> LOCATION: (1)..(48)

<400> SEQUENCE: 67
cttacgtgat atcaaatcca aggttaataa taatgatcca aatgcaac    48

<210> SEQ ID NO 68
<211> LENGTH: 49
<212> TYPE: DNA
<213> ORGANISM: Artificial Sequence
<220> FEATURE:
<223> OTHER INFORMATION: Construction of chimeric squalene synthase
      primer sequence of S. cerevisiae and N. benthamiana
<220> FEATURE:
<221> NAME/KEY: misc_binding
<222> LOCATION: (1)..(49)

<400> SEQUENCE: 68
ttaaccttgg atttgatatc acgtaagtaa tagtcaaaaa tctcgacac    49

<210> SEQ ID NO 69
<211> LENGTH: 53
<212> TYPE: DNA
<213> ORGANISM: Artificial Sequence
<220> FEATURE:
<223> OTHER INFORMATION: Construction of chimeric squalene synthase
      primer sequence of N. benthamiana and S. cerevisiae
<220> FEATURE:
<221> NAME/KEY: misc_binding
<222> LOCATION: (1)..(53)

<400> SEQUENCE: 69
gacttttctt gtatgctgaa atctaaattg gctgtgcaag atccaaattt ctt    53

<210> SEQ ID NO 70
<211> LENGTH: 53
<212> TYPE: DNA
<213> ORGANISM: Artificial Sequence
<220> FEATURE:
<223> OTHER INFORMATION: Construction of chimeric squalene synthase
      primer sequence of N. benthamiana and S. cerevisiae
<220> FEATURE:
<221> NAME/KEY: misc_binding
<222> LOCATION: (1)..(53)

<400> SEQUENCE: 70
gccaatttag atttcagcat acaagaaaag tcaaaaaaag caccatatac atc    53

<210> SEQ ID NO 71
<211> LENGTH: 54
<212> TYPE: DNA
<213> ORGANISM: Artificial Sequence
<220> FEATURE:
<223> OTHER INFORMATION: Construction of chimeric squalene synthase
      primer sequence of S. cerevisiae, B. braunii and S. cerevisiae
<220> FEATURE:
<221> NAME/KEY: misc_binding
<222> LOCATION: (1)..(54)

```
<400> SEQUENCE: 71
caaagctgcc tgcaaggaaa tgtaccagga taaattacct cctaacgtga agcc            54

<210> SEQ ID NO 72
<211> LENGTH: 51
<212> TYPE: DNA
<213> ORGANISM: Artificial Sequence
<220> FEATURE:
<223> OTHER INFORMATION: Construction of chimeric squalene synthase
      primer sequence of S. cerevisiae, B. braunii and S. cerevisiae
<220> FEATURE:
<221> NAME/KEY: misc_binding
<222> LOCATION: (1)..(51)

<400> SEQUENCE: 72
cctggtacat ttccttgcag gcagctttga tcttatgcag gtgttccaga g              51

<210> SEQ ID NO 73
<211> LENGTH: 60
<212> TYPE: DNA
<213> ORGANISM: Artificial Sequence
<220> FEATURE:
<223> OTHER INFORMATION: Construction of chimeric squalene synthase
      primer sequence of S. cerevisiae, A. thaliana and S. cerevisiae
<220> FEATURE:
<221> NAME/KEY: misc_binding
<222> LOCATION: (1)..(60)

<400> SEQUENCE: 73
aagacaaagg ttgacaagaa cgatccaaat gccagtaaga cactaaaccg acttgaagcc     60

<210> SEQ ID NO 74
<211> LENGTH: 60
<212> TYPE: DNA
<213> ORGANISM: Artificial Sequence
<220> FEATURE:
<223> OTHER INFORMATION: Construction of chimeric squalene synthase
      primer sequence of S. cerevisiae, A. thaliana and S. cerevisiae
<220> FEATURE:
<221> NAME/KEY: misc_binding
<222> LOCATION: (1)..(60)

<400> SEQUENCE: 74
tctgcagagt ttctgaacgg cttcaagtcg gtttagtgtc ttactggcat ttggatcgtt     60

<210> SEQ ID NO 75
<211> LENGTH: 60
<212> TYPE: DNA
<213> ORGANISM: Artificial Sequence
<220> FEATURE:
<223> OTHER INFORMATION: Construction of chimeric squalene synthase
      primer sequence of A. thaliana, S. cerevisiae and A. thaliana
<220> FEATURE:
<221> NAME/KEY: misc_binding
<222> LOCATION: (1)..(60)

<400> SEQUENCE: 75
aaatctaaat tggctgtgca agatccaaat ttcttaaaat tgaacattca aatctccaag     60

<210> SEQ ID NO 76
<211> LENGTH: 60
<212> TYPE: DNA
<213> ORGANISM: Artificial Sequence
<220> FEATURE:
<223> OTHER INFORMATION: Construction of chimeric squalene synthase
      primer sequence of A. thaliana, S. cerevisiae and A. thaliana
<220> FEATURE:
<221> NAME/KEY: misc_binding
```

<222> LOCATION: (1)..(60)

<400> SEQUENCE: 76
ttccataaac tgttcgatct tggagatttg aatgttcaat tttaagaaat ttggatcttg    60

<210> SEQ ID NO 77
<211> LENGTH: 48
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:
<221> NAME/KEY: misc_binding
<222> LOCATION: (1)..(48)

<400> SEQUENCE: 77
ctccgccgtt caaaagttta tggaagaaat gtaccaggat aaattacc                 48

<210> SEQ ID NO 78
<211> LENGTH: 44
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:
<221> NAME/KEY: misc_binding
<222> LOCATION: (1)..(44)

<400> SEQUENCE: 78
ccataaactt ttgaacggcg gagatttgaa tgttcaattt taag                     44

<210> SEQ ID NO 79
<211> LENGTH: 49
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:
<221> NAME/KEY: misc_binding
<222> LOCATION: (1)..(49)

<400> SEQUENCE: 79
aatgccagta agacactaaa ccgtatctcc aagatcgaac agtttatgg                49

<210> SEQ ID NO 80
<211> LENGTH: 50
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:
<221> NAME/KEY: misc_binding
<222> LOCATION: (1)..(50)

<400> SEQUENCE: 80
gatacggttt agtgtcttac tggcatttgg atcttgcaca gccaatttag               50

<210> SEQ ID NO 81
<211> LENGTH: 60
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:

<221> NAME/KEY: misc_binding
<222> LOCATION: (1)..(60)

<400> SEQUENCE: 81
gccagtaaga cactaaaccg tcttgaagcc gttcagaagt ttatggaaga aatgtaccag    60

<210> SEQ ID NO 82
<211> LENGTH: 58
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:
<221> NAME/KEY: misc_binding
<222> LOCATION: (1)..(58)

<400> SEQUENCE: 82
cttctgaacg gcttcaagac ggtttagtgt cttactggca tttggatctt gcacagcc    58

<210> SEQ ID NO 83
<211> LENGTH: 60
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:
<221> NAME/KEY: misc_binding
<222> LOCATION: (1)..(60)

<400> SEQUENCE: 83
aagacaaagg ttgacaagaa cgatccaaat gccagtaagt tgaacattca aatctccaag    60

<210> SEQ ID NO 84
<211> LENGTH: 60
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:
<221> NAME/KEY: misc_binding
<222> LOCATION: (1)..(60)

<400> SEQUENCE: 84
cttactggca tttggatcgt tcttgtcaac ctttgtcttg atatcacgta agtaatagtc    60

<210> SEQ ID NO 85
<211> LENGTH: 60
<212> TYPE: DNA
<213> ORGANISM: Artificial Sequence
<220> FEATURE:
<223> OTHER INFORMATION: Constructs of S. cerevisiae squalene synthase
      cloned into the Yep352 vector
<220> FEATURE:
<221> NAME/KEY: misc_binding
<222> LOCATION: (1)..(60)

<400> SEQUENCE: 85
acactaaacc gacttgaagc cgttcagaaa ctctgcagag aaatgtacca ggataaatta    60

<210> SEQ ID NO 86
<211> LENGTH: 60
<212> TYPE: DNA
<213> ORGANISM: Artificial Sequence
<220> FEATURE:
<223> OTHER INFORMATION: Constructs of S. cerevisiae squalene synthase
      cloned into the Yep352 vector -continued

```
<220> FEATURE:
<221> NAME/KEY: misc_binding
<222> LOCATION: (1)..(60)

<400> SEQUENCE: 86
tctgcagagt ttctgaacgg cttcaagtcg gtttagtgtt tttaagaaat ttggatcttg    60

<210> SEQ ID NO 87
<211> LENGTH: 43
<212> TYPE: DNA
<213> ORGANISM: Artificial Sequence
<220> FEATURE:
<223> OTHER INFORMATION: Constructs of A. thaliana squalene synthase
      cloned into the Yep352 vector
<220> FEATURE:
<221> NAME/KEY: misc_binding
<222> LOCATION: (1)..(43)

<400> SEQUENCE: 87
cttgaaaaga tcgaacagct ctgcagagac gctggagttc ttc                       43

<210> SEQ ID NO 88
<211> LENGTH: 44
<212> TYPE: DNA
<213> ORGANISM: Artificial Sequence
<220> FEATURE:
<223> OTHER INFORMATION: Constructs of A. thaliana squalene synthase
      cloned into the Yep352 vector
<220> FEATURE:
<221> NAME/KEY: misc_binding
<222> LOCATION: (1)..(44)

<400> SEQUENCE: 88
cagagctgtt cgatcttttc aagtcggttt agtgtcttac tggc                      44

<210> SEQ ID NO 89
<211> LENGTH: 50
<212> TYPE: DNA
<213> ORGANISM: Artificial Sequence
<220> FEATURE:
<223> OTHER INFORMATION: Constructs of A. thaliana squalene synthase
      cloned into the Yep352 vector
<220> FEATURE:
<221> NAME/KEY: misc_binding
<222> LOCATION: (1)..(50)

<400> SEQUENCE: 89
aatttcttaa aattgaacat tcaacttgaa gccgttcaga aactctgcag                50

<210> SEQ ID NO 90
<211> LENGTH: 50
<212> TYPE: DNA
<213> ORGANISM: Artificial Sequence
<220> FEATURE:
<223> OTHER INFORMATION: Constructs of A. thaliana squalene synthase
      cloned into the Yep352 vector
<220> FEATURE:
<221> NAME/KEY: misc_binding
<222> LOCATION: (1)..(50)

<400> SEQUENCE: 90
aagttgaatg ttcaatttta agaaatttgg atcgttcttg tcaacctttg                50

<210> SEQ ID NO 91
<211> LENGTH: 58
<212> TYPE: DNA
<213> ORGANISM: Artificial Sequence
<220> FEATURE:
<223> OTHER INFORMATION: Constructs of A. thaliana squalene synthase
```

```
          cloned into the Yep352 vector
<220> FEATURE:
<221> NAME/KEY: misc_binding
<222> LOCATION: (1)..(58)

<400> SEQUENCE: 91
ttcttaaaat tgaacattca aatctccaag atcgaacagc tctgcagaga cgctggag          58

<210> SEQ ID NO 92
<211> LENGTH: 60
<212> TYPE: DNA
<213> ORGANISM: Artificial Sequence
<220> FEATURE:
<223> OTHER INFORMATION: Constructs of A. thaliana squalene synthase
      cloned into the Yep352 vector
<220> FEATURE:
<221> NAME/KEY: misc_binding
<222> LOCATION: (1)..(60)

<400> SEQUENCE: 92
ctgttcgatc ttggagattt gaatgttcaa ttttaagaaa tttggatcgt tcttgtcaac        60

<210> SEQ ID NO 93
<211> LENGTH: 60
<212> TYPE: DNA
<213> ORGANISM: Artificial Sequence
<220> FEATURE:
<223> OTHER INFORMATION: Constructs of A. thaliana squalene synthase
      cloned into the Yep352 vector
<220> FEATURE:
<221> NAME/KEY: misc_binding
<222> LOCATION: (1)..(60)

<400> SEQUENCE: 93
aaatctaaat tggctgtgca agatccaaat ttcttaaaaa cactaaaccg acttgaagcc        60

<210> SEQ ID NO 94
<211> LENGTH: 60
<212> TYPE: DNA
<213> ORGANISM: Artificial Sequence
<220> FEATURE:
<223> OTHER INFORMATION: Constructs of A. thaliana squalene synthase
      cloned into the Yep352 vector
<220> FEATURE:
<221> NAME/KEY: misc_binding
<222> LOCATION: (1)..(60)

<400> SEQUENCE: 94
ttttaagaaa tttggatctt gcacagccaa tttagatttc agcatgcagg aaaaatcata       60

<210> SEQ ID NO 95
<211> LENGTH: 60
<212> TYPE: DNA
<213> ORGANISM: Artificial Sequence
<220> FEATURE:
<223> OTHER INFORMATION: Constructs of A. thaliana squalene synthase
      cloned into the Yep352 vector
<220> FEATURE:
<221> NAME/KEY: misc_binding
<222> LOCATION: (1)..(60)

<400> SEQUENCE: 95
ttgaacattc aaatctccaa gatcgaacag tttatggaag acgctggagt tcttcaaaac       60

<210> SEQ ID NO 96
<211> LENGTH: 60
<212> TYPE: DNA
<213> ORGANISM: Artificial Sequence
<220> FEATURE:
```

```
<223> OTHER INFORMATION: Constructs of A. thaliana squalene synthase
      cloned into the Yep352 vector
<220> FEATURE:
<221> NAME/KEY: misc_binding
<222> LOCATION: (1)..(60)

<400> SEQUENCE: 96
ttccataaac tgttcgatct tggagatttg aatgttcaac ttactggcat ttggatcgtt      60

<210> SEQ ID NO 97
<211> LENGTH: 39
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (2)..(9)

<400> SEQUENCE: 97
aggcgcgcca aaacaatgtc taaaggtgaa gaattattc                             39

<210> SEQ ID NO 98
<211> LENGTH: 39
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (3)..(8)

<400> SEQUENCE: 98
ccgctcgaga aaacaatggt gcgctcctcc aagaacgtc                             39

<210> SEQ ID NO 99
<211> LENGTH: 39
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (3)..(9)

<400> SEQUENCE: 99
aggcgcgcca aaacaatggt gcgctcctcc aagaacgtc                             39

<210> SEQ ID NO 100
<211> LENGTH: 52
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (1)..(52)

<400> SEQUENCE: 100
cataccagaa ccaccaccag aaccaccttt gtacaattca tccataccat gg              52

<210> SEQ ID NO 101
<211> LENGTH: 49
<212> TYPE: DNA
<213> ORGANISM: Artificial Sequence
```

```
<220> FEATURE:
<223> OTHER INFORMATION: Fluorescence protein tagged squalene synthase
      construct primer
<220> FEATURE:
<221> NAME/KEY: misc_binding
<222> LOCATION: (1)..(49)

<400> SEQUENCE: 101
cataccagaa ccaccaccag aaccacccag gaacaggtgg tggcggccc                49

<210> SEQ ID NO 102
<211> LENGTH: 51
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (1)..(51)

<400> SEQUENCE: 102
caaaggtggt tctggtggtg gttctggtat gggaaagcta ttacaattgg c            51

<210> SEQ ID NO 103
<211> LENGTH: 53
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (1)..(53)

<400> SEQUENCE: 103
caaaggtggt tctggtggtg gttctggtat ggggatgctt cgctggggag tgg          53

<210> SEQ ID NO 104
<211> LENGTH: 53
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (1)..(53)

<400> SEQUENCE: 104
cctgggtggt tctggtggtg gttctggtat ggggatgctt cgctggggag tgg          53

<210> SEQ ID NO 105
<211> LENGTH: 33
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (2)..(7)

<400> SEQUENCE: 105
gctctagatc acgctctgtg taaagtgtat ata                                33

<210> SEQ ID NO 106
<211> LENGTH: 38
<212> TYPE: DNA
```

```
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (3)..(8)

<400> SEQUENCE: 106
gctctagatc acttgtactc ttcttcttgt tgggttgg                              38

<210> SEQ ID NO 107
<211> LENGTH: 40
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (9)..(16)

<400> SEQUENCE: 107
ataagaatgc ggccgcttag gcgctgagtg tgggtctagg                            40

<210> SEQ ID NO 108
<211> LENGTH: 32
<212> TYPE: DNA
<213> ORGANISM: Artificial Sequence
<220> FEATURE:
<223> OTHER INFORMATION: Fluorescence protein tagged squalene synthase
      construct primer
<220> FEATURE:
<221> NAME/KEY: misc_binding
<222> LOCATION: (2)..(7)

<400> SEQUENCE: 108
gctctagatt aggcgctgag tgtgggtcta gg                                    32

<210> SEQ ID NO 109
<211> LENGTH: 42
<212> TYPE: DNA
<213> ORGANISM: Artificial Sequence
<220> FEATURE:
<223> OTHER INFORMATION: Primer for creating C-terminus squalene
      synthase construct for S. cerevisiae
<220> FEATURE:
<221> NAME/KEY: C_region
<222> LOCATION: (2)..(7)

<400> SEQUENCE: 109
ggaattcaaa acaatgaaat ctaaattggc tgtgcaagat cc                         42

<210> SEQ ID NO 110
<211> LENGTH: 43
<212> TYPE: DNA
<213> ORGANISM: Artificial Sequence
<220> FEATURE:
<223> OTHER INFORMATION: Primer for creating C-terminus squalene
      synthase construct for S. cerevisiae
<220> FEATURE:
<221> NAME/KEY: C_region
<222> LOCATION: (3)..(8)

<400> SEQUENCE: 110
cgggatccaa acaatgaaa tctaaattgg ctgtgcaaga tcc                         43

<210> SEQ ID NO 111
<211> LENGTH: 36
```

-continued

```
<212> TYPE: DNA
<213> ORGANISM: Artificial Sequence
<220> FEATURE:
<223> OTHER INFORMATION: Primer for creating C-terminus squalene
      synthase construct for S. cerevisiae
<220> FEATURE:
<221> NAME/KEY: C_region
<222> LOCATION: (2)..(7)

<400> SEQUENCE: 111
ggaattcaaa acaatgtacc aggataaatt acctcc                               36

<210> SEQ ID NO 112
<211> LENGTH: 37
<212> TYPE: DNA
<213> ORGANISM: Artificial Sequence
<220> FEATURE:
<223> OTHER INFORMATION: Primer for creating C-terminus squalene
      synthase construct for S. cerevisiae
<220> FEATURE:
<221> NAME/KEY: C_region
<222> LOCATION: (3)..(7)

<400> SEQUENCE: 112
cgggatccaa acaatgtac caggataaat tacctcc                               37

<210> SEQ ID NO 113
<211> LENGTH: 42
<212> TYPE: DNA
<213> ORGANISM: Artificial Sequence
<220> FEATURE:
<223> OTHER INFORMATION: Primer for creating C-terminus squalene
      synthase construct for S. cerevisiae
<220> FEATURE:
<221> NAME/KEY: C_region
<222> LOCATION: (9)..(16)

<400> SEQUENCE: 113
ataagaatgc ggccgctcac gctctgtgta aagtgtatat at                        42

<210> SEQ ID NO 114
<211> LENGTH: 37
<212> TYPE: DNA
<213> ORGANISM: Artificial Sequence
<220> FEATURE:
<223> OTHER INFORMATION: Primer for creating C-terminus squalene
      synthase construct for S. cerevisiae
<220> FEATURE:
<221> NAME/KEY: C_region
<222> LOCATION: (6)..(11)

<400> SEQUENCE: 114
aacccaagct ttcacgctct gtgtaaagtg tatatat                              37

<210> SEQ ID NO 115
<211> LENGTH: 42
<212> TYPE: DNA
<213> ORGANISM: Artificial Sequence
<220> FEATURE:
<223> OTHER INFORMATION: Primer for creating C-terminus squalene
      synthase construct for A. thaliana
<220> FEATURE:
<221> NAME/KEY: C_region
<222> LOCATION: (2)..(7)

<400> SEQUENCE: 115
ggaattcaaa acaatgaaga caaaggttga caagaacgat cc                        42

<210> SEQ ID NO 116
```

```
<211> LENGTH: 43
<212> TYPE: DNA
<213> ORGANISM: Artificial Sequence
<220> FEATURE:
<223> OTHER INFORMATION: Primer for creating C-terminus squalene
      synthase construct for A. thaliana
<220> FEATURE:
<221> NAME/KEY: C_region
<222> LOCATION: (3)..(8)

<400> SEQUENCE: 116
cgggatccaa aacaatgaag acaaaggttg acaagaacga tcc                43

<210> SEQ ID NO 117
<211> LENGTH: 43
<212> TYPE: DNA
<213> ORGANISM: Artificial Sequence
<220> FEATURE:
<223> OTHER INFORMATION: Primer for creating C-terminus squalene
      synthase construct for A. thaliana
<220> FEATURE:
<221> NAME/KEY: C_region
<222> LOCATION: (9)..(16)

<400> SEQUENCE: 117
ataagaatgc ggccgctcag tttgctctga gatatgcaaa gac                43

<210> SEQ ID NO 118
<211> LENGTH: 38
<212> TYPE: DNA
<213> ORGANISM: Artificial Sequence
<220> FEATURE:
<223> OTHER INFORMATION: Primer for creating C-terminus squalene
      synthase construct for A. thaliana
<220> FEATURE:
<221> NAME/KEY: C_region
<222> LOCATION: (6)..(11)

<400> SEQUENCE: 118
aacccaagct ttcagtttgc tctgagatat gcaaagac                      38

<210> SEQ ID NO 119
<211> LENGTH: 40
<212> TYPE: DNA
<213> ORGANISM: Artificial Sequence
<220> FEATURE:
<223> OTHER INFORMATION: Primer for creating C-terminus squalene
      synthase construct for B. braunii
<220> FEATURE:
<221> NAME/KEY: C_region
<222> LOCATION: (2)..(7)

<400> SEQUENCE: 119
ggaattcaaa acaatggaag tcagatgcaa caccgagacc                    40

<210> SEQ ID NO 120
<211> LENGTH: 40
<212> TYPE: DNA
<213> ORGANISM: Artificial Sequence
<220> FEATURE:
<223> OTHER INFORMATION: Primer for creating C-terminus squalene
      synthase construct for B. braunii
<220> FEATURE:
<221> NAME/KEY: C_region
<222> LOCATION: (9)..(16)

<400> SEQUENCE: 120
ataagaatgc ggccgcttag gcgctgagtg tgggtctagg                    40
```

```
<210> SEQ ID NO 121
<211> LENGTH: 35
<212> TYPE: DNA
<213> ORGANISM: Artificial Sequence
<220> FEATURE:
<223> OTHER INFORMATION: Primer for creating C-terminus squalene
      synthase construct for B. braunii
<220> FEATURE:
<221> NAME/KEY: C_region
<222> LOCATION: (6)..(11)

<400> SEQUENCE: 121
aacccaagct tttaggcgct gagtgtgggt ctagg                          35

<210> SEQ ID NO 122
<211> LENGTH: 1335
<212> TYPE: DNA
<213> ORGANISM: Saccharomyces cerevisiae

<400> SEQUENCE: 122
atgggaaagc tattacaatt ggcattgcat ccggtcgaga tgaaggcagc tttgaagctg    60
aagttttgca gaacaccgct attctccatc tatgatcagt ccacgtctcc atatctcttg   120
cactgtttcg aactgttgaa cttgacctcc agatcgtttg ctgctgtgat cagagagctg   180
catccagaat tgagaaactg tgttactctc ttttatttga ttttaagggc tttggatacc   240
atcgaagacg atatgtccat cgaacacgat ttgaaaattg acttgttgcg tcacttccac   300
gagaaattgt tgttaactaa atggagtttc gacggaaatg ccccgatgt gaaggacaga   360 gccgttttga cagatttcga atcgattctt attgaattcc acaaattgaa accagaatat   420
caagaagtca tcaaggagat caccgagaaa atgggtaatg gtatggccga ctacatctta   480
gatgaaaatt acaacttgaa tgggttgcaa accgtccacg actacgacgt gtactgtcac   540
tacgtagctg gtttggtcgg tgatggtttg accgtttga ttgtcattgc caagtttgcc   600
aacgaatctt tgtattctaa tgagcaattg tatgaaagca tgggtctttt cctacaaaaa   660
accaacatca tcagagatta caatgaagat ttggtcgatg gtagatcctt ctggccaag   720 gaaatctggt cacaatacgc tcctcagttg aaggacttca tgaaacctga aaacgaacaa   780
ctggggttgg actgtataaa ccacctcgtc ttaaacgcat tgagtcatgt tatcgatgtg   840
ttgacttatt tggccggtat ccacgagcaa tccactttcc aatttgtgc cattccccaa   900 gttatggcca ttgcaacctt ggctttggta ttcaacaacc gtgaagtgct acatggcaat   960
gtaaagattc gtaagggtac tacctgctat ttaatttga atcaaggac tttgcgtggc  1020 tgtgtcgaga tttttgacta ttacttacgt gatatcaaat ctaaattggc tgtgcaagat  1080
ccaaatttct taaaattgaa cattcaaatc tccagatcg aacagtttat ggaagaaatg  1140
taccaggata aattacctcc taacgtgaag ccaaatgaaa ctccaatttt cttgaaagtt  1200
aaagaaagat ccagatacga tgatgaattg gttccaaccc aacaagaaga agagtacaag  1260
ttcaatatgg ttttatctat catccttgtcc gttcttcttg ggttttatta tatatacact  1320
ttacacagag cgtga                                                   1335

<210> SEQ ID NO 123
<211> LENGTH: 1263
<212> TYPE: DNA
<213> ORGANISM: Saccharomyces cerevisiae

<400> SEQUENCE: 123
atgggaaagc tattacaatt ggcattgcat ccggtcgaga tgaaggcagc tttgaagctg    60
```

```
aagttttgca gaacaccgct attctccatc tatgatcagt ccacgtctcc atatctcttg      120
cactgtttcg aactgttgaa cttcacctcc agatcgtttg ctgctgtgat cagagagctg      180
catccagaat tgagaaactg tgttactctc ttttatttga ttttaagggc tttggatacc      240
atcgaagacg atatgtccat cgaacacgat ttgaaaattg acttgttgcg tcacttccac      300
gagaaattgt tgttaactaa atggagtttc gacggaaatg cccccgatgt gaaggacaga      360
gccgttttga cagatttcga atcgattctt attgaattcc acaaattgaa accagaatat      420
caagaagtca tcaaggagat caccgagaaa atgggtaatg gtatggccga ctacatctta      480
gatgaaaatt acaacttgaa tgggttgcaa accgtccacg actacgacgt gtactgtcac      540
tacgtagctg gtttggtcgg tgatggtttg acccgtttga ttgtcattgc caagtttgcc      600
aacgaatctt tgtattctaa tgagcaattg tatgaaagca tgggtctttt cctacaaaaa      660
accaacatca tcagagatta caatgaagat ttggtcgatg gtagatcctt ctggcccaag      720
gaaatctggt cacaatacgc tcctcagttg aaggacttca tgaaacctga aaacgaacaa      780
ctggggttgg actgtataaa ccacctcgtc ttaaacgcat tgagtcatgt tatcgatgtg      840
ttgacttatt tggccggtat ccacgagcaa tccactttcc aattttgtgc cattccccaa      900
gttatggcca ttgcaacctt ggctttggta ttcaacaacc gtgaagtgct acatggcgat      960
gtaaagattc gtaagggtac tacctgctgt ttaattttga aatcaaggac tttgcgtggc     1020
tgtgtcgaga ttttttgacta ttacttacgt gatatcaaat ctaaattggc tgtgcaagat     1080
ccaaatttct taaaattgaa cattcaaatc tccaagatcg aacagtttat ggaagaaatg     1140
taccaggata aattacctcc taacgtgaag ccaaatgaaa ctccaatttt cttgaaagtt     1200
aaagaaagat ccagatacga tgatgaattg gttccaaccc aacaagaaga agagtacaag     1260
tga                                                                  1263
```

<210> SEQ ID NO 124
<211> LENGTH: 1386
<212> TYPE: DNA
<213> ORGANISM: Botryococcus braunii

<400> SEQUENCE: 124

```
atggggatgc ttcgctgggg agtggagtct ttgcagaatc cagatgaatt aatcccggtc       60
ttgaggatga tttatgctga taagtttgga aagatcaagc caaggacga agaccggggc      120 ttctgctatg aaattttaaa ccttgtttca agaagttttg caatcgtcat ccaacagctc      180
cctgcacagc tgagggaccc agtctgcata ttttaccttg tactacgcgc cctggacaca      240
gtcgaagatg atatgaaaat tgcagcaacc accaagattc ccttgctgcg tgactttat       300 gagaaatttt ctgacaggtc attccgcatg acggccggag atcaaaaaga ctacatcagg      360
ctgttggatc agtaccccaa agtgacaagc gttttcttga aattgacccc ccgtgaacaa      420
gagataattg cagacattac aaagcggatg ggaatggaa tggctgactt cgtgcataag      480
ggtgttcccg acacagtggg ggactacgac ctttactgcc actatgttgc tggggtggtg      540
ggtctcgggc tttcccagtt gttcgttgcg agtggactac agtcaccctc tttgacccgc      600
agtgaagacc tttccaatca catgggcctc ttccttcaga agaccaacat catccgcgac      660
tactttgagg acatcaatga gctgcctgcc cccggatgt tctggcccag agagatctgg      720
ggcaagtatg cgaacaacct cgctgagttc aaagacccgg ccaacaaggc ggctgcaatg      780
tgctgcctca acgagatggt cacagatgca ttgaggcacg cggtgtactg cctgcagtac      840
atgtccatga ttgaggatcc gcagatcttc aacttctgtg ccatccctca gaccatggcc      900
```

```
ttcggcaccc tgtctttgtg ttacaacaac tacactatct tcacagggcc caaagcggct    960
gtgaagctgc gtaggggcac cactgccaag ctgatgtaca cctctaacaa tatgtttgcg   1020
atgtaccgtc atttcctcaa cttcgcagag aagctggaag tcagatgcaa caccgagacc   1080
agcgaggatc ccagcgtgac caccactctg gaacacctgc ataagatcaa agctgcctgc   1140
aaggctgggc tggcacgcac aaaagatgac acctttgacg aattgaggag caggttgtta   1200
gcgctgacgg gaggcagctt ctacctcgcc tggacctaca atttcctaga ccttcgaggc   1260
ccgggagacc tgcccacctt cttatctgta acccaacatt ggtggtctat tctgatcttc   1320
ctcatttcga ttgccgtctt ctttattccg tcgaggccct cacctagacc cacactcagc   1380
gcctaa                                                              1386
```

<210> SEQ ID NO 125
<211> LENGTH: 1251
<212> TYPE: DNA
<213> ORGANISM: Rattus rattus

<400> SEQUENCE: 125

```
atggagttcg tgaagtgtct aggccacccg gaggagttct acaacctgct gcgattccgc     60
atgggaggcc ggcggaattt catacccaag atggaccgga actcgctcag caacagcttg    120
aagacttgct ataagtatct tgatcagacc agtcgcagct tcgccgcggt tatccaggcg    180
ctggatgggg acatacgtca tgcggtgtgt gtgttttacc tgatcctccg agccatggac    240
acagtggagg atgacatggc catcagtgtg gagaagaaga tcccactgct gcgaaacttt    300
cacactttcc tctatgagcc ggagtggcgg ttcaccgaga gcaaggagaa gcaccgagta    360
gtgctgaggg acttccccac gatctcccgg gagtttagaa atttggctga gaaatatcaa    420
acagtgatcg ctgacatctg tcacaggatg ggatgtggga tggcagaatt tctaaacaag    480
gatgtaacct ccaaacagga ctgggacaag tactgtcact atgttgctgg actggtggga    540
atcggccttt ctcgcctatt ctctgcctca gagtttgaag atcccatagt tggtgaagac    600
acagagtgtg ccaattctat gggtctgttt ctgcagaaaa caaatatcat tcgtgattat    660
ctggaagacc aacaagaagg aagacagttt tggcctcaag aggtatgggg caaatatgtt    720
aagaagctgg aagactttgt taagccagag aacgtagatg tggccgtgaa gtgcttgaat    780
gaactcataa ccaacgccct acaacacatc cctgacgtca tcacctacct gtcaaggctc    840
cggaaccaaa gtgtgtttaa cttctgtgcc attccacagg taatggccat tgctacgctg    900
gctgcctgtt acaataacca tcaggtattc aagggagtag tgaagattcg gaaggggcaa    960
gcagttaccc tcatgatgga tgccaccaac atgccagctg tcaaagctat catataccag   1020
tacatagaag agatttatca ccgggtcccc aactcagacc cgtcagctag caaggccaag   1080
cagctcatct ccaacatcag gacgcagagc cttcccaatt gccagctcat ctcccgaagc   1140
cactactccc ccatttacct gtccttcatc atgctcttgg ctgccctgag ctggcagtac   1200
ttgagcactc tgtcccaggt cacagaagac tatgtccaga gagaacactg a            1251
```

<210> SEQ ID NO 126
<211> LENGTH: 1236
<212> TYPE: DNA
<213> ORGANISM: Nicotiana tabacum

<400> SEQUENCE: 126

```
atggggagtt tgagggctat tctgaagaat ccagaggatt tatatccatt ggtgaagctg     60
```

-continued

| | |
|---|---|
| aagctagcgg ctcgacacgc ggagaagcag atcccgccgt ctccaaattg gggcttctgt | 120 |
| tactcaatgc ttcataaggt ttctcgtagc tttgctctcg tcattcaaca acttccagtc | 180 |
| gagcttcgtg acgccgtgtg catttttctat ttggttcttc gagcacttga cactgttgag | 240 |
| gatgatacca gcattcccac cgatgttaaa gttcctattc tgatctcttt tcatcagcat | 300 |
| gtttatgatc gcgaatggca ttttcatgt ggtacaaagg agtacaaggt tctcatggac | 360 |
| cagttccatc atgtatcaac tgcttttctg gagcttagga acattatca gcaggcaatt | 420 |
| gaggatatta ccatgaggat gggtgcagga atggcaaaat tcatatgcaa ggaggtggaa | 480 |
| acaaccgatg attatgacga atattgtcac tatgtagctg gcttgttgg gctaggattg | 540 |
| tcaaaactgt tccatgcctc tgagaaagaa gatctggctt cagattctct ctccaactcc | 600 |
| atgggtttat ttcttcagaa aacaaacatc attagagatt atttggaaga cataaatgaa | 660 |
| gtacccaagt gccgtatgtt ctggccccgt gaaatatgga gtaaatatgt taacaagctt | 720 |
| gaggaattaa agtacgagga taactcggcc aaagcagtgc aatgtctaaa tgacatggtc | 780 |
| actaatgctt tatcacatgt agaagattgt ttgacttaca tgtctgcttt gcgtgatcct | 840 |
| tccatctttc gattctgtgc tattccacag gtcatggcaa ttgggacatt agctatgtgc | 900 |
| tacgacaaca ttgaagtctt cagaggagtg gtaaaaatga gacgtggtct gactgctaag | 960 |
| gtcattgacc ggaccaggac tattgcagat gtatatggtg ctttttttga cttttcttgt | 1020 |
| atgctgaaat ccaaggttaa taataatgat ccaaatgcaa caaaaactct gaagaggctc | 1080 |
| gaagtgatcc tgaaaacttg cagagattcg ggaaccttga acaaaggaa atcctacata | 1140 |
| atcaggagcg agcctaatta cagtccagtt ctgattgttg tcattttcat catactggct | 1200 |
| attattctcg cacagctatc cggaaaccga tcttag | 1236 |

<210> SEQ ID NO 127
<211> LENGTH: 1233
<212> TYPE: DNA
<213> ORGANISM: Arabidopsis thaliana

<400> SEQUENCE: 127

| | |
|---|---|
| atggggagct tggggacgat gctgagatat cccgatgata tatatccgct cctgaagatg | 60 |
| aaacgagcga ttgagaaagc ggagaagcag atccctcctg agccacactg gggtttctgc | 120 |
| tattcgatgc tccacaaggt ttctcgaagc ttttctctcg ttattcagca actcaacacc | 180 |
| gagctccgta acgccgtgtg tgtgttctac ttggttctcc gagctcttga tactgttgag | 240 |
| gatgatacta gcataccaac tgatgaaaag gttcccatcc tgatagcttt tcaccggcac | 300 |
| atatacgata ctgattggca ttattcatgt ggtacgaagg agtacaagat tctaatggac | 360 |
| caatttcacc atgtttctgc agctttttg gaacttgaaa aagggtatca agaggctatc | 420 |
| gaggaaatta ctagaagaat gggtgcaggg atggccaagt ttatctgcca agaggtagaa | 480 |
| actgttgatg actacgatga atactgccac tatgttgctg gcttgttgg tttaggtttg | 540 |
| tcgaaactct tcctcgctgc aggatcagag gttttgacac cagattggga ggcgatttcc | 600 |
| aattcaatgg gtttatttct acagaaaaca acattatca gagattatct tgaggacatt | 660 |
| aatgagatac caaatcccg catgttttgg cctcgcgaga tttggggcaa atatgctgac | 720 |
| aagcttgagg atttaaaata cgaggagaac acaaacaaat ccgtacagtg cttaaatgaa | 780 |
| atggttacca atgcgttgat gcatattgaa gattgcctga atacatggtt tccttgcgt | 840 |
| gatccttcca tatttcggtt ctgtgccatc cctcagatca tggcgattgg aacacttgca | 900 |
| ttatgctata caatgaaca agtattcaga ggcgttgtga aactgaggcg aggtcttact | 960 |

```
gctaaagtca ttgatcgtac aaagacaatg gctgatgtct atggtgcttt ctatgatttt    1020
tcctgcatgc tgaagacaaa ggttgacaag aacgatccaa atgccagtaa gacactaaac    1080
cgacttgaag ccgttcagaa actctgcaga gacgctggag ttcttcaaaa cagaaaatct    1140
tatgttaatg acaaaggaca accaaacagt gtctttatta taatggttgt gattctactg    1200
gccatagtct ttgcatatct cagagcaaac tga                                 1233
```

```
<210> SEQ ID NO 128
<211> LENGTH: 1335
<212> TYPE: DNA
<213> ORGANISM: Artificial Sequence
<220> FEATURE:
<223> OTHER INFORMATION: Chimeric squalene synthase gene consisting of
      1,104 bp of the Botryococcus braunii squalene synthase encoding
      for the amino terminal 368 amino acids and 228 bp of the yeast
      gene encoding for 76 amino acids of the carboxy terminal domain
<220> FEATURE:
<221> NAME/KEY: misc_binding
<222> LOCATION: (1)..(1335)

<400> SEQUENCE: 128
```

```
atggggatgc ttcgctgggg agtggagtct tgcagaatc cagatgaatt aatcccggtc      60
ttgaggatga tttatgctga taagtttgga aagatcaagc caaaggacga agaccggggc    120
ttctgctatg aaattttaaa ccttgtttca agaagttttg caatcgtcat ccaacagctc    180
cctgcacagc tgagggaccc agtctgcata ttttaccttg tactacgcgc cctggacaca    240
gtcgaagatg atatgaaaat tgcagcaacc accaagattc ccttgctgcg tgactttat    300 gagaaatttc tgacaggtc attccgcatg acggccggag atcaaaaaga ctacatcagg    360
ctgttggatc agtaccccaa agtgacaagc gttttcttga aattgacccc ccgtgaacaa    420
gagataattg cagacattac aaagcggatg gggaatggaa tggctgactt cgtgcataag    480
ggtgttcccg acacagtggg ggactacgac ctttactgcc actatgttgc tggggtggtg    540
ggtctcgggc tttcccagtt gttcgttgcg agtggactac agtcaccctc tttgacccgc    600
agtgaagacc tttccaatca catgggcctc ttccttcaga agaccaacat catccgcgac    660
tactttgagg acatcaatga gctgcctgcc ccccggatgt tctggcccag agatctctgg    720
ggcaagtatg cgaacaacct cgctgagttc aaagacccgg ccaacaaggc ggctgcaatg    780
tgctgcctca cgagatggt cacagatgca ttgaggcacg cggtgtactg cctgcagtac    840
atgtccatga ttgaggatcc gcagatcttc aacttctgtg ccatccctca gaccatggcc    900
ttcggcaccc tgtctttgtg ttacaacaac tacactatct tcacgggcc aaagcggct    960 gtgaagctgc gtagggcac cactgccaag ctgatgtaca cctctaacaa tatgtttgcg    1020
atgtaccgtc atttcctcaa cttcgcagag aagcttaaat ctaaattggc tgtgcaagat    1080
ccaaatttct taaaattgaa cattcaaatc tccaagatcg aacagtttat ggaagaaatg    1140
taccaggata aattacctcc taacgtgaag ccaaatgaaa ctccaatttt cttgaaagtt    1200
aaagaaagat ccagatacga tgatgaattg gttccaaccc aacaagaaga agagtacaag    1260
ttcaatatgg ttttatctat catctcgtcc gttcttcttg ggtttttatta tatatacact    1320 ttacacagag cgtga                                                    1335
```

```
<210> SEQ ID NO 129
<211> LENGTH: 1263
<212> TYPE: DNA
<213> ORGANISM: Artificial Sequence
<220> FEATURE:
```

<223> OTHER INFORMATION: Chimeric squalene synthase gene consisting of
     1,104 bp of the Botryococcus braunii squalene synthase, followed
     by 155 bp of the carboxy terminal domain of the yeast squalene
     synthase
<220> FEATURE:
<221> NAME/KEY: misc_binding
<222> LOCATION: (1)..(1263)

<400> SEQUENCE: 129

| | | |
|---|---|---|
| atgggggatgc ttcgctgggg agtggagtct tgcagaatc cagatgaatt aatcccggtc | 60 |
| ttgaggatga tttatgctga taagtttgga aagatcaagc caaggacga agaccggggc | 120 |
| ttctgctatg aaatttaaa ccttgtttca gaagtttg caatcgtcat ccaacagctc | 180 |
| cctgcacagc tgagggaccc agtctgcata ttttaccttg tactacgcgc cctggacaca | 240 |
| gtcgaagatg atatgaaaat tgcagcaacc accaagattc ccttgctgcg tgacttttat | 300 |
| gagaaaattt ctgacaggtc attccgcatg acggccggag atcaaaaaga ctacatcagg | 360 |
| ctgttggatc agtaccccaa agtgacaagc gtttcttga aattgacccc ccgtgaacaa | 420 |
| gagataattg cagacattac aaagcggatg gggaatggaa tggctgactt cgtgcataag | 480 |
| ggtgttcccg acacagtggg ggactacgac ctttactgcc actatgttgc tggggtggtg | 540 |
| ggtctcgggc tttcccagtt gttcgttgcg agtggactac agtcaccctc tttgacccgc | 600 |
| agtgaagacc tttccaatca catgggcctc ttccttcaga agaccaacat catccgcgac | 660 |
| tactttgagg acatcaatga gctgcctgcc ccccggatgt tctggcccag agatctggg | 720 |
| ggcaagtatg cgaacaacct cgctgagttc aaagacccgg ccaacaaggc ggctgcaatg | 780 |
| tgctgcctca acgagatggt cacagatgca ttgaggcacg cggtgtactg cctgcagtac | 840 |
| atgtccatga ttgaggatcc gcagatcttc aacttctgtg ccatccctca gaccatggcc | 900 |
| ttcggcaccc tgtctttgtg ttacaacaac tacactatct tcacagggcc caaagcggct | 960 |
| gtgaagctgc gtaggggcac cactgccaag ctgatgtaca cctctaacaa tatgtttttgcg | 1020 |
| atgtaccgtc atttcctcaa cttcgcgagg aagcttaaat ctaaattggc tgtgcaagat | 1080 |
| ccaaatttct taaaattgaa cattcaaatc tccaagatcg aacagtttat ggaagaaatg | 1140 |
| taccaggata aattacctcc taacgtgaag ccaaatgaaa ctccaatttt cttgaaagtt | 1200 |
| aaagaaagat ccagatacga tgatgaattg gttccaaccc aacaagaaga agagtacaag | 1260 |
| tga | 1263 |

<210> SEQ ID NO 130
<211> LENGTH: 1386
<212> TYPE: DNA
<213> ORGANISM: Artificial Sequence
<220> FEATURE:
<223> OTHER INFORMATION: Chimeric squalene synthase consisting of first
     1,056 bp of the yeast squalene synthase gene coding for the first
     352 amino acids, followed by 330 bp coding for the carboxy
     terminal 110 amino acids of the Botryococcus braunii squalene
     synthase
<220> FEATURE:
<221> NAME/KEY: misc_binding
<222> LOCATION: (1)..(1386)

<400> SEQUENCE: 130

| | | |
|---|---|---|
| atgggaaagc tattacaatt ggcattgcat ccggtcgaga tgaaggcagc tttgaagctg | 60 |
| aagtttttgca gaacaccgct attctccatc tatgatcagt ccacgtctcc atatctcttg | 120 |
| cactgtttcg aactgttgaa cttgacctcc agatcgtttg ctgctgtgat cagagagctg | 180 |
| catccagaat tgagaaactg tgttactctc ttttatttga ttttaagggc tttggatacc | 240 |

```
atcgaagacg atatgtccat cgaacacgat ttgaaaattg acttgttgcg tcacttccac    300
gagaaattgt tgttaactaa atggagtttc gacggaaatg ccccgatgt gaaggacaga     360 gccgttttga cagatttcga atcgattctt attgaattcc acaaattgaa accagaatat    420
caagaagtca tcaaggagat caccgagaaa atgggtaatg gtatggccga ctacatctta    480
gatgaaaatt acaacttgaa tgggttgcaa accgtccacg actacgacgt gtactgtcac    540
tacgtagctg gttggtcgg tgatggtttg acccgtttga ttgtcattgc caagtttgcc     600
aacgaatctt tgtattctaa tgagcaattg tatgaaagca tgggtctttt cctacaaaaa    660
accaacatca tcagagatta caatgaagat tggtcgatg gtagatcctt ctggcccaag     720
gaaatctggt cacaatacgc tcctcagttg aaggacttca tgaaacctga aaacgaacaa    780
ctggggttgg actgtataaa ccacctcgtc ttaaacgcat tgagtcatgt tatcgatgtg    840
ttgacttatt tggccggtat ccacgagcaa tccactttcc aattttgtgc cattccccaa    900
gttatggcca ttgcaacctt ggctttggta ttcaacaacc gtgaagtgct acatggcaat    960
gtaaagattc gtaagggtac tacctgctat ttaattttga aatcaaggac tttgcgtggc   1020
tgtgtcgaga ttttgactac ttacttacgt gatatcgaag tcagatgcaa caccgagacc   1080
agcgaggatc ccagcgtgac caccactctg gaacacctgc ataagatcaa agctgcctgc   1140
aaggctgggc tggcacgcac aaaagatgac acctttgacg aattgaggag caggttgtta   1200
gcgctgacgg gaggcagctt ctacctcgcc tggacctaca atttcctaga ccttcgaggc   1260
ccgggagacc tgcccacctt cttatctgta acccaacatt ggtggtctat tctgatcttc   1320
ctcatttcga ttgccgtctt ctttattccg tcgaggccct cacctagacc cacactcagc   1380
gcctaa                                                              1386
```

<210> SEQ ID NO 131
<211> LENGTH: 1257
<212> TYPE: DNA
<213> ORGANISM: Artificial Sequence
<220> FEATURE:
<223> OTHER INFORMATION: Chimeric squalene synthase consisting of first 1,056 bp of the yeast squalene synthase gene coding for the first 352 amino acids, followed by 201 bp coding for the carboxy terminal 67 amino acids of the Arabidopsis thaliana squalene synthase
<220> FEATURE:
<221> NAME/KEY: misc_binding
<222> LOCATION: (1)..(1257)

<400> SEQUENCE: 131

```
atgggaaagc tattacaatt ggcattgcat ccggtcgaga tgaaggcagc tttgaagctg     60
aagttttgca gaacaccgct attctccatc tatgatcagt ccacgtctcc atatctcttg    120
cactgtttcg aactgttgaa cttgacctcc agatcgtttg ctgctgtgat cagagagctg    180
catccagaat tgagaaactg tgttactctc tttttatttga ttttaagggc tttggatacc    240
atcgaagacg atatgtccat cgaacacgat ttgaaaattg acttgttgcg tcacttccac    300
gagaaattgt tgttaactaa atggagtttc gacggaaatg ccccgatgt gaaggacaga     360 gccgttttga cagatttcga atcgattctt attgaattcc acaaattgaa accagaatat    420
caagaagtca tcaaggagat caccgagaaa atgggtaatg gtatggccga ctacatctta    480
gatgaaaatt acaacttgaa tgggttgcaa accgtccacg actacgacgt gtactgtcac    540
tacgtagctg gttggtcgg tgatggtttg acccgtttga ttgtcattgc caagtttgcc     600
aacgaatctt tgtattctaa tgagcaattg tatgaaagca tgggtctttt cctacaaaaa    660
```

| | |
|---|---|
| accaacatca tcagagatta caatgaagat ttggtcgatg gtagatcctt ctggcccaag | 720 |
| gaaatctggt cacaatacgc tcctcagttg aaggacttca tgaaacctga aaacgaacaa | 780 |
| ctggggttgg actgtataaa ccacctcgtc ttaaacgcat tgagtcatgt tatcgatgtg | 840 |
| ttgacttatt tggccggtat ccacgagcaa tccactttcc aattttgtgc cattccccaa | 900 |
| gttatggcca ttgcaacctt ggctttggta ttcaacaacc gtgaagtgct acatggcaat | 960 |
| gtaaagattc gtaagggtac tacctgctat ttaattttga aatcaaggac tttgcgtggc | 1020 |
| tgtgtcgaga tttttgacta ttacttacgt gatatcaaga caaaggttga caagaacgat | 1080 |
| ccaaatgcca gtaagacact aaaccgactt gaagccgttc agaaactctg cagagacgct | 1140 |
| ggagttcttc aaaacagaaa atcttatgtt aatgacaaag gacaaccaaa cagtgtcttt | 1200 |
| attataatgg ttgtgattct actggccata gtctttgcat atctcagagc aaactga | 1257 |

<210> SEQ ID NO 132
<211> LENGTH: 1311
<212> TYPE: DNA
<213> ORGANISM: Artificial Sequence
<220> FEATURE:
<223> OTHER INFORMATION: Chimeric squalene synthase consisting of first
      1,032 bp of the Arabidopsis squalene synthase gene coding for the
      first 344 amino acids, followed by 276 bp coding for the carboxy
      terminal 92 amino acids of the yeast squalene synthase
<220> FEATURE:
<221> NAME/KEY: misc_binding
<222> LOCATION: (1)..(1311)

<400> SEQUENCE: 132

| | |
|---|---|
| atggggagct tggggacgat gctgagatat ccggatgaca tatatccgct cctgaagatg | 60 |
| aaacgagcga ttgagaaagc ggagaagcag atccctcctg agccacactg gggtttctgc | 120 |
| tattcgatgc tccacaaggt ttctcgaagc ttttctctcg ttattcagca actcaacacc | 180 |
| gagctccgta acgccgtgtg tgtgttctac ttggttctcc gagctcttga tactgttgag | 240 |
| gatgatacta gcataccaac tgatgaaaag gttcccatcc tgatagcttt tcaccggcac | 300 |
| atatacgata ctgattggca ttattcatgt ggtacgaagg agtacaagat tctaatggac | 360 |
| caatttcacc atgtttctgc agcttttttg gaacttgaaa agggtatca agaggctatc | 420 |
| gaggaaatta ctagaagaat gggtgcaggg atggccaagt ttatctgcca agaggtagaa | 480 |
| actgttgatg actacgatga atactgccac tatgttgctg gcttgttgg tttaggtttg | 540 |
| tcgaaactct cctcgctgc aggatcagag ttttgacac cagattggga ggcgatttcc | 600 |
| aattcaatgg gtttatttct gcagaaaaca acattatca gagattatct tgaggacatt | 660 |
| aatgagatac caaaatcccg catgttttgg cctcgcgaga tttggggcaa atatgctgac | 720 |
| aagcttgagg atttaaaata cgaggagaac acaaacaaat ccgtacagtg cttaaatgaa | 780 |
| atggttacca atgcgttgat gcatattgaa gattgcctga atacatggt ttccttgcgt | 840 |
| gatccttcca tatttcggtt ctgtgccatc cctcagatca tggcgattgg aacacttgca | 900 |
| ttatgctata acaatgaaca agtattcaga ggcgttgtga aactgaggcg aggtcttact | 960 |
| gctaaagtca ttgatcgtac aaagacaatg gctgatgtct atggtgcttt ctatgatttt | 1020 |
| tcctgcatgc tgaaatctaa attggctgtg caagatccaa atttcttaaa attgaacatt | 1080 |
| caaatctcca agatcgaaca gtttatggaa gaaatgtacc aggataaatt acctcctaac | 1140 |
| gtgaagccaa atgaaactcc aattttcttg aaagttaaag aaagatccag atacgatgat | 1200 |
| gaattggttc caacccaaca agaagaagag tacaagttca atatggtttt atctatcatc | 1260 |
| ttgtccgttc ttcttgggtt ttattatata tacactttac acagagcgtg a | 1311 |

<210> SEQ ID NO 133
<211> LENGTH: 1266
<212> TYPE: DNA
<213> ORGANISM: Artificial Sequence
<220> FEATURE:
<223> OTHER INFORMATION: Chimeric squalene synthase consisting of 1,062 bp of the yeast squalene synthase gene coding for the first 354 amino acids, followed by 201 bp coding for the carboxy terminal 67 amino acids of the tobacco squalene synthase
<220> FEATURE:
<221> NAME/KEY: misc_binding
<222> LOCATION: (1)..(1266)

<400> SEQUENCE: 133

| | | |
|---|---|---|
| atgggaaagc tattacaatt ggcattgcat ccggtcgaga tgaaggcagc tttgaagctg | 60 |
| aagttttgca gaacaccgct attctccatc tatgatcagt ccacgtctcc atatctcttg | 120 |
| cactgtttcg aactgttgaa cttgacctcc agatcgtttg ctgctgtgat cagagagctg | 180 |
| catccagaat tgagaaactg tgttactctc ttttatttga ttttaagggc tttggatacc | 240 |
| atcgaagacg atatgtccat cgaacacgat ttgaaaattg acttgttgcg tcacttccac | 300 |
| gagaaattgt tgttaactaa atggagtttc gacggaaatg cccccgatgt gaaggacaga | 360 |
| gccgttttga cagatttcga atcgattctt attgaattcc acaaattgaa accagaatat | 420 |
| caagaagtca tcaaggagat caccgagaaa atgggtaatg gtatggccga ctacatctta | 480 |
| gatgaaaatt acaacttgaa tgggttgcaa accgtccacg actacgacgt gtactgtcac | 540 |
| tacgtagctg gtttggtcgg tgatggtttg acccgtttga ttgtcattgc caagtttgcc | 600 |
| aacgaatctt tgtattctaa tgagcaattg tatgaaagca tgggtctttt cctacaaaaa | 660 |
| accaacatca tcagagatta caatgaagat ttggtcgatg gtagatcctt ctggcccaag | 720 |
| gaaatctggt cacaatacgc tcctcagttg aaggacttca tgaaacctga aaacgaacaa | 780 |
| ctggggttgg actgtataaa ccacctcgtc ttaaacgcat tgagtcatgt atcgatgtg | 840 |
| ttgacttatt tggccggtat ccacgagcaa tccactttcc aattttgtgc cattccccaa | 900 |
| gttatggcca ttgcaacctt ggctttggta ttcaacaacc gtgaagtgct acatggcaat | 960 |
| gtaaagattc gtaagggtac tacctgctat ttaattttga aatcaaggac tttgcgtggc | 1020 |
| tgtgtcgaga tttttgacta ttacttacgt gatatcaaat ccaaggttaa taataatgat | 1080 |
| ccaaatgcaa caaaaactct gaagaggctc gaagtgatcc tgaaaacttg cagagattcg | 1140 |
| ggaaccttga caaaaggaa atcctacata atcaggagcg agcctaatta cagtccagtt | 1200 |
| ctgattgttg tcattttcat catactggct attattctcg cacagctatc cggaaaccga | 1260 |
| tcttag | 1266 |

<210> SEQ ID NO 134
<211> LENGTH: 1305
<212> TYPE: DNA
<213> ORGANISM: Artificial Sequence
<220> FEATURE:
<223> OTHER INFORMATION: Chimeric squalene synthase consisting of 1,029 bp of the tobacco squalene synthase gene coding for the first 343 amino acids, followed by 273 bp coding for the carboxy terminal 91 amino acids of the yeast squalene synthase
<220> FEATURE:
<221> NAME/KEY: misc_binding
<222> LOCATION: (1)..(1305)

<400> SEQUENCE: 134
atggggagtt tgagggctat tctgaagaat ccagaggatt tatatccatt ggtgaagctg      60

```
aagctagcgg ctcgacacgc ggagaagcag atcccgccgt ctccaaattg gggcttctgt      120
tactcaatgc ttcataaggt ttctcgtagc tttgctctcg tcattcaaca acttccagtc      180
gagcttcgtg acgccgtgtg cattttctat ttggttcttc gagcacttga cactgttgag      240
gatgatacca gcattcccac cgatgttaaa gttcctattc tgatctcttt tcatcagcat      300
gtttatgatc gcgaatggca ttttcatgt ggtacaaagg agtacaaggt tctcatggac       360
cagttccatc atgtatcaac tgcttttctg gagcttagga acattatca gcaggcaatt       420 gaggatatta ccatgaggat gggtgcagga atggcaaaat tcatatgcaa ggaggtggaa      480
acaaccgatg attatgacga atattgtcac tatgtagctg gcttgttgg gctaggattg       540 tcaaaactgt tccatgcctc tgagaaagaa gatctggctt cagattctct ctccaactcc      600
atgggtttat tcttcagaa acaaacatc attagagatt atttggaaga cataaatgaa        660
gtacccaagt gccgtatgtt ctggccccgt gaaatatgga gtaaatatgt taacaagctt      720
gaggaattaa agtacgagga taactcggcc aaagcagtgc aatgtctaaa tgacatggtc      780
actaatgctt tatcacatgt agaagattgt ttgacttaca tgtctgcttt gcgtgatcct      840
tccatctttc gattctgtgc tattccacag gtcatggcaa ttgggacatt agctatgtgc      900
tacgacaaca ttgaagtctt cagaggagtg gtaaaaatga gacgtggtct gactgctaag      960
gtcattgacc ggaccaggac tattgcagat gtatatggtg cttttttga cttttcttgt       1020 atgctgaaat ctaaattggc tgtgcaagat ccaaatttct taaaattgaa cattcaaatc      1080
tccaagatcg aacagtttat ggaagaaatg taccaggata aattacctcc taacgtgaag      1140
ccaaatgaaa ctccaatttt cttgaaagtt aagaaagat ccagatacga tgatgaattg       1200
gttccaaccc aacaagaaga agagtacaag ttcaatatgg ttttatctat catcttgtcc      1260
gttcttcttg ggttttatta tatatacact ttacacagag cgtga                     1305
```

<210> SEQ ID NO 135
<211> LENGTH: 1377
<212> TYPE: DNA
<213> ORGANISM: Artificial Sequence
<220> FEATURE:
<223> OTHER INFORMATION: Chimeric squalene synthase consisting of 1,056
      bp of the B. braunii squalene synthase gene coding for the first
      352 amino acids, followed by 84 bp encoding for 28 amino acids of
      a linker domain of the yeast squalene synthase, then 234 bp of
      the B.
<220> FEATURE:
<221> NAME/KEY: misc_binding
<222> LOCATION: (1)..(1377)

<400> SEQUENCE: 135

```
atggggatgc ttcgctgggg agtggagtct ttgcagaatc cagatgaatt aatcccggtc       60
ttgaggatga tttatgctga taagtttgga aagatcaagc caaggacga agaccggggc       120 ttctgctatg aaattttaaa ccttgtttca agaagttttg caatcgtcat ccaacagctc      180
cctgcacagc tgagggaccc agtctgcata ttttaccttg tactacgcgc cctgacaca       240 gtcgaagatg atatgaaaat tgcagcaacc accaagattc ccttgctgcg tgacttttat      300
gagaaaattt ctgacaggtc attccgcatg acggccggag atcaaaaaga ctacatcagg      360
ctgttggatc agtaccccaa agtgacaagc gttttcttga aattgacccc ccgtgaacaa      420
gagataattg cagacattac aaagcggatg gggaatggaa tggctgactt cgtgcataag      480 ggtgttccg acacagtggg ggactacgac ctttactgcc actatgttgc tggggtggtg      540
ggtctcgggc tttcccagtt gttcgttgcg agtggactac agtcaccctc tttgacccgc      600
```

```
agtgaagacc tttccaatca catgggcctc ttccttcaga agaccaacat catccgcgac      660
tactttgagg acatcaatga gctgcctgcc ccccggatgt tctggcccag agagatctgg      720
ggcaagtatg cgaacaacct cgctgagttc aaagacccgg ccaacaaggc ggctgcaatg      780
tgctgcctca acgagatggt cacagatgca ttgaggcacg cggtgtactg cctgcagtac      840
atgtccatga ttgaggatcc gcagatcttc aacttctgtg ccatccctca gaccatggcc      900
ttcggcaccc tgtctttgtg ttacaacaac tacactatct tcacagggcc caaagcggct      960
gtgaagctgc gtaggggcac cactgccaag ctgatgtaca cctctaacaa tatgtttgcg     1020
atgtaccgtc atttcctcaa cttcgcgagg aagcttaaat ctaaattggc tgtgcaagat     1080
ccaaatttct taaaattgaa cattcaaatc tccaagatcg aacagtttat ggaagccggc     1140
ctggcacgca caaagatga caccctttgac gaattgagga gcaggttgtt agcgctgacg     1200
ggaggcagct tctacctcgc ctggacctac aatttcctag accttcgagg cccgggagac     1260
ctgcccacct tcttatctgt aacccaacat tggtggtcta ttctgatctt cctcatttcg     1320
attgccgtct tctttattcc gtcgaggccc tcacctagac ccacactcag cgcctaa        1377
```

<210> SEQ ID NO 136
<211> LENGTH: 1344
<212> TYPE: DNA
<213> ORGANISM: Artificial Sequence
<220> FEATURE:
<223> OTHER INFORMATION: Chimeric squalene synthase consisting of 1,056
      bp of the yeast squalene synthase gene coding for the first 352
      amino acids, followed by 87 bp encoding for 29 amino acids of a
      linker domain of the B. braunii squalene synthase, then 201 bp of
      the yeast
<220> FEATURE:
<221> NAME/KEY: misc_binding
<222> LOCATION: (1)..(1344)

<400> SEQUENCE: 136

```
atgggaaagc tattacaatt ggcattgcat ccggtcgaga tgaaggcagc tttgaagctg       60
aagttttgca gaacaccgct attctccatc tatgatcagt ccacgtctcc atatctcttg      120
cactgtttcg aactgttgaa cttgacctcc agatcgtttg ctgctgtgat cagagagctg      180
catccagaat tgagaaactg tgttactctc ttttatttga ttttaagggc tttggatacc      240
atcgaagacg atatgtccat cgaacacgat ttgaaaattg acttgttgcg tcacttccac      300
gagaaattgt tgttaactaa atggagtttc gacggaaatg cccccgatgt gaaggacaga      360
gccgttttga cagatttcga atcgattctt attgaattcc acaaattgaa accagaatat      420
caagaagtca tcaaggagat caccgagaaa atgggtaatg gtatgccga ctacatctta      480 gatgaaaatt acaacttgaa tgggttgcaa accgtccacg actacgacgt gtactgtcac      540
tacgtagctg gtttggtcgg tgatggtttg accgtttga ttgtcattgc caagtttgcc      600
aacgaatctt tgtattctaa tgagcaattg tatgaaagca tgggtctttt cctacaaaaa      660
accaacatca tcagagatta caatgaagat tggtcgatg tagatcctt ctggcccaag      720 gaaatctggt cacaatacgc tcctcagttg aaggacttca tgaaacctga aaacgaacaa      780
ctggggttgg actgtataaa ccacctcgtc ttaaacgcat tgagtcatgt tatcgatgtg      840
ttgacttatt tggccggtat ccacgagcaa tccacttttc cattttgtgc cattccccaa      900
gttatggcca ttgcaaccct tggctttggta ttcaacaacc gtgaagtgct acatggcaat      960
gtaaagattc gtaagggtac tacctgctat ttaattttga aatcaaggac tttgcgtggc     1020
tgtgtcgaga tttttgacta ttacttacgt gatatcgaag tcagatgcaa caccgagacc     1080
```

-continued

```
agcgaggatc ccagcgtgac caccactctg gaacacctgc ataagatcaa agctgcctgc    1140
aaggaaatgt accaggataa attacctcct aacgtgaagc caaatgaaac tccaattttc    1200
ttgaaagtta agaaagatc cagatacgat gatgaattgg ttccaaccca acaagaagaa     1260
gagtacaagt tcaatatggt tttatctatc atcttgtccg ttcttcttgg gttttattat    1320
atatacactt tacacagagc gtga                                           1344
```

<210> SEQ ID NO 137
<211> LENGTH: 1335
<212> TYPE: DNA
<213> ORGANISM: Artificial Sequence
<220> FEATURE:
<223> OTHER INFORMATION: Chimeric squalene synthase consisting of 1,056
      bp of the yeast squalene synthase gene coding for the first 352
      amino acids, followed by 78 bp encoding for 26 amino acids of a
      linker domain of the Arabidopsis squalene synthase, then 201 bp of
      the yeast
<220> FEATURE:
<221> NAME/KEY: misc_binding
<222> LOCATION: (1)..(1335)

<400> SEQUENCE: 137

```
atgggaaagc tattacaatt ggcattgcat ccggtcgaga tgaaggcagc tttgaagctg     60
aagttttgca gaacaccgct attctccatc tatgatcagt ccacgtctcc atatctcttg    120
cactgtttcg aactgttgaa cttgacctcc agatcgtttg ctgctgtgat cagagagctg    180
catccagaat tgagaaactg tgttactctc ttttatttga ttttaagggc tttggatacc    240
atcgaagacg atatgtccat cgaacacgat ttgaaaattg acttgttgcg tcacttccac    300
gagaaattgt tgttaactaa atggagtttc gacggaaatg cccccgatgt gaaggacaga    360
gccgttttga cagatttcga atcgattctt attgaattcc acaaattgaa accagaatat    420
caagaagtca tcaaggagat caccgagaaa atgggtaatg gtatggccga ctacatctta    480
gatgaaaatt acaacttgaa tgggttgcaa accgtccacg actacgacgt gtactgtcac    540
tacgtagctg gtttggtcgg tgatggtttg accgtttga ttgtcattgc caagtttgcc     600
aacgaatctt tgtattctaa tgagcaattg tatgaaagca tgggtctttt cctacaaaaa    660
accaacatca tcagagatta caatgaagat ttggtcgatg tagatccttc tggcccaag    720 gaaatctggt cacaatacgc tcctcagttg aaggacttca tgaaacctga aaacgaacaa    780
ctggggttgg actgtataaa ccacctcgtc ttaaacgcat tgagtcatgt tatcgatgtg    840
ttgacttatt tggccggtat ccacgagcaa tccactttcc aattttgtgc cattccccaa    900
gttatggcca ttgcaacctt ggctttggta ttcaacaacc gtgaagtgct acatggcaat    960
gtaaagattc gtaagggtac tacctgctat ttaattttga atcaaggac tttgcgtggc    1020 tgtgtcgaga ttttttgacta ttacttacgt gatatcaaga caaaggttga caagaacgat    1080
ccaaatgcca gtaagacact aaaccgactt gaagccgttc agaaactctg cagagaaatg    1140
taccaggata aattacctcc taacgtgaag ccaaatgaaa ctccaattt cttgaaagtt    1200 aaagaaagat ccagatacga tgatgaattg gttccaaccc aacaagaaga agagtacaag    1260
ttcaatatgg ttttatctat catcttgtcc gttcttcttg ggttttatta tatatacact    1320
ttacacagag cgtga                                                    1335
```

<210> SEQ ID NO 138
<211> LENGTH: 1233
<212> TYPE: DNA
<213> ORGANISM: Artificial Sequence
<220> FEATURE:

```
<223> OTHER INFORMATION: Chimeric squalene synthase consisting of 1,032
      bp of the Arabidopsis squalene synthase gene coding for the first
      344 amino acids, followed by 78 bp encoding for 26 amino acids of
      a linker domain of the yeast squalene synthase, then 120 bp of the
<220> FEATURE:
<221> NAME/KEY: misc_binding
<222> LOCATION: (1)..(1233)

<400> SEQUENCE: 138
atggggagct tggggacgat gctgagatat cccgatgata tatatccgct cctgaagatg      60
aaacgagcga ttgagaaagc ggagaagcag atccctcctg agccacactg gggtttctgc     120
tattcgatgc tccacaaggt ttctcgaagc ttttctctcg ttattcagca actcaacacc     180
gagctccgta acgccgtgtg tgtgttctac ttggttctcc gagctcttga tactgttgag     240
gatgatacta gcataccaac tgatgaaaag gttcccatcc tgatagcttt tcaccggcac     300
atatacgata ctgattggca ttattcatgt ggtacgaagg agtacaagat tctaatggac     360
caatttcacc atgtttctgc agctttttg gaacttgaaa aagggtatca agaggctatc      420
gaggaaatta ctagaagaat gggtgcaggg atggccaagt ttatctgcca agaggtagaa     480
actgttgatg actacgatga atactgccac tatgttgctg ggcttgttgg tttaggtttg     540
tcgaaactct tcctcgctgc aggatcagag gttttgacac cagattggga ggcgatttcc     600
aattcaatgg gtttatttct acagaaaaca aacattatca gagattatct tgaggacatt     660
aatgagatac caaatcccg catgttttgg cctcgcgaga tttggggcaa atatgctgac     720
aagcttgagg atttaaaata cgaggagaac acaaacaaat ccgtacagtg cttaaatgaa     780
atggttacca atgcgttgat gcatattgaa gattgcctga atacatggt ttccttgcgt      840 gatccttcca tatttcggtt ctgtgccatc cctcagatca tggcgattgg aacacttgca     900
ttatgctata caatgaaca agtattcaga ggcgttgtga aactgaggcg aggtcttact      960
gctaaagtca ttgatcgtac aaagacaatg gctgatgtct atggtgcttt ctatgatttt    1020
tcctgcatgc tgaaatctaa attggctgtg caagatccaa atttcttaaa attgaacatt    1080
caaatctcca agatcgaaca gtttatggaa gacgctggag ttcttcaaaa cagaaaatct    1140
tatgttaatg acaaaggaca accaaacagt gtctttatta taatggttgt gattctactg    1200
gccatagtct ttgcatatct cagagcaaac tga                                 1233

<210> SEQ ID NO 139
<211> LENGTH: 1335
<212> TYPE: DNA
<213> ORGANISM: Artificial Sequence
<220> FEATURE:
<223> OTHER INFORMATION: S. cerevisiae squalene synthase constructs
      cloned into YEp352
<220> FEATURE:
<221> NAME/KEY: misc_binding
<222> LOCATION: (1057)..(1095)

<400> SEQUENCE: 139
atgggaaagc tattacaatt ggcattgcat ccggtcgaga tgaaggcagc tttgaagctg      60
aagttttgca gaacaccgct attctccatc tatgatcagt ccacgtctcc atatctcttg    120
cactgtttcg aactgttgaa cttgaccctcc agatcgtttg ctgctgtgat cagagagctg     180
catccagaat tgagaaactg tgttactctc ttttatttga ttttaagggc tttggatacc     240
atcgaagacg atatgtccat cgaacacgat ttgaaaattg acttgttgcg tcacttccac     300
gagaaattgt tgttaactaa atggagtttc gacggaaatg cccccgatgt gaaggacaga    360
gccgttttga cagatttcga atcgattctt attgaattcc acaaattgaa accagaatat     420
```

```
caagaagtca tcaaggagat caccgagaaa atgggtaatg gtatggccga ctacatctta    480
gatgaaaatt acaacttgaa tgggttgcaa accgtccacg actacgacgt gtactgtcac    540
tacgtagctg gtttggtcgg tgatggtttg acccgtttga ttgtcattgc caagtttgcc    600
aacgaatctt tgtattctaa tgagcaattg tatgaaagca tgggtctttt cctacaaaaa    660
accaacatca tcagagatta caatgaagat ttggtcgatg gtagatcctt ctggcccaag    720
gaaatctggt cacaatacgc tcctcagttg aaggacttca tgaaacctga aaacgaacaa    780
ctggggttgg actgtataaa ccacctcgtc ttaaacgcat tgagtcatgt tatcgatgtg    840
ttgacttatt tggccggtat ccacgagcaa tccactttcc aatttgtgc cattccccaa     900 gttatggcca ttgcaaccct tggctttggt a ttcaacaacc gtgaagtgct acatggcaat   960
gtaaagattc gtaagggtac tacctgctat ttaattttga aatcaaggac tttgcgtggc   1020
tgtgtcgaga ttttttgacta ttacttacgt gatatcaaga caaaggttga caagaacgat   1080
ccaaatgcca gtaagttgaa cattcaaatc tccaagatcg aacagtttat ggaagaaatg   1140
taccaggata aattacctcc taacgtgaag ccaaatgaaa ctccaatttt cttgaaagtt   1200
aaagaaagat ccagatacga tgatgaattg gttccaaccc aacaagaaga agagtacaag   1260
ttcaatatgg ttttatctat catcttgtcc gttcttcttg ggtttta tatatacact      1320 ttacacagag cgtga                                                    1335

<210> SEQ ID NO 140
<211> LENGTH: 1335
<212> TYPE: DNA
<213> ORGANISM: Artificial Sequence
<220> FEATURE:
<223> OTHER INFORMATION: S. cerevisiae squalene synthase constructs
      cloned into YEp353
<220> FEATURE:
<221> NAME/KEY: misc_binding
<222> LOCATION: (1096)..(1134)

<400> SEQUENCE: 140
atgggaaagc tattacaatt ggcattgcat ccggtcgaga tgaaggcagc tttgaagctg    60
aagttttgca gaacaccgct attctccatc tatgatcagt ccacgtctcc atatctcttg   120
cactgtttcg aactgttgaa cttgacctcc agatcgtttg ctgctgtgat cagagagctg   180
catccagaat tgagaaactg tgttactctc tttttatttga ttttaagggc tttggatacc  240
atcgaagacg atatgtccat cgaacacgat ttgaaaattg acttgttgcg tcacttccac   300
gagaaattgt tgttaactaa atggagtttc gacggaaatg cccccgatgt gaaggacaga   360
gccgttttga cagatttcga atcgattctt attgaattcc acaaattgaa accagaatat   420
caagaagtca tcaaggagat caccgagaaa atgggtaatg gtatggccga ctacatctta   480
gatgaaaatt acaacttgaa tgggttgcaa accgtccacg actacgacgt gtactgtcac   540
tacgtagctg gtttggtcgg tgatggtttg acccgtttga ttgtcattgc caagtttgcc   600
aacgaatctt tgtattctaa tgagcaattg tatgaaagca tgggtctttt cctacaaaaa   660
accaacatca tcagagatta caatgaagat ttggtcgatg gtagatcctt ctggcccaag   720
gaaatctggt cacaatacgc tcctcagttg aaggacttca tgaaacctga aaacgaacaa   780
ctggggttgg actgtataaa ccacctcgtc ttaaacgcat tgagtcatgt tatcgatgtg   840
ttgacttatt tggccggtat ccacgagcaa tccactttcc aatttgtgc cattccccaa    900 gttatggcca ttgcaaccct tggctttggt a ttcaacaacc gtgaagtgct acatggcaat  960
```

```
gtaaagattc gtaagggtac tacctgctat ttaattttga aatcaaggac tttgcgtggc   1020
tgtgtcgaga tttttgacta ttacttacgt gatatcaaat ctaaattggc tgtgcaagat   1080

ccaaatttct taaaaacact aaaccgactt gaagccgttc agaaactctg cagagaaatg   1140
taccaggata aattacctcc taacgtgaag ccaaatgaaa ctccaatttt cttgaaagtt   1200
aaagaaagat ccagatacga tgatgaattg gttccaaccc aacaagaaga agagtacaag   1260
ttcaatatgg ttttatctat catcttgtcc gttcttcttg ggttttatta tatatacact   1320
ttacacagag cgtga                                                    1335
```

<210> SEQ ID NO 141
<211> LENGTH: 1335
<212> TYPE: DNA
<213> ORGANISM: Artificial Sequence
<220> FEATURE:
<223> OTHER INFORMATION: S. cerevisiae squalene synthase constructs cloned into YEp354
<220> FEATURE:
<221> NAME/KEY: misc_binding
<222> LOCATION: (1114)..(1125)

<400> SEQUENCE: 141

```
atgggaaagc tattacaatt ggcattgcat ccggtcgaga tgaaggcagc tttgaagctg     60
aagttttgca gaacaccgct attctccatc tatgatcagt ccacgtctcc atatctcttg    120
cactgtttcg aactgttgaa cttgacctcc agatcgtttg ctgctgtgat cagagagctg    180
catccagaat tgagaaactg tgttactctc ttttatttga ttttaagggc tttggatacc    240
atcgaagacg atatgtccat cgaacacgat ttgaaaattg acttgttgcg tcacttccac    300
gagaaattgt tgttaactaa atggagtttc gacggaaatg cccccgatgt gaaggacaga    360
gccgttttga cagatttcga atcgattctt attgaattcc acaaattgaa accagaatat    420
caagaagtca tcaaggagat caccgagaaa atgggtaatg gtatggccga ctacatctta    480
gatgaaaatt acaacttgaa tgggttgcaa accgtccacg actacgacgt gtactgtcac    540
tacgtagctg gtttggtcgg tgatggtttg acccgtttga ttgtcattgc caagtttgcc    600
aacgaatctt tgtattctaa tgagcaattg tatgaaagca tgggtctttt cctacaaaaa    660
accaacatca tcagagatta caatgaagat ttggtcgatg gtagatcctt ctggcccaag    720
gaaatctggt cacaatacgc tcctcagttg aaggacttca tgaaacctga aaacgaacaa    780
ctggggttgg actgtataaa ccacctcgtc ttaaacgcat tgagtcatgt tatcgatgtg    840
ttgacttatt tggccggtat ccacgagcaa tccactttcc aattttgtgc cattccccaa    900
gttatggcca ttgcaacctt ggctttggta ttcaacaacc gtgaagtgct acatggcaat    960
gtaaagattc gtaagggtac tacctgctat ttaattttga aatcaaggac tttgcgtggc   1020
tgtgtcgaga tttttgacta ttacttacgt gatatcaaat ctaaattggc tgtgcaagat   1080
ccaaatttct taaaattgaa cattcaaatc tccgccgttc aaaagtttat ggaagaaatg   1140
taccaggata aattacctcc taacgtgaag ccaaatgaaa ctccaatttt cttgaaagtt   1200
aaagaaagat ccagatacga tgatgaattg gttccaaccc aacaagaaga agagtacaag   1260
ttcaatatgg ttttatctat catcttgtcc gttcttcttg ggttttatta tatatacact   1320
ttacacagag cgtga                                                    1335
```

<210> SEQ ID NO 142
<211> LENGTH: 1335
<212> TYPE: DNA
<213> ORGANISM: Artificial Sequence

```
<220> FEATURE:
<223> OTHER INFORMATION: S. cerevisiae squalene synthase constructs
      cloned into YEp355
<220> FEATURE:
<221> NAME/KEY: misc_binding
<222> LOCATION: (1087)..(1107)

<400> SEQUENCE: 142
atgggaaagc tattacaatt ggcattgcat ccggtcgaga tgaaggcagc tttgaagctg      60
aagttttgca gaacaccgct attctccatc tatgatcagt ccacgtctcc atatctcttg     120
cactgtttcg aactgttgaa cttgacctcc agatcgtttg ctgctgtgat cagagagctg     180
catccagaat tgagaaactg tgttactctc ttttatttga ttttaagggc tttggatacc     240
atcgaagacg atatgtccat cgaacacgat ttgaaaattg acttgttgcg tcacttccac     300
gagaaattgt tgttaactaa atggagtttc gacggaaatg ccccgatgt gaaggacaga      360 gccgttttga cagatttcga atcgattctt attgaattcc acaaattgaa accagaatat     420
caagaagtca tcaaggagat caccgagaaa atgggtaatg gtatggccga ctacatctta     480
gatgaaaatt acaacttgaa tgggttgcaa accgtccacg actacgacgt gtactgtcac     540
tacgtagctg gttggtcgg tgatggtttg acccgtttga ttgtcattgc caagtttgcc      600
aacgaatctt tgtattctaa tgagcaattg tatgaaagca tgggtctttt cctacaaaaa     660
accaacatca tcagagatta caatgaagat ttggtcgatg gtagatcctt ctggcccaag     720
gaaatctggt cacaatacgc tcctcagttg aaggacttca tgaaacctga aaacgaacaa     780
ctggggttgg actgtataaa ccacctcgtc ttaaacgcat tgagtcatgt tatcgatgtg     840
ttgacttatt tggccggtat ccacgagcaa tccactttcc aattttgtgc cattccccaa     900
gttatggcca ttgcaacctt ggctttggta ttcaacaacc gtgaagtgct acatggcaat     960
gtaaagattc gtaagggtac tacctgctat ttaattttga atcaaggac tttgcgtggc     1020 tgtgtcgaga tttttgacta ttacttacgt gatatcaaat ctaaattggc tgtgcaagat    1080
ccaaatgcca gtaagacact aaaccgtatc tccaagatcg aacagtttat ggaagaaatg    1140
taccaggata aattacctcc taacgtgaag ccaaatgaaa ctccaatttt cttgaaagtt    1200
aaagaaagat ccagatacga tgatgaattg gttccaaccc aacaagaaga agtacaag     1260 ttcaatatgg ttttatctat catcttgtcc gttcttcttg ggttttatta tatatacact    1320
ttacacagag cgtga                                                      1335

<210> SEQ ID NO 143
<211> LENGTH: 1335
<212> TYPE: DNA
<213> ORGANISM: Artificial Sequence
<220> FEATURE:
<223> OTHER INFORMATION: S. cerevisiae squalene synthase constructs
      cloned into YEp356
<220> FEATURE:
<221> NAME/KEY: misc_binding
<222> LOCATION: (1087)..(1125)

<400> SEQUENCE: 143
atgggaaagc tattacaatt ggcattgcat ccggtcgaga tgaaggcagc tttgaagctg      60
aagttttgca gaacaccgct attctccatc tatgatcagt ccacgtctcc atatctcttg     120
cactgtttcg aactgttgaa cttgacctcc agatcgtttg ctgctgtgat cagagagctg     180
catccagaat tgagaaactg tgttactctc ttttatttga ttttaagggc tttggatacc     240
atcgaagacg atatgtccat cgaacacgat ttgaaaattg acttgttgcg tcacttccac     300
```

```
gagaaattgt tgttaactaa atggagtttc gacggaaatg cccccgatgt gaaggacaga    360
gccgttttga cagatttcga atcgattctt attgaattcc acaaattgaa accagaatat    420
caagaagtca tcaaggagat caccgagaaa atgggtaatg gtatggccga ctacatctta    480
gatgaaaatt acaacttgaa tggggttgcaa accgtccacg actacgacgt gtactgtcac   540
tacgtagctg gtttggtcgg tgatggtttg acccgtttga ttgtcattgc caagtttgcc    600
aacgaatctt tgtattctaa tgagcaattg tatgaaagca tgggtctttt cctacaaaaa    660
accaacatca tcagagatta caatgaagat ttggtcgatg gtagatcctt ctggcccaag    720
gaaatctggt cacaatacgc tcctcagttg aaggacttca tgaaacctga aaacgaacaa    780
ctggggttgg actgtataaa ccacctcgtc ttaaacgcat tgagtcatgt tatcgatgtg    840
ttgacttatt tggccggtat ccacgagcaa tccactttcc aattttgtgc cattccccaa    900
gttatggcca ttgcaacctt ggctttggta ttcaacaacc gtgaagtgct acatggcaat    960
gtaaagattc gtaagggtac tacctgctat ttaattttga aatcaaggac tttgcgtggc   1020
tgtgtcgaga ttttttgacta ttacttacgt gatatcaaat ctaaattggc tgtgcaagat   1080
ccaaatgcca gtaagacact aaaccgtctt gaagccgttc agaagtttat ggaagaaatg   1140
taccaggata aattacctcc taacgtgaag ccaaatgaaa ctccaatttt cttgaaagtt   1200
aaagaaagat ccagatacga tgatgaattg gttccaaccc aacaagaaga agagtacaag   1260
ttcaatatgg ttttatctat catcttgtcc gttcttcttg ggttttatta tatatacact   1320
ttacacagag cgtga                                                    1335
```

<210> SEQ ID NO 144
<211> LENGTH: 1233
<212> TYPE: DNA
<213> ORGANISM: Artificial Sequence
<220> FEATURE:
<223> OTHER INFORMATION: A. thaliana squalene synthase constructs cloned into YEp357
<220> FEATURE:
<221> NAME/KEY: misc_binding
<222> LOCATION: (1033)..(1071)

<400> SEQUENCE: 144

```
atggggagct tggggacgat gctgagatat cccgatgata tatatccgct cctgaagatg     60
aaacgagcga ttgagaaagc ggagaagcag atccctcctg agccacactg ggtttctgc    120
tattcgatgc tccacaaggt ttctcgaagc ttttctctcg ttattcagca actcaacacc    180
gagctccgta acgccgtgtg tgtgttctac ttggttctcc gagctcttga tactgttgag    240
gatgatacta gcataccaac tgatgaaaag gttcccatcc tgatagcttt tcaccggcac    300
atatacgata ctgattggca ttattcatgt ggtacgaagg agtacaagat tctaatggac    360
caatttcacc atgtttctgc agcttttttg gaacttgaaa aagggtatca agaggctatc    420
gaggaaatta ctagaagaat gggtgcaggg atggccaagt ttatctgcca agaggtagaa    480
actgttgatg actacgatga atactgccac tatgttgctg gcttgttgg tttaggtttg    540
tcgaaactct tcctcgctgc aggatcagag gttttgacac cagattggga ggcgatttcc    600
aattcaatgg gttatttct acagaaaaca acattatca gagattatct tgaggacatt    660
aatgagatac caaaatcccg catgttttgg cctcgcgaga tttggggcaa atatgctgac    720
aagcttgagg atttaaaata cgaggagaac acaaacaaat ccgtacagtg cttaaatgaa    780
atggttacca atgcgttgat gcatattgaa gattgcctga atacatggt tccttgcgt     840
gatccttcca tatttcggtt ctgtgccatc cctcagatca tggcgattgg aacacttgca    900
```

```
ttatgctata acaatgaaca agtattcaga ggcgttgtga aactgaggcg aggtcttact        960
gctaaagtca ttgatcgtac aaagacaatg gctgatgtct atggtgcttt ctatgatttt       1020
tcctgcatgc tgaaatctaa attggctgtg caagatccaa atttcttaaa aacactaaac       1080
cgacttgaag ccgttcagaa actctgcaga gacgctggag ttcttcaaaa cagaaaatct       1140
tatgttaatg acaaaggaca accaaacagt gtctttatta taatggttgt gattctactg       1200
gccatagtct ttgcatatct cagagcaaac tga                                    1233

<210> SEQ ID NO 145
<211> LENGTH: 1233
<212> TYPE: DNA
<213> ORGANISM: Artificial Sequence
<220> FEATURE:
<223> OTHER INFORMATION: A. thaliana squalene synthase constructs cloned
      into YEp358
<220> FEATURE:
<221> NAME/KEY: misc_binding
<222> LOCATION: (1072)..(1110)

<400> SEQUENCE: 145
atggggagct tggggacgat gctgagatat cccgatgata tatatccgct cctgaagatg         60
aaacgagcga ttgagaaagc ggagaagcag atccctcctg agccacactg gggtttctgc        120
tattcgatgc tccacaaggt ttctcgaagc ttttctctcg ttattcagca actcaacacc        180
gagctccgta acgccgtgtg tgtgttctac ttggttctcc gagctcttga tactgttgag        240
gatgatacta gcataccaac tgatgaaaag gttcccatcc tgatagcttt tcaccggcac        300
atatacgata ctgattggca ttattcatgt ggtacgaagg agtacaagat tctaatggac        360
caatttcacc atgtttctgc agcttttttg gaacttgaaa aagggtatca agaggctatc        420
gaggaaatta ctagaagaat gggtgcaggg atggccaagt ttatctgcca agaggtagaa        480
actgttgatg actacgatga atactgccac tatgttgctg gcttgttgg tttaggtttg         540 tcgaaactct tcctcgctgc aggatcagag gttttgacac cagattggga ggcgatttcc        600
aattcaatgg gtttatttct acagaaaaca acattatca gagattatct tgaggacatt        660
aatgagatac caaaatcccg catgttttgg cctcgcgaga tttggggcaa atatgctgac        720
aagcttgagg atttaaaata cgaggagaac acaaacaaat ccgtacagtg cttaaatgaa        780
atggttacca atgcgttgat gcatattgaa gattgcctga atacatggt ttccttgcgt        840 gatccttcca tatttcggtt ctgtgccatc cctcagatca tggcgattgg aacacttgca        900
ttatgctata acaatgaaca agtattcaga ggcgttgtga aactgaggcg aggtcttact        960
gctaaagtca ttgatcgtac aaagacaatg gctgatgtct atggtgcttt ctatgatttt       1020
tcctgcatgc tgaagacaaa ggttgacaag aacgatccaa atgccagtaa gttgaacatt       1080
caaatctcca agatcgaaca gtttatggaa gacgctggag ttcttcaaaa cagaaaatct       1140
tatgttaatg acaaaggaca accaaacagt gtctttatta taatggttgt gattctactg       1200
gccatagtct ttgcatatct cagagcaaac tga                                    1233

<210> SEQ ID NO 146
<211> LENGTH: 1233
<212> TYPE: DNA
<213> ORGANISM: Artificial Sequence
<220> FEATURE:
<223> OTHER INFORMATION: A. thaliana squalene synthase constructs cloned
      into YEp359
<220> FEATURE:
<221> NAME/KEY: misc_binding
```

<222> LOCATION: (1090)..(1101)

<400> SEQUENCE: 146

```
atggggagct tggggacgat gctgagatat cccgatgata tatatccgct cctgaagatg     60
aaacgagcga ttgagaaagc ggagaagcag atccctcctg agccacactg gggtttctgc    120
tattcgatgc tccacaaggt ttctcgaagc ttttctctcg ttattcagca actcaacacc    180
gagctccgta acgccgtgtg tgtgttctac ttggttctcc gagctcttga tactgttgag    240
gatgatacta gcataccaac tgatgaaaag gttcccatcc tgatagcttt tcaccggcac    300
atatacgata ctgattggca ttattcatgt ggtacgaagg agtacaagat tctaatggac    360
caatttcacc atgtttctgc agcttttttg aacttgaaa aagggtatca agaggctatc    420
gaggaaatta ctagaagaat gggtgcaggg atggccaagt ttatctgcca agaggtagaa    480
actgttgatg actacgatga atactgccac tatgttgctg ggcttgttgg tttaggtttg    540
tcgaaactct cctcgctgc aggatcagag gttttgacac cagattggga ggcgatttcc    600
aattcaatgg gtttatttct acagaaaaca aacattatca gagattatct tgaggacatt    660
aatgagatac caaaatcccg catgttttgg cctcgcgaga tttggggcaa atatgctgac    720
aagcttgagg atttaaaata cgaggagaac acaaacaaat ccgtacagtg cttaaatgaa    780
atggttacca atgcgttgat gcatattgaa gattgcctga atacatggt ttccttgcgt    840
gatccttcca tatttcggtt ctgtgccatc cctcagatca tggcgattgg aacacttgca    900
ttatgctata caatgaaca agtattcaga ggcgttgtga aactgaggcg aggtcttact    960
gctaaagtca ttgatcgtac aaagacaatg gctgatgtct atggtgcttt ctatgatttt   1020
tcctgcatgc tgaagacaaa ggttgacaag aacgatccaa atgccagtaa gacactaaac   1080
cgacttgaaa agatcgaaca gctctgcaga gacgctggag ttcttcaaaa cagaaaatct   1140
tatgttaatg acaaaggaca accaaacagt gtctttatta taatggttgt gattctactg   1200
gccatagtct ttgcatatct cagagcaaac tga                                 1233
```

<210> SEQ ID NO 147
<211> LENGTH: 1233
<212> TYPE: DNA
<213> ORGANISM: Artificial Sequence
<220> FEATURE:
<223> OTHER INFORMATION: A. thaliana squalene synthase constructs cloned into YEp360
<220> FEATURE:
<221> NAME/KEY: misc_binding
<222> LOCATION: (1063)..(1083)

<400> SEQUENCE: 147

```
atggggagct tggggacgat gctgagatat cccgatgata tatatccgct cctgaagatg     60
aaacgagcga ttgagaaagc ggagaagcag atccctcctg agccacactg gggtttctgc    120
tattcgatgc tccacaaggt ttctcgaagc ttttctctcg ttattcagca actcaacacc    180
gagctccgta acgccgtgtg tgtgttctac ttggttctcc gagctcttga tactgttgag    240
gatgatacta gcataccaac tgatgaaaag gttcccatcc tgatagcttt tcaccggcac    300
atatacgata ctgattggca ttattcatgt ggtacgaagg agtacaagat tctaatggac    360
caatttcacc atgtttctgc agcttttttg aacttgaaa aagggtatca agaggctatc    420
gaggaaatta ctagaagaat gggtgcaggg atggccaagt ttatctgcca agaggtagaa    480
actgttgatg actacgatga atactgccac tatgttgctg ggcttgttgg tttaggtttg    540
tcgaaactct cctcgctgc aggatcagag gttttgacac cagattggga ggcgatttcc    600
```

```
aattcaatgg gtttatttct acagaaaaca aacattatca gagattatct tgaggacatt    660
aatgagatac caaaatcccg catgtttgg cctcgcgaga tttggggcaa atatgctgac    720
aagcttgagg atttaaaata cgaggagaac acaaacaaat ccgtacagtg cttaaatgaa    780
atggttacca atgcgttgat gcatattgaa gattgcctga atacatggt ttccttgcgt    840 gatccttcca tatttcggtt ctgtgccatc cctcagatca tggcgattgg aacacttgca    900
ttatgctata acaatgaaca agtattcaga ggcgttgtga aactgaggcg aggtcttact    960
gctaaagtca ttgatcgtac aaagacaatg gctgatgtct atggtgcttt ctatgatttt   1020
tcctgcatgc tgaagacaaa ggttgacaag aacgatccaa atttcttaaa attgaacatt   1080
caacttgaag ccgttcagaa actctgcaga gacgctggag ttcttcaaaa cagaaaatct   1140
tatgttaatg acaaaggaca accaaacagt gtctttatta taatggttgt gattctactg   1200
gccatagtct ttgcatatct cagagcaaac tga                                 1233
```

<210> SEQ ID NO 148
<211> LENGTH: 1233
<212> TYPE: DNA
<213> ORGANISM: Artificial Sequence
<220> FEATURE:
<223> OTHER INFORMATION: A. thaliana squalene synthase constructs cloned into YEp361
<220> FEATURE:
<221> NAME/KEY: misc_binding
<222> LOCATION: (1063)..(1101)

<400> SEQUENCE: 148

```
atggggagct tggggacgat gctgagatat cccgatgata tatatccgct cctgaagatg     60
aaacgagcga ttgagaaagc ggagaagcag atccctcctg agccacactg gggtttctgc    120
tattcgatgc tccacaaggt ttctcgaagc tttttctctcg ttattcagca actcaacacc    180
gagctccgta acgccgtgtg tgtgttctac ttggttctcc gagctcttga tactgttgag    240
gatgatacta gcataccaac tgatgaaaag gttcccatcc tgatagcttt tcaccggcac    300
atatacgata ctgattggca ttattcatgt ggtacgaagg agtacaagat tctaatggac    360
caatttcacc atgtttctgc agctttttttg gaacttgaaa aagggtatca agaggctatc    420
gaggaaatta ctagaagaat gggtgcaggg atggccaagt ttatctgcca agaggtagaa    480
actgttgatg actacgatga atactgccac tatgttgctg gcttgttgg tttaggtttg    540 tcgaaactct cctcgctgc aggatcagag gttttgacac cagattggga ggcgatttcc    600
aattcaatgg gtttatttct acagaaaaca aacattatca gagattatct tgaggacatt    660
aatgagatac caaaatcccg catgtttgg cctcgcgaga tttggggcaa atatgctgac    720
aagcttgagg atttaaaata cgaggagaac acaaacaaat ccgtacagtg cttaaatgaa    780
atggttacca atgcgttgat gcatattgaa gattgcctga atacatggt ttccttgcgt    840 gatccttcca tatttcggtt ctgtgccatc cctcagatca tggcgattgg aacacttgca    900
ttatgctata acaatgaaca agtattcaga ggcgttgtga aactgaggcg aggtcttact    960
gctaaagtca ttgatcgtac aaagacaatg gctgatgtct atggtgcttt ctatgatttt   1020
tcctgcatgc tgaagacaaa ggttgacaag aacgatccaa atttcttaaa attgaacatt   1080
caaatctcca agatcgaaca gctctgcaga gacgctggag ttcttcaaaa cagaaaatct   1140
tatgttaatg acaaaggaca accaaacagt gtctttatta taatggttgt gattctactg   1200
gccatagtct ttgcatatct cagagcaaac tga                                 1233
```

<210> SEQ ID NO 149
<211> LENGTH: 282
<212> TYPE: DNA
<213> ORGANISM: Artificial Sequence
<220> FEATURE:
<223> OTHER INFORMATION: C-terminus S. cerevisiae squalene synthase
      construct
<220> FEATURE:
<221> NAME/KEY: misc_binding
<222> LOCATION: (4)..(282)

<400> SEQUENCE: 149

```
atgaaatcta aattggctgt gcaagatcca aatttcttaa aattgaacat tcaaatctcc      60
aagatcgaac agtttatgga agaaatgtac caggataaat acctcctaa cgtgaagcca     120 aatgaaactc caattttctt gaaagttaaa gaaagatcca gatacgatga tgaattggtt     180
ccaacccaac aagaagaaga gtacaagttc aatatggttt tatctatcat cttgtccgtt     240
cttcttgggt tttattatat atacacttta cacagagcgt ga                       282
```

<210> SEQ ID NO 150
<211> LENGTH: 198
<212> TYPE: DNA
<213> ORGANISM: Artificial Sequence
<220> FEATURE:
<223> OTHER INFORMATION: C-terminus S. cerevisiae squalene synthase
      construct
<220> FEATURE:
<221> NAME/KEY: misc_binding
<222> LOCATION: (4)..(198)

<400> SEQUENCE: 150

```
atgtaccagg ataaattacc tcctaacgtg aagccaaatg aaactccaat tttcttgaaa      60
gttaaagaaa gatccagata cgatgatgaa ttggttccaa cccaacaaga agaagagtac     120
aagttcaata tggttttatc tatcatcttg tccgttcttc ttgggtttta ttatatatac     180
actttacaca gagcgtga                                                  198
```

<210> SEQ ID NO 151
<211> LENGTH: 204
<212> TYPE: DNA
<213> ORGANISM: Artificial Sequence
<220> FEATURE:
<223> OTHER INFORMATION: C-terminus A. thaliana squalene synthase
      construct
<220> FEATURE:
<221> NAME/KEY: misc_binding
<222> LOCATION: (4)..(204)

<400> SEQUENCE: 151

```
atgaagacaa aggttgacaa gaacgatcca aatgccagta agacactaaa ccgacttgaa      60
gccgttcaga aactctgcag agacgctgga gttcttcaaa acagaaaatc ttatgttaat     120
gacaaaggac aaccaaacag tgtctttatt ataatggttg tgattctact ggccatagtc     180
tttgcatatc tcagagcaaa ctga                                           204
```

<210> SEQ ID NO 152
<211> LENGTH: 204
<212> TYPE: DNA
<213> ORGANISM: Artificial Sequence
<220> FEATURE:
<223> OTHER INFORMATION: C-terminus S. cerevisiae and A. thaliana
      squalene synthase construct
<220> FEATURE:
<221> NAME/KEY: misc_binding
<222> LOCATION: (4)..(204)

```
<400> SEQUENCE: 152
atgaaatcta aattggctgt gcaagatcca aatttcttaa aattgaacat tcaaatctcc      60
aagatcgaac agtttatgga agacgctgga gttcttcaaa acagaaaatc ttatgttaat     120
gacaaaggac aaccaaacag tgtctttatt ataatggttg tgattctact ggccatagtc     180
tttgcatatc tcagagcaaa ctga                                           204

<210> SEQ ID NO 153
<211> LENGTH: 282
<212> TYPE: DNA
<213> ORGANISM: Artificial Sequence
<220> FEATURE:
<223> OTHER INFORMATION: C-terminus A. thaliana and S. cerevisiae
      squalene synthase construct
<220> FEATURE:
<221> NAME/KEY: misc_binding
<222> LOCATION: (4)..(282)

<400> SEQUENCE: 153
atgaagacaa aggttgacaa gaacgatcca aatgccagta agacactaaa ccgacttgaa      60
gccgttcaga aactctgcag agaaatgtac caggataaat acctcctaa cgtgaagcca     120 aatgaaactc caatttctct tgaaagttaaa gaaagatcca gatacgatga tgaattggtt    180
ccaacccaac aagaagaaga gtacaagttc aatatggttt tatctatcat cttgtccgtt    240
cttcttgggt tttattatat atacacttta cacagagcgt ga                       282

<210> SEQ ID NO 154
<211> LENGTH: 291
<212> TYPE: DNA
<213> ORGANISM: Artificial Sequence
<220> FEATURE:
<223> OTHER INFORMATION: C-terminus B. braunii and S. cerevisiae
      squalene synthase construct
<220> FEATURE:
<221> NAME/KEY: misc_binding
<222> LOCATION: (4)..(291)

<400> SEQUENCE: 154
atggaagtca gatgcaacac cgagaccagc gaggatccca gcgtgaccac cactctggaa      60
cacctgcata agatcaaagc tgcctgcaag gaaatgtacc aggataaatt acctcctaac    120
gtgaagccaa atgaaactcc aatttttctg aaagttaaag aaagatccag atacgatgat    180
gaattggttc caacccaaca agaagaagag tacaagttca atatggtttt atctatcatc    240
ttgtccgttc ttcttgggtt ttattatata tacactttac acagagcgtg a             291

<210> SEQ ID NO 155
<211> LENGTH: 324
<212> TYPE: DNA
<213> ORGANISM: Artificial Sequence
<220> FEATURE:
<223> OTHER INFORMATION: C-terminus S. cerevisiae and B. braunii
      squalene synthase construct
<220> FEATURE:
<221> NAME/KEY: misc_binding
<222> LOCATION: (4)..(324)

<400> SEQUENCE: 155
atgaaatcta aattggctgt gcaagatcca aatttcttaa aattgaacat tcaaatctcc      60
aagatcgaac agtttatgga agccggcctg cacgcacaa agatgacac ctttgacgaa     120 ttgaggagca ggttgttagc gctgacggga ggcagcttct acctcgcctg gacctacaat    180
```

```
ttcctagacc ttcgaggccc gggagacctg cccaccttct tatctgtaac ccaacattgg    240
tggtctattc tgatcttcct catttcgatt gccgtcttct ttattccgtc gaggccctca    300
cctagaccca cactcagcgc ctaa                                            324

<210> SEQ ID NO 156
<211> LENGTH: 282
<212> TYPE: DNA
<213> ORGANISM: Artificial Sequence
<220> FEATURE:
<223> OTHER INFORMATION: Fusion of Aspergillus squalene synthase - yeast
      squalene synthase
<220> FEATURE:
<221> NAME/KEY: misc_binding
<222> LOCATION: (4)..(81)

<400> SEQUENCE: 156
atgcacaaga agaacacacc caaggacccc aatttcctaa aaatcagtat cgtctgcggc     60
aagattgaga aatttatcga ggaaatgtac caggataaat acctcctaa cgtgaagcca    120 aatgaaactc caatttttctt gaaagttaaa gaaagatcca gatacgatga tgaattggtt    180
ccaacccaac aagaagaaga gtacaagttc aatatggttt tatctatcat cttgtccgtt    240
cttcttgggt tttattatat atacacttta cacagagcgt ga                      282

<210> SEQ ID NO 157
<211> LENGTH: 2073
<212> TYPE: DNA
<213> ORGANISM: Artificial Sequence
<220> FEATURE:
<223> OTHER INFORMATION: Fluorescence protein tagged S. cerevisiae
      squalene synthase construct
<220> FEATURE:
<221> NAME/KEY: misc_binding
<222> LOCATION: (715)..(738)

<400> SEQUENCE: 157
atgtctaaag gtgaagaatt attcactggt gttgtcccaa ttttggttga attagatggt     60
gatgttaatg gtcacaaatt ttctgtctcc ggtgaaggtg aaggtgatgc tacttacggt    120
aaattgaccc taaaatttat ttgtactact ggtaaattgc cagttccatg gccaacctta    180
gtcactactt tcggttatgg tgttcaatgt tttgcgagat acccagatca tatgaaacaa    240
catgactttt tcaagtctgc catgccagaa ggttatgttc aagaaagaac tatttttttc    300
aaagatgacg gtaactacaa gaccagagct gaagtcaagt ttgaaggtga taccttagtt    360
aatagaatcg aattaaaagg tattgatttt aagaagatg gtaacatttt aggtcacaaa    420
ttggaataca actataactc tcacaatgtt tacatcatgg ctgacaaaca aaagaatggt    480
atcaaagtta acttcaaaat tagacacaac attgaagatg gttctgttca attagctgac    540
cattatcaac aaaatactcc aattggtgat ggtccagtct tgttaccaga caaccattac    600
ttatccactc aatctgcctt atccaaagat ccaaacgaaa agacagacca catggtcttg    660
ttagaatttg ttactgctgc tggtattacc catggtatgg atgaattgta caaggtggt    720 tctggtggtg gttctggtat gggaaagcta ttacaattgg cattgcatcc ggtcgagatg    780
aaggcagctt tgaagctgaa gttttgcaga acaccgctat tctccatcta tgatcagtcc    840
acgtctccat atctcttgca ctgtttcgaa ctgttgaact tgacctccag atcgtttgct    900
gctgtgatca gagagctgca tccagaattg agaaactgtg ttactctctt ttatttgatt    960
ttaagggctt tggataccat cgaagacgat atgtccatcg aacacgattt gaaaattgac   1020
ttgttgcgtc acttccacga gaaattgttg ttaactaaat ggagtttcga cggaaatgcc   1080
```

```
cccgatgtga aggacagagc cgttttgaca gatttcgaat cgattcttat tgaattccac    1140
aaattgaaac cagaatatca agaagtcatc aaggagatca ccgagaaaat gggtaatggt    1200
atggccgact acatcttaga tgaaaattac aacttgaatg ggttgcaaac cgtccacgac    1260
tacgacgtgt actgtcacta cgtagctggt ttggtcggtg atggtttgac ccgtttgatt    1320
gtcattgcca agtttgccaa cgaatctttg tattctaatg agcaattgta tgaaagcatg    1380
ggtcttttcc tacaaaaaac caacatcatc agagattaca atgaagattt ggtcgatggt    1440
agatccttct ggcccaagga atctggtca caatacgctc ctcagttgaa ggacttcatg    1500
aaacctgaaa acgaacaact ggggttggac tgtataaacc acctcgtctt aaacgcattg    1560
agtcatgtta tcgatgtgtt gacttatttg gccggtatcc acgagcaatc cactttccaa    1620
ttttgtgcca ttccccaagt tatggccatt gcaaccttgg ctttggtatt caacaaccgt    1680
gaagtgctac atggcaatgt aaagattcgt aagggtacta cctgctattt aatttttgaaa   1740 tcaaggactt tgcgtggctg tgtcgagatt tttgactatt acttacgtga tatcaaatct    1800
aaattggctg tgcaagatcc aaatttctta aaattgaaca ttcaaatctc caagatcgaa    1860
cagtttatgg aagaaaatgta ccaggataaa ttacctccta acgtgaagcc aaatgaaact    1920
ccaattttct tgaaagttaa agaaagatcc agatacgatg atgaattggt tccaacccaa    1980
caagaagaag agtacaagtt caatatggtt ttatctatca tcttgtccgt tcttcttggg    2040
ttttattata tatacacttt acacagagcg tga                                 2073

<210> SEQ ID NO 158
<211> LENGTH: 2088
<212> TYPE: DNA
<213> ORGANISM: Artificial Sequence
<220> FEATURE:
<223> OTHER INFORMATION: Fluorescence protein tagged B. braunii squalene
      synthase construct
<220> FEATURE:
<221> NAME/KEY: misc_binding
<222> LOCATION: (679)..(702)

<400> SEQUENCE: 158
atggtgcgct cctccaagaa cgtcatcaag gagttcatgc gcttcaaggt gcgcatggag      60
ggcaccgtga acggccacga gttcgagatc gagggcgagg gcgagggccg cccctacgag     120
ggccacaaca ccgtgaagct gaaggtgacc aagggcggcc ccctgccctt cgcctgggac     180
atcctgtccc cccagttcca gtacggctcc aaggtgtacg tgaagcaccc cgccgacatc     240
cccgactaca agagctgtc cttccccgag ggcttcaagt gggagcgcgt gatgaacttc     300
gaggacggcg gcgtggtgac cgtgacccaa gactcctccc tgcaggacgg ctgcttcatc     360
tacaaggtga agttcatcgg cgtgaacttc ccctccgacg gccccgtaat gcagaagaag     420
accatgggct gggaggcctc caccgagcgc ctgtaccccc gcgacggcgt gctgaagggc     480
gagatccaca ggcccctgaa gctgaaggac ggcggccact acctggtgga gttcaagtcc     540
atctacatgg ccaagaagcc cgtgcagctg cccggctact actacgtgga ctccaagctg     600
gacatcacct cccacaacga ggactacacc atcgtggagc agtacgagcg caccgagggc     660
cgccaccacc tgttcctggg tggttctggt ggtggttctg gtatgggat gcttcgctgg     720 ggagtggagt cttttgcagaa tccagatgaa ttaatcccgg tcttgaggat gatttatgct     780
gataagtttg gaaagatcaa gccaaaggac gaagaccggg gcttctgcta tgaaatttta     840
aaccttgttt caagaagttt tgcaatcgtc atccaacagc tccctgcaca gctgagggac     900
```

```
ccagtctgca tattttacct tgtactacgc gccctggaca cagtcgaaga tgatatgaaa    960
attgcagcaa ccaccaagat tcccttgctg cgtgactttt atgagaaaat ttctgacagg   1020
tcattccgca tgacggccgg agatcaaaaa gactacatca ggctgttgga tcagtacccc   1080
aaagtgacaa gcgttttctt gaaattgacc ccccgtgaac aagagataat tgcagacatt   1140
acaaagcgga tggggaatgg aatggctgac ttcgtgcata agggtgttcc cgacacagtg   1200
ggggactacg acctttactg ccactatgtt gctggggtgg tgggtctcgg gctttcccag   1260
ttgttcgttg cgagtggact acagtcaccc tctttgaccc gcagtgaaga cctttccaat   1320
cacatgggcc tcttccttca gaagaccaac atcatccgcg actactttga ggacatcaat   1380
gagctgcctg ccccccggat gttctggccc agagagatct ggggcaagta tgcgaacaac   1440
ctcgctgagt tcaaagaccc ggccaacaag gcggctgcaa tgtgctgcct caacgagatg   1500
gtcacagatg cattgaggca cgcggtgtac tgcctgcagt acatgtccat gattgaggat   1560
ccgcagatct tcaacttctg tgccatccct cagaccatgg ccttcggcac cctgtctttg   1620
tgttacaaca actacactat cttcacaggg cccaaagcgg ctgtgaagct gcgtaggggc   1680
accactgcca agctgatgta cacctctaac aatatgtttg cgatgtaccg tcatttcctc   1740
aacttcgcag agaagctgga agtcagatgc aacaccgaga ccagcgagga tcccagcgtg   1800
accaccactc tggaacacct gcataagatc aaagctgcct gcaaggctgg gctggcacgc   1860
acaaaagatg acacctttga cgaattgagg agcaggttgt tagcgctgac gggaggcagc   1920
ttctacctcg cctggaccta caatttccta gaccttcgag gcccgggaga cctgcccacc   1980
ttcttatctg taacccaaca ttggtggtct attctgatct tcctcatttc gattgccgtc   2040
ttctttattc cgtcgaggcc ctcacctaga cccacactca gcgcctaa                2088
```

<210> SEQ ID NO 159
<211> LENGTH: 2115
<212> TYPE: DNA
<213> ORGANISM: Artificial Sequence
<220> FEATURE:
<223> OTHER INFORMATION: Fluorescence protein tagged B. braunii squalene synthase construct
<220> FEATURE:
<221> NAME/KEY: misc_binding
<222> LOCATION: (715)..(738)
<220> FEATURE:
<221> NAME/KEY: misc_binding
<222> LOCATION: (1795)..(1872)

<400> SEQUENCE: 159

```
atgtctaaag gtgaagaatt attcactggt gttgtcccaa ttttggttga attagatggt     60
gatgttaatg gtcacaaatt ttctgtctcc ggtgaaggtg aaggtgatgc tacttacggt    120
aaattgacct aaaatttat ttgtactact ggtaaattgc cagttccatg gccaaccttg     180
gtcactactt tcggttatgg tgttcaatgt tttgcgagat acccagatca tatgaaacaa    240
catgactttt tcaagtctgc catgccagaa ggttatgttc aagaaagaac tattttttc     300 aaagatgacg gtaactacaa gaccagagct gaagtcaagt ttgaaggtga taccttagtt    360
aatagaatcg aattaaaagg tattgatttt aagaagatg gtaacatttt aggtcacaaa    420
ttggaataca actataactc tcacaatgtt tacatcatgg ctgacaaaca aaagaatggt    480
atcaaagtta acttcaaaat tagacacaac attgaagatg gttctgttca attagctgac    540
cattatcaac aaaatactcc aattggtgat ggtccagtct tgttaccaga caaccattac    600
ttatccactc aatctgcctt atccaaagat ccaaacgaaa agacagacca catggtcttg    660
```

```
ttagaatttg ttactgctgc tggtattacc catggtatgg atgaattgta caaaggtggt    720
tctggtggtg gttctggtat ggggatgctt cgctggggag tggagtcttt gcagaatcca    780
gatgaattaa tcccggtctt gaggatgatt tatgctgata agtttggaaa gatcaagcca    840
aaggacgaag accggggctt ctgctatgaa attttaaacc ttgtttcaag aagttttgca    900
atcgtcatcc aacagctccc tgcacagctg agggacccag tctgcatatt ttaccttgta    960
ctacgcgccc tggacacagt cgaagatgat atgaaaattg cagcaaccac caagattccc   1020
ttgctgcgtg acttttatga aaaatttct gacaggtcat ccgcatgac ggccggagat     1080
caaaaagact acatcaggct gttggatcag taccccaaag tgacaagcgt tttcttgaaa   1140
ttgaccccccc gtgaacaaga gataattgca gacattacaa agcggatggg gaatggaatg   1200
gctgacttcg tgcataaggg tgttcccgac acagtggggg actacgacct ttactgccac   1260
tatgttgctg gggtggtggg tctcgggctt tcccagttgt tcgttgcgag tggactacag   1320
tcaccctctt tgacccgcag tgaagacctt tccaatcaca tgggcctctt ccttcagaag   1380
accaacatca tccgcgacta ctttgaggac atcaatgagc tgcctgcccc ccggatgttc   1440
tggcccagag agatctgggg caagtatgcg aacaacctcg ctgagttcaa agacccggcc   1500
aacaaggcgg ctgcaatgtg ctgcctcaac gagatggtca cagatgcatt gaggcacgcg   1560
gtgtactgcc tgcagtacat gtccatgatt gaggatccgc agatcttcaa cttctgtgcc   1620
atccctcaga ccatggcctt cggcaccctg tctttgtgtt acaacaacta cactatcttc   1680
acagggccca agcggctgt gaagctgcgt aggggcacca ctgccaagct gatgtacacc   1740
tctaacaata tgtttgcgat gtaccgtcat ttcctcaact tcgcagagaa gcttaaatct   1800
aaattggctg tgcaagatcc aaatttctta aaattgaaca ttcaaatctc caagatcgaa   1860
cagtttatgg aagccggcct ggcacgcaca aaagatgaca cctttgacga attgaggagc   1920
aggttgttag cgctgacggg aggcagcttc tacctcgcct ggacctacaa tttcctagac   1980
cttcgaggcc cggagacct gcccaccttc ttatctgtaa cccaacattg gtggtctatt    2040
ctgatcttcc tcatttcgat tgccgtcttc tttattccgt cgaggccctc acctagaccc   2100
acactcagcg cctaa                                                    2115
```

<210> SEQ ID NO 160
<211> LENGTH: 26
<212> TYPE: PRT
<213> ORGANISM: Trypanosoma cruzi

<400> SEQUENCE: 160

Ala Ala Arg Met Asn Ala Gln Asp Ala Cys Tyr Asp Arg Ile Glu His
1               5                   10                  15

Leu Val Asn Asp Ala Ile Arg Ala Met Glu
            20                  25

<210> SEQ ID NO 161
<211> LENGTH: 26
<212> TYPE: PRT
<213> ORGANISM: Leishmania donovani

<400> SEQUENCE: 161

Gln Lys Lys Leu Asp Val Gln Asp Ala Ser Ser Thr Ser Ile Ala Asn
1               5                   10                  15

Ser Leu Ala Ala Ala Ile Glu Arg Ile Asp
            20                  25

COMPOUNDS AND METHOD OF USE AS ANTI-INFECTION COMPOUNDS AND THERAPEUTIC AGENTS TO REGULATE CHOLESTEROL METABOLISM

CROSS-REFERENCE TO RELATED APPLICATION

This application claims the benefit of U.S. Provisional Patent Application No. 61/814,067, filed Apr. 19, 2013, herein incorporated by reference.

FIELD OF THE INVENTION

The presently disclosed subject matter relates to novel compounds and methods and systems for unique infection control reagents and new therapeutics. In one example, the presently disclosed subject matter related to novel compounds and methods and systems for unique ergosterol control reagents, new therapeutics to regulate sterol metabolism in humans and plants, and herbicide compositions. The novel compounds include a functional domain from squalene synthases, e.g. from *S. cerevisiae*, such as a 26 amino acid linker-domain. Alternatively, the compounds can include a portion that mimic the 26 amino acid linker-domain. These compounds can be formulated into anti-fungal compounds. The present invention also relates to therapeutic agents for controlling cholesterol metabolism and ergosterol metabolism in non-fungal organisms based on the aforementioned and other novel compounds which include a peptide sequence from a linker domain of squalene synthase (e.g. the 26 amino acid) linker-domain from *S. cerevisiae* or sequences which mimics the domain. Some of the therapeutic agents may be herbicides.

BACKGROUND OF THE INVENTION

The first squalene synthase (SS) gene to be functionally characterized was isolated from *Saccharomyces cerevisiae* and cloned concurrently by the Karst and Robinson groups (1,2). Both groups utilized the strategy of screening *S. cerevisiae* genomic library clones for their ability to functionally complement a squalene synthase (erg9)-deficient yeast line. Interestingly, Jennings, et al. (2) found that a genomic clone containing only a partial SS gene fragment was able to restore ergosterol prototrophy even though it only restored 5% of the normal level of SS enzyme activity. This finding suggested that low levels of SS enzyme activity were sufficient to complement the erg9 deficiency in yeast. Soon afterwards, Robinson, et al. (3) attempted to clone the SS gene from *Homo sapiens* and *S. pombe* using the same strategy, but isolated only the *S. pombe* gene by screening for complementation of the er9-deficient line (3). Having two SS genes from two species of fungi, these investigators were able to identify conserved regions within the deduced protein sequences to which they designed degenerate primers and cloned the human SS homolog using PCR (3). Robinson, et al. (3) confirmed that the human squalene synthase gene was unable to restore ergosterol prototrophy to the erg9-deficient yeast line, but a chimera SS gene constructed by combining a 5' region of the human gene containing the putative catalytic domain with a 3' region of the *S. cerevisiae* gene containing a membrane-anchoring domain was able to complement the erg9 deficiency. Robinson, et al. (3) suggested that the inability of human SS to functionally complement the erg9-deficient yeast line was due to problems with expression or stability of the human protein in *S. cerevisiae*. A few years later, Soltis, et al. (4) isolated a similar allele of the human squalene synthase gene by screening a human cDNA library with a rat squalene synthase gene probe. These investigators also determined that the human squalene synthase gene was not able to complement an erg9 deficiency in yeast. They were, however, able to document expression of the human squalene synthase gene in yeast by recording the corresponding protein by immuno-blotting methodology, as well as measuring inducible enhancement of SS enzyme activity. This result conflicted with the notion that a heterologously expressed SS was not able to complement the erg9 deficiency in yeast because of problems with transgene expression or protein stability in yeast, and Soltis, et al. (4) hypothesized that structural differences in the carboxy-termini of the yeast and human SS may affect localization or folding of the proteins in association with intracellular membranes.

The first plant SS was cloned from *Arabidopsis* (5) and soon after from *Nicotiana benthamiana* (6). Nakashima, et al. (5) failed to isolate an *Arabidopsis* SS gene by screening for complementation of an erg9 deficient yeast line, and instead screened plaques of an *Arabidopsis* cDNA library with a mouse squalene synthase cDNA probe. Hanley, et al. (6) used a degenerate primer/PCR approach to isolate a *N. benthamiana* SS, and likewise noted that the tobacco SS gene was unable to restore growth when expressed in an erg9 deficient yeast strain. Later, Kribii et al. (7) reported that the *Arabidopsis* genome contained two highly homologous SS genes organized in a tandem array. This group confirmed that the *Arabidopsis* SS could not complement the erg9 (SS gene) disruption in yeast, but they measured significant SS enzyme activity in the microsomal fraction of these yeast. These investigators went on to show that a chimeric *Arabidopsis* SS gene containing a substitution corresponding to the 66 carboxy-terminal amino acids of *Arabidopsis* SS with 111 carboxy-terminal amino acids of the *S. pombe* SS were sufficient to restore prototrophic growth of the erg9 knockout in yeast without exogenous sterol. Radiolabeling studies were also performed with [$^3$H]-FPP fed to microsomes isolated from yeast expressing either the full length *Arabidopsis* SS or the *Arabidopsis-S. pombe* chimera SS genes, or from wild type yeast. Radiolabel was incorporated by either the wild type yeast microsomes or microsomes from the erg9-deficient yeast over-expressing the *Arabidopsis-S. pombe* chimera SS into squalene, squalene-2,3-epoxide, and lanosterol. However, when [$^3$H]-FPP was incubated with microsomes from erg9 deficient yeast expressing the full length *Arabidopsis* SS, only radiolabeled squalene was detected. No SS enzyme activity was detectable in the cytosolic (soluble) fractions of these yeast lines. These results strongly suggested that active SS was being expressed and targeted to membrane in all the constructs tested; however, the carboxy-terminal 111 amino acids of *S. pombe* were necessary for channeling of squalene into the ergosterol biosynthetic pathway (7).

In 2000, another fungal squalene synthase was isolated from *Yarrowia lipolytica* using a degenerate primer approach (8). The *Y. lipolytica* SS was found to complement an erg9 deficient yeast line, albeit the complemented yeast grew slower than the yeast complemented with the *S. cerevisiae* SS gene. Altogether, this result and those of the other investigators demonstrated that at least three different fungal SS could complement the erg9 knockout in *S. cerevisiae*, but no other SS isolated from animal or plant could accomplish this task.

In 2008, Busquets, et al. (9) reported that of the two annotated SS genomic sequences in *Arabidopsis*, only one coded for a functional SS enzyme. Busquets, et al. also performed some fluorescence microscopy experiments to determine the intracellular location of *Arabidopsis* SS (9). GFP was tagged to the N-terminus of a full length SS, a SS lacking the equivalent of the carboxy-terminal 67 amino acids, or the GFP was fused directly to a gene fragment corresponding to that encoding for the carboxy-terminal 67 amino acids of the SS. All three constructs were transiently co-expressed in onion epidermal cells with an ER-targeted version of DsRed. Both the GFP linked to the full length SS and the carboxy-terminal 67 amino acids of SS co-localized with DsRed, which indicated that these two SS enzymes were localized to the ER membrane. The GFP-SS fusion lacking the carboxy-terminal 67 amino acids appeared localized to only the cytosol. These authors concluded that the membrane-spanning region at the carboxy-terminus of SS was critical for correct targeting of SS to the ER membrane (9).

These results and the present inventors' observations that the algal *Botryococcus braunii* SS also could not complement the erg9 mutant in yeast suggested that it was not simply targeting of squalene synthase enzyme activity to the ER membrane of yeast that was important. Some additional protein domain within the carboxy-terminal region of the yeast squalene synthase was necessary to facilitate the complementation phenotype.

BRIEF DESCRIPTION OF THE DRAWINGS

FIG. 1 illustrates various full length and carboxy-terminally truncated squalene synthase genes expressed in yeast line CALI7-1 to test for their ability to complement an erg9 deletion. Terminal truncations are indicated by a lack of gray shading in the linear boxed enzyme model with the specific amino acid coordinates labeled above each. The squalene synthases tested are those of *S. cerevisiae* (YSS), *B. braunii* (BSS), *R. norvegicus* (RSS), *N. benthamiana* (TSS), and *A. thaliana* (ASS). For the erg9 complementation tests, three independent CALI7-1 transformants of each construct were randomly selected and grown in 2 mL Yeast Synthetic Drop-out media (Sigma) containing 5 mg/L ergosterol at 28° C. for three days, after which the culture was serially diluted with water to optical densities (600 nm) equal to 1, 0.2, 0.04, and 0.008, and 5 μL of each dilution spotted onto Yeast Synthetic Drop-out media plates without any exogenous ergosterol. Plates were incubated at 28° C. for 72 hours. Liquid cultures of each construct were also transformed into TN-7 (CALI7-1 containing an additional mutation to knock-out the squalene epoxidase gene, hence the genotype of TN-7 is erg9, erg1) were grown in 10 mL of Yeast Synthetic Drop-out media containing 5 mg/L ergosterol at room temperature for seven days. Organic extracts were prepared and analyzed by GC-MS for their squalene content. To validate each gene construct, the squalene synthase enzyme activity encoded by each gene was assessed when the gene was expressed in Cali7-1 yeast. Briefly, 2,000×g supernatants were prepared and used in enzyme assays containing 3H-FPP and radiolabeled products separated by TLC and analyzed. Enzyme activity (pmoles/h/μg total protein) is recorded as a percent of squalene synthase activity measured when the YSS gene was expressed in the yeast line. (n=3).

FIG. 2 shows the carboxy-terminal amino acids of YSS are necessary and sufficient when appended to heterologous squalene synthase genes to confer ergosterol prototrophic growth to an erg9 knockout yeast line. Constructs were created by reciprocal swapping of the DNA sequences coding for the 91 carboxy-terminal amino acids of YSS with the corresponding DNA segments of the algal (BSS, *Botryococcus* squalene synthase) and plant (ASS and TSS, *Arabidopsis* and tobacco squalene synthase) genes. An additional 24 amino acid truncation of the YSS carboxy domain is indicated by a lack of color in the linear enzyme model. Each construct is annotated with the specific amino acids labeled above each depiction. Constructs were independently transformed into a yeast erg9 knockout line, and three independent transformants for each construct were randomly selected for growth in Yeast Synthetic Drop-out media containing 5 mg/l ergosterol. After three days, each culture was serially diluted with water to OD600=1, 0.2, 0.04, and 0.008, and 5 μl of each dilution spotted on Yeast Synthetic Drop-out media plates lacking ergosterol. Plates were incubated at 28° C. for 72 h. Liquid cultures of each transformant in TN-7 line were grown in 10 mL of Yeast Synthetic Drop-out media containing 5 mg/L ergosterol at room temperature for seven days. Organic extracts were prepared and analyzed by GC-MS for their squalene content. To validate each gene construct, the squalene synthase enzyme activity encoded by each gene was assessed when the gene was expressed in Cali-7 yeast. Briefly, 2000×g supernatants were prepared and used in enzyme assays containing 3H-FPP and radiolabeled products separated by TLC and analyzed. Enzyme activity (pmoles/h/μg total protein) is recorded as a percent of squalene synthase activity measured when the YSS gene was expressed in the yeast line. (n=3).

FIG. 5 shows evaluating the contribution of a carboxy-terminal sequence of 26 amino acids conserved amongst fungi to the complementation and restoration of ergosterol prototrophy to an erg9 knockout yeast line. Full-length *S. cerevisiae* and *Arabidopsis* squalene synthase genes were constructed in which the indicated amino acids corresponding to residues 353 to 378 of YSS and residues 345 to 370 of ASS were exchanged with one another in either the YSS gene (mutants a-e) or the ASS gene (mutants f-j) (in lighter gray, ASS amino acids substituted into the YSS gene; in darker gray, YSS residues substituted into the ASS gene). Each construct was independently transformed into the Cali7-1 erg9 mutant line, 3 independent transformants were randomly selected and grown in Yeast Synthetic Drop-out media (Sigma) containing 5 mg/l ergosterol for 3 days. Aliquots of each culture were then diluted with water to optical densities (600 nm) corresponding to 1, 0.2, 0.04, and 0.008, and 5 µl of each dilution spotted on Yeast Synthetic Drop-out media plates lacking ergosterol. Plates were incubated at 28° C. for 72 h. Liquid cultures of each transformant in TN-7 line were grown in 10 mL of Yeast Synthetic Drop-out media containing 5 mg/L ergosterol at room temperature for seven days. Organic extracts were prepared and analyzed by GC-MS for their squalene content. To validate each gene construct, the squalene synthase enzyme activity encoded by each gene was assessed when the gene was expressed Cali-7 yeast. Briefly, 2000×g supernatants were prepared and used in enzyme assays containing 3H-FPP and radiolabeled products separated by TLC and analyzed. Enzyme activity (pmoles/h/µg total protein) is recorded as a percent of squalene synthase activity measured when the YSS gene was expressed in the yeast line. n=3.

SUMMARY OF THE INVENTION

Figure 3:
FIG. 3 shows the amino acid alignment of the *B. braunii* (AF205791), *C. reinhardtii* (XM_001703395), *A. thaliana* (NM_119630), *N. benthamiana* (U46000.1), *H. sapien* (NM_004462), and *R. norvegicus* (NM_019238) squalene synthases relative to those for *S. cerevisiae* (X59959), *S. pombe* (NM_001021271), and *Y. lipolytica* (AF092497) (Bottom Portion, B) as SEQ ID NOS: 13-24. The alignment is limited to the sequences corresponding to the 67 amino acid domain of the *S. cerevisiae* squalene synthase that are necessary and sufficient to restore ergosterol prototrophy to erg9 deficient yeast. The region boxed and identified as the truncated/conserved/linker-domain region corresponds to a stretch of 26 amino acids (SEQ ID NOS.: 1-12, respectively) that appear more conserved than other regions, and particularly well conserved amongst the fungal squalene synthase's (Top portion, A) of SEQ ID NOS: 13-24, respectively.

The present invention relates to a compound consisting essentially of at least a portion of an amino acid linker-domain for squalene synthase, e.g. squalene synthase from *S. cerevisiae*. In one specific form, the compound includes a 26 amino acid linker-domain, e.g. an amino acid domain having a sequence of SEQ ID NO: 1. Alternatively, the linker domain can have a different sequence from other species having similar, conserved regions, including sequences of SEQ ID NOS: 2-12.

The present invention, in another form, relates to the use of novel compounds which include or mimic the functional amino acid linker-domain from squalene synthase (SEQ ID NO: 1) including but not limited to an amino acid sequence of SEQ ID NOS: 1-12 as a new class of compounds, such as anti-infection agents, herbicides, etc., as provided by this disclosure.

In addition, in one form or embodiment, the present invention relates to new therapeutic agents and methods for controlling cholesterol metabolism in humans using the aforementioned compounds.

In yet an additional embodiment the present invention, a method is provided for treating or controlling sterol biosynthesis by administering or applying a compound comprising at least a portion of an amino acid linker-domain from squalene synthase or a compound which mimics the physical and chemical properties of this compound, to a subject, in need of treatment, therefrom.

The present invention is based on prior studies in which squalene synthase (erg9) deficient *S. cerevisiae* can be complemented by the squalene synthase genes of various fungi, but not those of plants or animals. However, the specific mechanism behind this phenomenon has remained enigmatic. The present invention is further based on identifying a stretch of 26 amino acids which is highly conserved among fungal squalene synthases that does not affect catalytic activity of the enzyme yet is necessary and sufficient to allow squalene synthase genes from any kingdom to complement erg9 mutants of *S. cerevisiae*. Within this 26 amino acid domain, a stretch of four residues is almost completely conserved among fungi, and when changed, the yeast enzyme loses its ability to complement. These results provide evidence that this domain is required for squalene synthase to channel squalene into the sterol synthesis pathway. Overexpression of the non-catalytic C-terminal residues of squalene synthase in *S. cerevisiae* prevents yeast growth, but only when the fungal 26 amino acid linker-domain is included. This confirms the importance of this domain in substrate channeling and provides evidence that molecules that mimic this domain as a new class of anti-fungal compounds, as well can be used new therapeutic agents for the control of cholesterol metabolism in humans. Further, due to the conservation of the amino acid linker-domain in squalene synthase fungal species, the linker-domain in the other fungal species can be used as a substitute for that of the 26 amino acid linker-domain, in various embodiments of the present invention.

DESCRIPTION OF EXEMPLARY EMBODIMENTS

Various embodiments of the present invention are based on the inventor's discovery that specific portions of a full length polypeptide/amino acid sequence for squalene synthase can complement a erg9 mutation in yeast. In particular, it was discovered that an amino acid linker-domain from squalene synthase can complement the erg9 mutation, to restore squalene synthase activity. Based on this, compounds were created which comprise the amino acid linker-domain from squalene synthase. These compounds include peptides which have the sequences of the linker-domain from naturally occurring organisms and can include those which mimic the function and structure of the linker-domain.

In other embodiments, a method for treating or controlling cholesterol metabolism in humans includes administering a therapeutically effective amount of a compound comprising at least a portion of an amino acid linker-domain from squalene synthase, to a patient in need of treatment, therefrom.

In other embodiments, a method is provided for treating or controlling sterol biosynthesis by administering or applying a compound comprising at least a portion of an amino acid linker-domain from squalene synthase, to a subject, in need of treatment, therefrom.

The present invention is based on specific examples and experiments conducted as will be described below. Based on those experiments and examples described below, the present Inventors discovered novel compounds that either include an amino acid linker-domain of squalene synthase from *S. cerevisiae* or have domains or characteristics that mimic the amino acid linker-domain including but not limited to the 26 amino acid linker sequence of SEQ ID NO: 1 as well as SEQ ID NOS: 2-12. For example, one of ordinary skill in the art based on the present disclosure will be able to identify other amino acid sequences which have the desired physical and chemical properties to that of compounds which include SEQ ID NO: 1. Further, the work reported here describes the inventors' efforts to use the erg9 complementation test in yeast to map a specific peptide domain within the carboxy-terminal region of the yeast squalene synthase protein necessary for the complementation phenotype.

Based on the experiments and results described below the aforementioned compounds can be used or formulated into anti-infection compounds such as antifungal compounds, anti-parasitic compounds and herbicides. Further, the aforementioned compounds can be formulated as therapeutic agents to control cholesterol metabolism in humans. In addition, in accordance with the present disclosure, the aforementioned compounds can be used in various methods as antifungal compounds, anti-parasitic compounds and in therapeutic treatments to control cholesterol metabolism, ergosterol biosynthesis in fungi and other organisms dependent on ergosterol for viability.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

In some embodiments of the presently-disclosed subject matter, pharmaceutical compositions comprise a portion of an amino acid linker domain from squalene synthase. The pharmaceutical composition may be included with a pharmaceutically-acceptable vehicle, carrier, or excipient. In some embodiments, the pharmaceutical composition is pharmaceutically-acceptable in humans. Also, as described further below, in some embodiments, the pharmaceutical composition can be formulated as a therapeutic composition for delivery to a subject.

A pharmaceutical composition as described herein preferably comprises a composition that includes a pharmaceutical carrier such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

The compositions can further be formulated as topical semi-sold ointment or cream formulations can contain a concentration of the presently-described compositions in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic. In some embodiments, such ointment or cream formulations can be used for trans-dermal delivery of the pharmaceutical compositions described herein or for delivery to certain organs.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, compositions comprising the amino acid linker domain of squalene synthase or compounds which mimic this domain of the presently-disclosed subject matter can also be formulated as rectal compositions, such as suppositories or retention enemas, e.g., containing conventional suppository bases such as cocoa butter or other glycerides. Further, the present compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

For administration of a therapeutic composition as disclosed herein (e.g., a composition comprising an amino acid linker-domain from squalene synthase), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m2.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered orally, intravenously, or intraperitoneally to thereby treat a disease or disorder, as described herein below.

Regardless of the route of administration, the compositions of the presently-disclosed subject matter typically not only include an effective amount of a therapeutic agent, but are typically administered in amount effective to achieve the desired response. As such, the term "effective amount" is used herein to refer to an amount of the therapeutic composition sufficient to produce a measurable biological response. Actual dosage levels of active ingredients in a therapeutic composition of the presently-disclosed subject matter can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

Yet further provided, in some embodiments, are methods for treating infections including fungal and non-fungal infections, e.g. parasitic infections. Examples of parasitic infections treated include trypanosomatid infections such as those caused by *trypanosoma cruzi* (Tc) and *Leishmania donovani* (Ld). Tc and Ld have similar squalene synthase linker-domains (TcSS and LdSS, respectively) to that for *S. cerevisiae* (ScSS) as shown in the table below:

| | Linker-Domain Sequence | SEQ ID NO: |
|---|---|---|
| ScSS | KSKLAVQDPNFLKLNIQISKIEQFME | 1 |
| TcSS | AARMNAQDACYDRIEHLVNDAIRAME | 160 |
| LdSS | QKKLDVQDASSTSIANSLAAAIERID | 161 |

Since Tc and Ld have similar squalene synthase linker-domain sequences to the squalene synthase linker-domain sequence in *S. cerevisiae* (as well as other organisms identified in this disclosure, including FIG. 3, below), anti-infection agents can be formulated from compounds having at least a portion of an amino acid linker-domain from squalene synthase. These formulated compounds can administered or applied to treat infections, which include fungal and parasitic infections. The squalene synthase can have an amino acid sequence of SEQ ID NOS: 1-12 and/or can have a different sequence that mimics the physical and chemical properties of SEQ ID NOS: 1-12. The treatment can comprise administering a therapeutically effective amount of a compound comprising at least a portion of an amino acid linker-domain from squalene synthase or one that mimics its physical and chemical properties, to a subject or patient in need of treatment, therefrom.

Still further provided, in some embodiments, are methods for treating or controlling cholesterol metabolism in humans by administering a therapeutically effective amount of a compound comprising at least a portion of an amino acid linker-domain from squalene synthase, to a patient in need of treatment, therefrom. In some embodiments, a method for treating or controlling cholesterol metabolism in humans comprises administering to a subject in need thereof an effective amount of a compound comprising a polypeptide having a sequence of SEQ ID NOS: 1-12 or a polypeptide which mimics its physical and chemical properties and function.

It will be appreciated that the function of the linker-domain includes being able to complement an erg9 mutation in yeast. Further function includes restoring, in part, squalene synthases activity in erg9 mutant yeast. Accordingly, a compound consisting essentially of a least a portion of an amino acid linker-domain from squalene, in accordance with some embodiments of the presently-disclosed subject matter will be the compound having the aforementioned linker-domain and any other portion or modification that does not materially affect the function of the compound.

As used herein, the terms "treatment" or "treating" relate to any treatment of a condition of interest (e.g. controlling cholesterol metabolism), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

As used herein, the term "subject" includes human, animal and plant subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

EXPERIMENTS AND EXAMPLES

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The following results of experiments and examples provide evidence of efficacy and generation of the aforementioned compounds and therapeutic treatments. These experiments and examples are intended to be non-limiting, and illustrate only certain embodiments of the present invention. Furthermore, the examples and experiments may include compilations of data that are representative of data gathered at various times during the course of development and experimentation related to the presently-disclosed subject matter.

Complementing the erg9 knockout mutation in yeast requires more than active squalene synthase enzyme activity and squalene accumulation. The following discussion describes the process used to develop a complementing compound to restore squalene synthase actively in erg9 knockout mutation yeast and thereby lead to novel compounds, e.g. proteins/peptides.

Various squalene synthases were cloned into the yeast expression vector, Yep352-ADH1, including those from *S. cerevisiae* (YSS), *B. braunii* (BSS), *N. benthamiana* (TSS), *A. thaliana* (ASS), and *R. norvegicus* (RSS), as well as a C-terminal truncated form of YSS in which 24 amino acids comprising the ER membrane-spanning region were eliminated (YSStr). These constructs were transformed into the yeast line CALI7-1, which has been selected for high level FPP biosynthesis (10) and has an erg9 knockout mutation. It is unable to synthesize sterols de novo and is dependent on exogenous ergosterol for growth. To test if introducing the various squalene synthases could restore ergosterol prototrophy to CALI7-1 yeast line, colonies testing positive for the respective SS transgene by PCR screens were grown in selection media containing ergosterol and serial dilutions were spotted on plates not containing exogenous ergosterol (FIG. 1). To evaluate the encoded enzymes for catalytic activity, extracts prepared from the CALI7-1 yeast lines were assayed for squalene synthase enzyme activity. Constructs were also expressed in TN-7 yeast line and cultures were grown in liquid media with ergosterol and subsequently analyzed for squalene accumulation. Squalene levels were determined in TN-7 because in this yeast line, there is no possibility of squalene feeding into the ergosterol biosynthetic pathway. This allows for accurate comparisons of squalene production by the various SS enzymes.

Interestingly, only the full-length YSS gene and a carboxy-terminal truncated form (deletion of the terminal 24 amino acids) could restore ergosterol prototrophy to the Cali7-1 yeast line. Further, significant squalene accumulation and SS enzyme activity was observed in all squalene synthase constructs tested, providing evidence that the enzyme was properly expressed in an active form in all cases (FIG. 1). This provides evidence that all SS enzymes tested properly expressed in vivo, but only YSS could complement the erg9 deficient CALI7-1 yeast line.

The terminal membrane-spanning domain of squalene synthase is not necessary for functional enzyme nor complementation of the erg9 mutant.

To corroborate and extend the earlier observations of Kirbii et al (7) that a non-catalytic, carboxy-terminal domain was important for complementation, reciprocal molecular swaps of the terminal 100 or so amino acids of various plant and algae SS enzymes were created with that corresponding to the 91 carboxy-terminal amino acids from *S. cerevisiae* SS and tested each for its ability to complement the erg9 mutation in yeast line CALI7-1 (FIG. 2). As expected, all the constructs that contained the carboxy-terminus of *S. cerevisiae* SS were able to complement the erg9 knockout mutation in Cali7-1, while none of the *S. cerevisiae* SS enzymes that had their carboxy-terminus replaced with that of a plant or algae SS displayed ergosterol prototrophy.

Of equal interest is the observation that constructs containing a deletion of the terminal 24 amino acids of the yeast SS (YSStr, FIG. 1) or appending this modified terminal domain to the algal SS (BSS-YSStr, FIG. 2) did not alter the ability of these gene constructs to complement the erg9 deletion. On the basis of hydropathy plots of this region of the SS enzymes (3), this terminal region has been referred to as a membrane-spanning domain and by inference the domain mediating tethering of the SS enzyme activity to the ER membrane system in eukaryotic cells (3). Regardless of these inferences, the YSStr and BSS-YSStr constructs shown in FIGS. 1 and 2 encode for functionally soluble SS enzyme activity (enzyme activity found in 20,000 g supernatants of E. coli expressing this genes) and these constructs complemented the erg9 mutation in yeast equally well as the full-length gene constructs. Hence, the carboxy-terminal 24 amino acids of the yeast SS are not necessary for the complementation phenotype, but some other element(s) within the proximal 67 amino acids of the carboxy-terminus appears to be both necessary and sufficient for complementation.

Computational screens for possible carboxy terminal domains responsible for the complementation phenotype.

Because squalene synthase genes from S. cerevisiae (this disclosure), S. pombe (3), and Y. lipolytica (8) have been demonstrated to complement the erg9 knockout in yeast, but squalene synthases from plant, algae and animals cannot, and because the results in FIGS. 1 and 2 pointed to a proximal carboxy terminal region of 67 amino acids being responsible for the specificity of this complementation, amino acid sequence comparisons of this region between relevant squalene synthases were performed. No over-arching sequence similarities were observed when comparing the sequences across this region from algae, plants, animals and fungi, although there were greater similarities within the first 26 amino acids of this region (FIG. 3, bottom portion "B"). This degree of similarity became much more apparent when the alignments of only the fungal squalene synthase were compared (FIG. 3, top portion "A"). Within this short segment of amino acids, 8 residues are absolutely conserved and the degree of amino acid similarity across the entire 26 amino acids reaches upwards of 45%.

Figure 4:
FIG. 4 shows functional assessment of the role a 26 amino acid peptide sequence within fungal squalene synthases plays in facilitating the complementation of the erg9 mutant. Reciprocal constructs were created by swapping the indicated 26 amino acids of the yeast squalene synthase (YSS) for the corresponding amino acids of an algal squalene synthase (BSS) and a higher plant squalene synthase (ASS). Three independent Cali-7 transformants for each construct were randomly selected, grown in Yeast Synthetic Drop-out media (Sigma) containing 5 mg/l ergosterol for three days, after which serial dilutions were prepared corresponding to optical densities at 600 nm equivalent to 1, 0.2, 0.04, and 0.008, and 5 μl of each dilution spotted onto Yeast Synthetic Drop-out media plates lacking ergosterol. Plates were incubated at 28° C. for 72 h. Liquid cultures of each transformant in TN-7 line were grown in 10 mL of Yeast Synthetic Drop-out media containing 5 mg/L ergosterol at room temperature for seven days. Organic extracts were prepared and analyzed by GC-MS for their squalene content. To validate each gene construct, the squalene synthase enzyme activity encoded by each gene was assessed when the gene was expressed Cali-7 yeast. Briefly, 2000×g supernatants were prepared and used in enzyme assays containing 3H-FPP and radiolabeled products separated by TLC and analyzed. Enzyme activity (pmoles/h/µg total protein) is recorded as a percent of squalene synthase activity measured when the YSS gene was expressed in the yeast line. n=3

To functionally evaluate the contribution of this domain to the complementation phenotype, reciprocal constructs where these 26 amino acids of YSS were exchanged with the corresponding amino acids regions within the BSS and ASS were generated. These constructs were transformed into the erg9 knockout yeast line, and 3 independent colonies from each transformation were screened for their ability to grow in the absence of ergosterol (FIG. 4). When the carboxy-terminal 26 amino acid sequence from S. cerevisae was substituted into the algal (BSS-YSS-BSS), complementation was readily apparent. When the carboxy-terminal 26 amino acid sequence from S. cerevisae was substituted into the Arabidopsis backbone (ASS-YSS-ASS), complementation was restored but the growth rate was noticeably affected. Further analysis revealed that squalene accumulation in this yeast line was only about 5% that of the wild type YSS. Further, squalene synthase enzyme activity in this yeast line was only 7.6% the level as the YSS-expressing yeast line. This provides evidence that the ASS-YSS-ASS was compromised in its squalene synthase enzyme activity, but was still able to complement the erg9 knockout. The reciprocal substitutions of inserting the algal or plant amino acid sequences into the corresponding site of the S. cerevisiae SS resulted in a loss of its ability to complement the erg9 knockout mutations. The loss of this complementation capability was not due to a loss in the catalytic activity of the yeast SS. When these lines were grown in the presence of ergosterol, greater levels of squalene accumulated in these cultures relative to those lines transformed with the wild type YSS construct or other erg9 complementing constructs and SS enzyme activity could be readily measured in yeast lysates.

Mapping the specific amino acids contributing to the complementation phenotype.

To further assess the contribution of individual amino acids within this key stretch of 26 amino acids, fine mapping substitution series constructs were generated (FIG. 5). First, mutants were created in which either the first half (13 residues) or the second half of the 26 amino acid domain was swapped from the A. thaliana SS into the S. cerevisiae backbone (FIG. 5, mutants a and b). Swapping out the first 13 amino acids of the S. cerevisiae SS (FIG. 5, mutant a) had no effect on the ability of the subsequent construct to complement the erg9 mutation, but swapping the second half resulted in a complete loss of the complementation phenotype (FIG. 5, mutant b). Swapping out the first 13 amino acids of A. thaliana SS with those in S. cerevisiae also had no effect on the ability of this construct to complement the erg9 mutant (FIG. 5, mutant f). However, exchanging the second half of these residues with those of the yeast squalene synthase enabled the construct to restore partial growth to the erg9 mutant (FIG. 5, mutant g). Thus, it appeared that the residues in the second half of the 26-amino acid domain were largely responsible for complementation phenotype and this stretch of amino acids was evaluated further.

Because the KIEQ (SEQ ID NO: 35) and FLKLNIQ (SEQ ID NO: 36) stretches of amino acids seem particularly conserved amongst the fungal squalene synthases, various combinations of these peptide domains were exchanged between the ASS and YSS constructs (FIG. 5, mutants c-e and h-j). When the "FLKLNIQ" (SEQ ID NO: 36) stretch of YSS was replaced with the corresponding domain of ASS (FIG. 5, mutant d), complementation growth was not affected, and likewise the reciprocal swap in ASS (FIG. 5, mutant i) did not restore complementation. However, when the "KIEQ" (SEQ ID NO: 35) stretch of YSS was replaced with the corresponding domain of ASS (FIG. 5, mutant c), growth of the yeast was significantly impaired, suggesting that complementation had been affected. The reciprocal swap in ASS (FIG. 5, mutant h) did not restore growth of the erg9 mutant. Two additional mutants in which the entire domains spanning from "FLKLNIQ" (SEQ ID NO: 36) to "KIEQ" (SEQ ID NO: 35) were exchanged (FIG. 5, mutant e and j) were also evaluated for their ability to complement the erg9 mutation. Consistent with our expectations from the other mutants, substituting the yeast amino acids of this domain with those from the Arabidopsis squalene synthase resulted in a complete lose in the ability of this construct to complete the erg9 mutation. However, unexpectedly, substitution of this domain in the Arabidopsis squalene synthase gene with that of the yeast squalene synthase only restored a very modest level of growth to mutant yeast in the complementation tests. All constructs tested in FIG. 5, when expressed in yeast, accumulated higher levels of squalene and had SS enzyme activity in excess of yeast expressing YSS.

The membrane spanning, carboxy-terminal sequence is responsible for localizing squalene synthase to a common membrane system.

Figure 6:
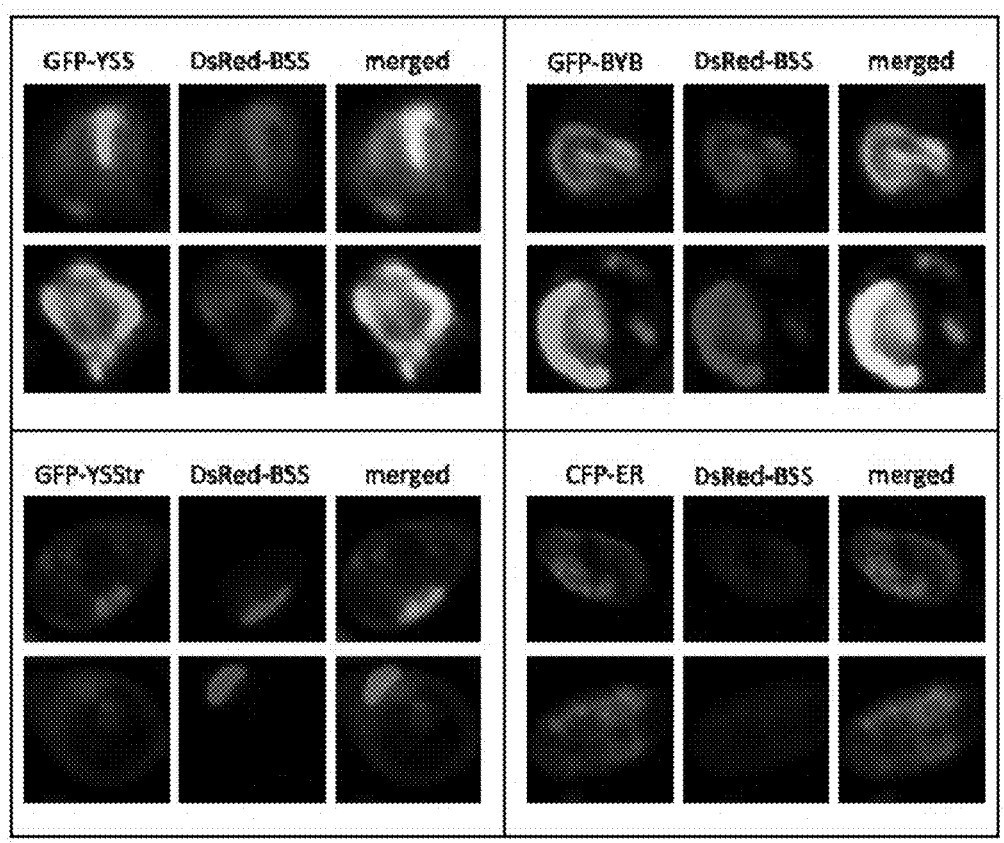
FIG. 6 shows confocal microscopy images of Cali-7 yeast expressing various fluorescent tagged squalene synthase enzymes. Constructs were created by fusing efGFP or DsRed1 in frame and connected by a (GSGG)2 linker to the amino terminus of YSS, BSS-YSS-BSS (BYB), and YSStr, or BSS, respectively. These constructs were cloned into standard yeast expression vectors, Yep352-Ura or pESC-Leu. Various combinations of fluorescent-tagged squalene synthases or a CFP-tagged ER marker (12) were transformed into Cali-7 yeast and positive transformants were grown in Yeast-synthetic Drop-out media containing 5 mg/L ergosterol for three days. Confocal laser scanning micrographs were acquired on an Olympus FV1000 microscope (Olympus America Inc., Melville, N.Y.).

One possible explanation for the uniqueness of the carboxy-terminal domains would be that the plant carboxy termini would target the squalene synthase enzyme to a different intracellular compartment than the yeast carboxy terminus. To evaluate this possibility, DNA coding for different fluorescent tags were appended to the 5' end of the yeast, plant or chimera squalene synthase gene and these were co-expressed in yeast. The subsequent transformants were then subjected to confocal microscopy to visualize the intracellular distribution of each protein. If the yeast squalene synthase carboxy terminus were to direct proteins to a local different from the plant carboxy terminus, then superimposition of the fluorescent images would not be expected to overlap and distinct red and green colors would be visible. Instead, co-localization should result in over-lapping images and color blending (green over-lapping with red) would yield a yellow image. FIG. 6 represents, in gray scale, rather than color (red/green), that the latter indeed occurs, providing strong evidence that the significance of the 26 amino acid linker domain is not to provide a distinct cellular localization signal.

Over-expression of the 26 amino acid linker domain serves to inhibit fungal growth.

Figure 7:
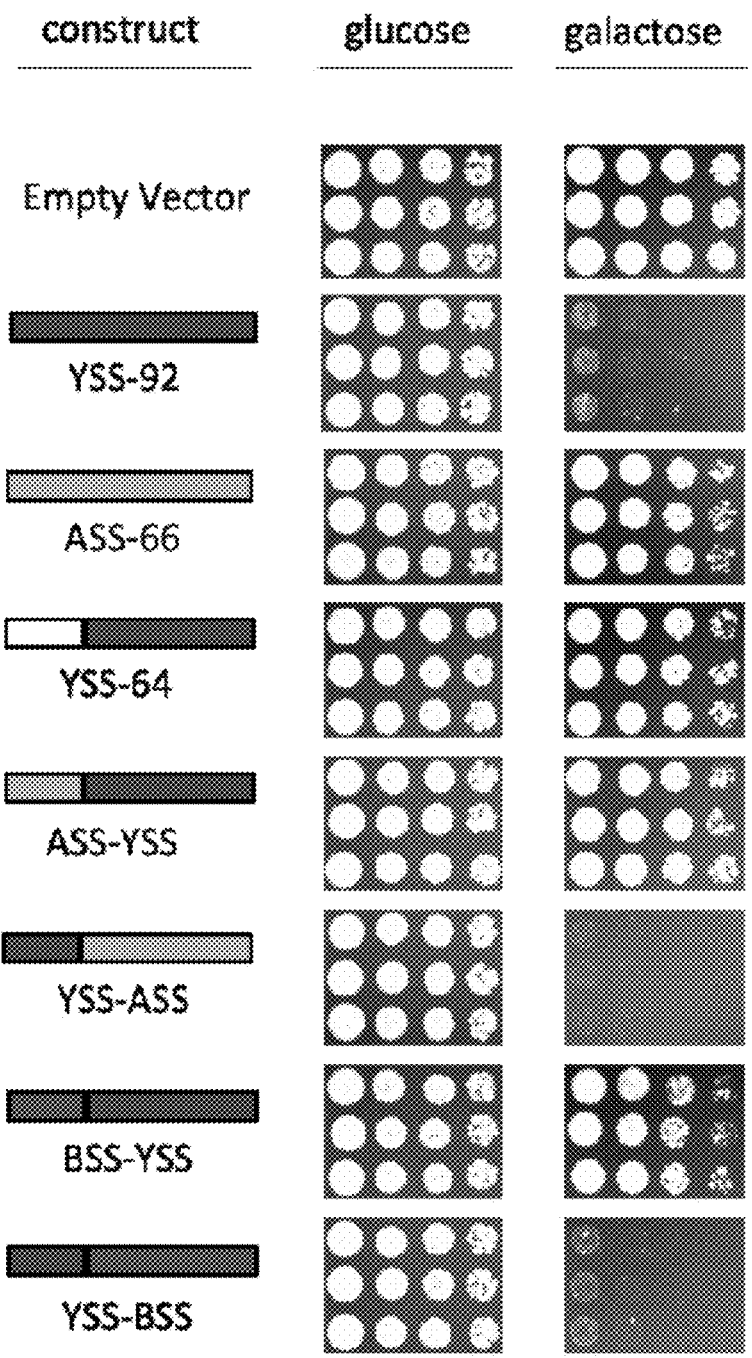
FIG. 7 shows the 26 amino acid stretch of YSS can inhibit the growth of yeast. Constructs were created in which the C-terminal 92 AA of YSS, the C-terminal 64 AA of YSS, the C-terminal 66 AA of ASS, the C-terminal 92 AA of YSS in which the 26 AA domain is replaced by the corresponding of ASS or BSS, and the C-terminus of either ASS or BSS in which the 26 AA domain is replaced by the corresponding of YSS were cloned into the pESC-Ura (Gal1 and Gal10 promoters) vector. Constructs were transformed into BY4741 yeast and positive transformants were grown in 2 mL of Yeast-Synthetic Drop-out medium for 4 days. Serial dilutions (Corresponding to O.D.600=0.5, 0.1, 0.02, and 0.004) were plated on selection media containing either glucose or galactose as the carbon source. Pictures were taken after 4 days growth at 28° C.

If the fungal 26 amino acid sequence was providing for specific and unique interactions between squalene synthase and some other factor(s), thus providing for prototrophic production of endogenous sterols, then over-expression of this peptide fragment might be expected to disrupt normal sterol metabolism and hence disrupt fungal growth. To test this possibility, a gene coding for the 92 carboxy terminal residues of the yeast squalene synthase was inserted into a galactose inducible expression vector and the recombinant vector introduced into a wild type yeast (BY4741) (FIG. 7). When grown on glucose, expression of the 92 carboxy-terminal squalene synthase gene was suppressed and the transformed yeast grew normally. However, when the same transformants were grown on galactose, growth was severely arrested. If a plant complementary carboxy-terminal gene was substituted for the yeast, no adverse effects were noted. When the 26 amino acid linker domain was deleted from the yeast gene construct, growth also was not impaired. When the deleted region was replaced with the correspond domain from a plant (ASS-YSS) or algae (BSS-YSS), growth also was unaffected. However, if the yeast 26 amino acid linker domain was substitute for the corresponding region of the plant (YSS-ASS) or algal (YSS-BSS) gene, then growth was abolished under conditions of induction of gene expression (plus galactose).

The 26 amino acid linker domain is unique to each kingdom, and hence represents a target for kingdom specific control of sterol metabolism.

Figure 8:
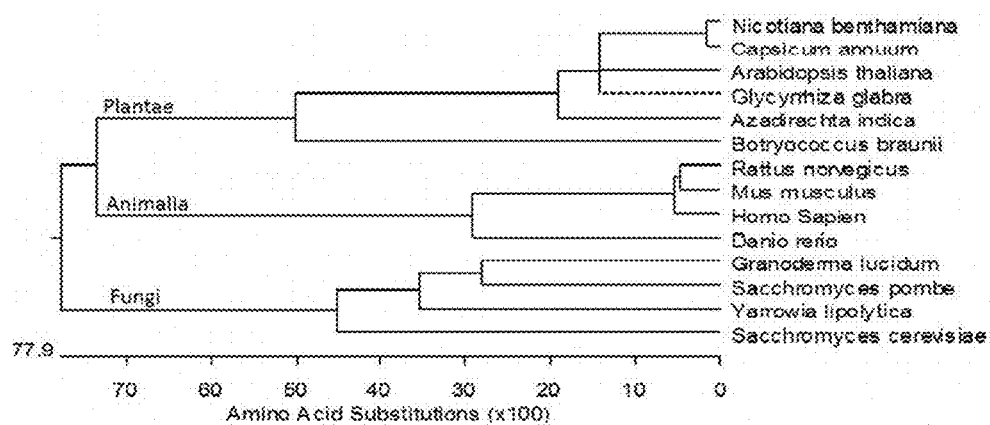
FIG. 8 shows a phylogenetic tree for the amino acid sequence alignment of the 26 amino acid linker domain of squalene synthases from diverse organisms. The clustering of the sequences for plants (Plantae), animals (Animalia) and fungi (Fungi) are indicative of the uniqueness of these domains to the respective organisms in each kingdom and the distinct functional significance of this domain for each kingdom as illustrated in FIGS. 4 and 7 above.

Attention to the 26 amino acid linker domain came about because of its unique conservation within fungal squalene synthases (FIG. 3). If this were to be a universal feature of squalene synthases, then one would expect this corresponding domain in plant and animal squalene synthases to be highly conserved within that kingdom of organisms, and distinctly different between kingdoms. FIG. 8 provides a phylogenetic assessment of this domain between the kingdoms of plants, animals and fungi and shows distinct clustering of these domains within squalene synthase genes to clades representing only organisms reflecting each of the kingdoms. Hence, one would expect that disruption of the 26 amino acid linker domain within mammalian cells to also disrupt cholesterol metabolism, much like we have observed for fungi.

Materials and Methods

The following disclosure provides background to the parameters and the experimental conditions used to generate the results discussed above.

Cloning the Various Squalene Synthases

Squalene synthases from *S. cerevisiae* (YSS), *B. braunii* (BSS), *R. norvegicus* (RSS), *N. benthamiana* (TSS), and *A. thaliana* (ASS) were cloned from original cell or tissue sources. First, total RNA was isolated from the respective species using the RNeasy Plant mini kit (Qiagen) or Trizol (Invitrogen, for *R. norvegicus* and *S. cerevisiae*) according to the manufacturer's recommendations, and first strand cDNA was synthesized using the SMARTer PCR cDNA synthesis kit (Clontech). The first strand cDNA was used as a template to amplify the various squalene synthase genes using the primer sets listed in Table 1 (restriction site in bold). YSS was cloned into the Yep352 vector with the AscI and XbaI sites, and a 3'-truncated form cloned into Yep352 and pET28a using the AscI and XbaI or BamHI and XhoI sites, respectively. BSS was cloned into Yep352 with the EcoRI and HindIII sites. RSS was cloned into YEp352 using the EcoRI and NotI sites and a 5'- and 3'-truncated RSS was cloned into pET28a using the BamHI and XhoI sites. TSS was cloned into Yep352 with the EcoRI and NotI sites. ASS was cloned into Yep352 with the EcoRI and NotI sites. All constructs were verified by automated DNA sequencing.

TABLE 1

Squalene Synthase Primer Sequences.

| gene | primer | Sequence | SEQ ID NO. |
|---|---|---|---|
| YSS | AscI For | AGGCGCGCCAAAACAATGGGAAAGCTATTACAATGGC | 37 |
|  | BamHI For | CGCGGATCCAAAACAATGGGAAAGCTATTACAATGGC | 38 |
|  | XbaI Rev | GCTCTAGATCACGCTCTGTGTAAAGTGTATAT | 39 |
|  | NotI Rev | ATAAGAATGCGGCCGCTCACGCTCTGTGTAAAGTG | 40 |
|  | XbaI Rev trunc | GCTCTAGATCACTTGTACTCTTCTTC | 41 |
|  | XhoI Rev trunc | GGGCTCGAGTCACTTGTACTCTTCTTC | 42 |
|  | NotI Rev trunc | ATAAGAATGCGGCCGCTCACTTGTACTCTTCTTCTTG | 43 |
| BSS | EcoRI For | CCGGAATTCAAAACAATGGGGATGCTTCGCTGGGGAGTGG | 44 |
|  | HindIII Rev | ATCCCAAGCTTTTAGGCGCTGAGTGTGGGTCTAGG | 45 |
|  | NotI Rev | ATAAGAATGCGGCCGCTTAGGCGCTGAGTGTGGGTCTAGG | 46 |
| RSS | EcoRI For | GGAATTCAAAACAATGGAGTTCGTGAAGTGTCTAGGCC | 47 |
|  | BamHI For trunc | CGCGGATCCATGGACCGGAACTCGCTCAGC | 48 |
|  | NotI Rev | ATAAGAATGCGGCCGCTCAGTGTTCTCTCTGGACATAGTC | 49 |
|  | XhoI Rev trunc | CCGCTCGAGTCAGCTCTGCGTCCTGATGTTGGAG | 50 |
| TSS | EcoRI For | GGAATTCATGGGGAGTTTGAGGGCTATTC | 51 |
|  | XbaI Rev | GCTCTAGACTAAGATCGGTTTCCGGATAGC | 52 |
|  | NotI Rev | ATAAGAATGCGGCCGCCTAAGATCGGTTTCCGGATAGC | 53 |
| ASS | EcoRI For | CCGGAATTCAAAACAATGGGGAGCTTGGGGACGATGCTG | 54 |
|  | XbaI Rev | GCTCTAGATCAGTTTGCTCTGAGATATGC | 55 |
|  | NotI Rev | ATAAGAATGCGGCCGCTCAGTTTGCTCTGAGATATGCAAAG | 56 |

Creating the BSS-YSS fusion

A reverse primer was designed to pair with the BSS EcoRI For (see Table 1), to amplify the first 352 codons of BSS except that a single nucleotide mutation was introduced into the 352$^{nd}$ codon to introduce a HindIII restriction site without changing the encoded amino acid (ATCCC AAGCTTCTCTGCTAATTTGAGG (SEQ ID NO: 57), HindIII site in bold, mutation underlined). This was cloned into the pET28a vector with the corresponding restriction sites, giving BSS$_{352}$-pET28a. Another primer was designed to pair with either primer, YSS NotI Rev or YSS NotI Rev trunc, to amplify YSS starting from codon 353 (ATCCAAGCTTAAATCTAAATTGGCTGTGC (SEQ ID NO: 58), HindIII site in bold), and these fragments cloned into BSS352-pET28a cut with HindIII and NotI to give the BSS-YSS and BSS-YSStr constructs. These were cut from the pET28a vector using EcoRI and NotI and ligated into the corresponding sites of Yep352. The construct was verified by automated DNA sequencing.

Creating the BSS-YSS-BSS Expression Cassette

A primer was designed to pair with primer, BSS EcoRI For, to amplify a fragment of the BSS-YSS construct with NgoMIV and NotI restriction sites (ATAAAGAATGCGGCCGCGAATGCCGGCTTCCATAAACTGTTCGATCTTGG (SEQ ID NO: 59), NgoMIV and NotI sites in bold). This was cloned into the EcoRI and NotI sites of YEp352, which was later cut with NgoMIV and NotI. Meanwhile a primer was designed to pair with primer, BSS NotI Rev, to amplify a 3' region of BSS except that two nucleotide mutations were introduced to add an NgoMIV restriction site without changing the encoded amino acids (GCAAAGAATGCCGGCCTGGCACGCACAAAAGATGACACC (SEQ ID NO: 60), NgoMIV site in bold, mutations underlined). This fragment was cloned into the NgoMIV and NotI sites of the cut Yep352 vector to give BSS-YSS-BSS. The construct was verified by automated DNA sequencing.

Creating Other Fusion Constructs

All other fusion constructs were created by employing an assembly PCR strategy as described by Niehaus et al. (11), using the primers listed in Tables 1 and 2. For example, YSS-BSS was created by using YSS as a template with the primer set, YSS-BSS 1R and YSS AscI For, to amplify a fragment of YSS with a 3' overhang, and using BSS as the template with the primer set, YSS-BSS IF and BSS HindIII Rev, to amplify a fragment of BSS with a 5' overhang. These two fragments were both used as templates in a PCR reaction with the primer set, YSS AscI For and BSS HindIII Rev, to give the YSS-BSS construct, which was cloned into the YEp352 vector with the corresponding restriction sites. YSS-BSS-YSS was created by using YSS-BSS and YSS as templates in the initial PCR reaction, and cloning the finished construct into YEp352 with the AscI and XbaI sites. All other constructs were created in a similar manner. TSS-YSS and YSS-TSS were cloned into YEp352 with the EcoRI and NotI, or AscI and XbaI restriction sites, respectively. YSS-ASS and ASS-YSS were cloned into YEp352 with AscI and XbaI, or EcoRI and XbaI restriction sites, respectively. All YSS M(a)-M(e) constructs were cloned into YEp352 with the AscI and XbaI restriction sites, and all ASS M(f)-M(j) constructs were cloned into YEp352 with EcoRI and XbaI restriction sites. All constructs were verified by automated DNA sequencing.

TABLE 2

Chimeric Squalene Synthase Primer Sequences.

| construct | direction | sequence | SEQ ID NO. |
|---|---|---|---|
| YSS-BSS | 1F | CTTACGTGATATCGAAGTCAGATGCAACACCGAGACCAGCGAGGATCCC | 61 |
| | 1R | GCATCTGACTTCGATATCACGTAAGTAATAGTCAAAAATCTCGACACGCC | 62 |
| YSS-ASS | 1F | CTTACGTGATATCAAGACAAAGGTTGACAAGAACGATCCAAATGCCAG | 63 |
| | 1R | CAACCTTTGTCTTGATATCACGTAAGTAATAGTCAAAAATCTCGACAC | 64 |
| ASS-YSS | 1F | CCTGCATGCTGAAATCTAAATTGGCTGTGCAAGATCCAAATTTCTTA | 65 |
| | 1R | GCCAATTTAGATTTCAGCATGCAGGAAAAATCATAGAAAGCACCATAG | 66 |
| YSS-TSS | 1F | CTTACGTGATATCAAATCCAAGGTTAATAATAATGATCCAAATGCAAC | 67 |
| | 1R | TTAACCTTGGATTTGATATCACGTAAGTAATAGTCAAAAATCTCGACAC | 68 |
| TSS-YSS | 1F | GACTTTTCTTGTATGCTGAAATCTAAATTGGCTGTGCAAGATCCAAATTTCTT | 69 |
| | 1R | GCCAATTTAGATTCAGCATACAAGAAAAGICAAAAAAAGCACCATATACATC | 70 |
| YSS-BSS-YSS | 1F | CAAAGCTGCCTGCAAGGAAATGTACCAGGATAAATTACCTCCTAACGTGAAGCC | 71 |
| | 1R | CCTGGTACATTTCCTTGCAGGCAGCTTTGATCTTATGCAGGTGTTCCAGAG | 72 |
| YSS-ASS-YSS | 1F | AAGACAAAGGTTGACAAGAACGATCCAAATGCCAGTAAGACACTAAACCGACTTGAAGCC | 73 |
| | 1R | TCTGCAGAGTTTCTGAACGGCTTCAAGTCGGTTTAGTGTCTTACTGGCATTTGGATCGTT | 74 |
| ASS-YSS-ASS | 1F | AAATCTAAATTGGCTGTGCAAGATCCAAATTICTTAAAATTGAACATTCAAATCTCCAAG | 75 |
| | 1R | TTCCATAAACTGTCGATCTGGAGATTTGAATGITCAATITTAAGAAATTGGATCTIG | 76 |
| YSS M(c) | 1F | CTCCGCCGTTCAAAAGTTTATGGAAGAAATGTACCAGGATAAATTACC | 77 |
| | 1R | CCATAAACTTTTGAACGGCGGAGATTTGAATGTTCAATTTTAAG | 78 |
| YSS M(d) | 1F | AATGCCAGTAAGACACTAAACCGTATCTCCAAGATCGAACAGTTTATGG | 79 |
| | 1R | GATACGGTTTAGTGTCTTACTGGCATTTGGATCTTGCACAGCCAATTTAG | 80 |
| YSS M(e) | 1F | GCCAGTAAGACACTAAACCGTCTTGAAGCCGTTCAGAAGTTTATGGAAGAAATGTACCAG | 81 |
| | 1R | CTTCTGAACGGCTTCAAGACGGTTTAGTGTCTTACTGGCATTTGGATCTTGCACAGCC | 82 |
| YSS M(a) | 1F | AAGACAAAGGTTGACAAGAACGATCCAAATGCCAGTAAGTTGAACATTCAAATCTCCAAG | 83 |
| | 1R | CTTACTGGCATTTGGATCGTTCTTGTCAACCTTTGTCTTGATATCACGTAAGTAATAGTC | 84 |
| YSS M(b) | 1F | ACACTAAACCGACTTGAAGCCGTTCAGAAACTCTGCAGAGAAATGTACCAGGATAAATTA | 85 |
| | 1R | TCTGCAGAGTTTCTGAACGGCTTCAAGTCGGTTTAGTGTTTTTAAGAAATTTGGATCTTG | 86 |
| ASS M(h) | 1F | CTTGAAAAAGATCGAACAGCTCTGCAGAGACGCTGGAGTTCTTC | 87 |
| | 1R | CAGAGCTGTTCGATCTTTTCAAGTCGGTTTAGTGTCTTACTGGC | 88 |
| ASS M(i) | 1F | AATTICTTAAAAATTGAACATTCAACTTGAAGCCGTICAGAAACTCTGCAG | 89 |
| | 1R | AAGTTGAATGTTCAATTTTAAGAAATTTGGATCGTTCTTGTCAACCTTTG | 90 |
| ASS M(j) | 1F | TICTTAAAAATTGAACATTCAAATCTCCAAGATCGAACAGCTCTGCAGAGACGCTGGAG | 91 |
| | 1R | CTGTTCGATCTTGGAGATTTGAATGTTCAATTTTAAGAAATTTGGATCGTTCTTGTCAAC | 92 |
| ASS M(f) | 1F | AAATCTAAATTGGCTGTGCAAGATCCAAATTICTTAAAAACACTAAACCGACTTGAAGCC | 93 |
| | 1R | TTTAAGAAATTGGATCTTGCACAGCCAATTTAGATTCAGCATGCAGGAAAAATCATA | 94 |
| ASS M(g) | 1F | TTGAACATTCAAATCTCCAAGATCGAACAGTTATGGAAGACGCTGGAGTICTCAAAAC | 95 |
| | 1R | TTCCATAAACTGTCGATCTGGAGATTTGAATGITCAACTTACTGGCATTGGATCGTT | 96 |

The Erg9 Complementation Assay

The Cali7-1 yeast line, which has an erg9 deletion so that it cannot synthesize sterols de novo and requires exogenous ergosterol for growth, was used for these purposes (10). The various squalene synthase constructs were transformed into Cali7-1 yeast using the lithium acetate method and plated on Yeast Synthetic Drop-out medium (selection media) lacking uracil and containing 5 mg/l ergosterol. Three independent CALI7-1 transformants of each construct were randomly selected and grown in 2 mL Yeast Synthetic Drop-out media (Sigma) containing 5 mg/L ergosterol at 28° C. for three days (OD600=6.0±0.3 after three days of growth), after which the culture was serially diluted with water to optical densities (600 nm) equal to 1, 0.2, 0.04, and 0.008, and 5 µL of each dilution spotted onto Yeast Synthetic Drop-out media plates without any exogenous ergosterol. Plates were incubated at 28° C. for 72 hours.

Liquid cultures of each transformant in TN-7 line were grown in 10 mL of Yeast Synthetic Drop-out media containing 5 mg/L ergosterol at room temperature for seven days. Organic extracts were prepared and analyzed by GC-MS for their squalene content. In brief, 1 mL aliquots of the culture were combined with 1 mL of acetone, vigorously mixed, and incubated at room temperature for 10 min. One mL of hexane was added and mixed vigorously for 60 sec. The mixture was then centrifuged briefly at 500×g to separate the phases, and an aliquot of the organic phase removed and 1-2 µL aliquots analyzed by GC-MS with a Varian CP-3800 GC coupled to a Varian Saturn 2200 MS/MS (Varian Medical Systems) using a Supelco SLB-5 ms fused silica capillary column (30 m×0.25 mm×0.25 µM film thickness, Supelco). Initial oven temperature was set at 220° C. for 1 min., ramped to 280° C. at 20° C./min., then ramped to 300° C. at 3° C./min.

The various SS constructs were expressed in Cali-7 yeast and grown for 3 days before 1.5 ml of culture was collected by centrifugation and stored at −80 C until further analysis. Yeast pellets were resuspended in 0.5 ml buffer (50 mM NaH2PO4, pH 7.8, 300 mM NaCl, 1 mM MgCl2, 1 mM PMSF, 1% glycerol (v/v)) then sonicated 3× for 5 sec with a microprobe sonicator at 60% maximum power. The samples were cooled on ice for 2 min between sonication treatments. The sonicate was centrifuged at 2,000 g for 10 min at 4° C. and the supernatant used in enzyme assays. Assays contained 50 mM Mops, pH 7.3, 20 mM MgCl2, 2.5 mM 2-mercaptoethanol, 10 µM [1-3H]-FPP (~1×105 dpm total), 2 mM NADPH, and 5 µL cell lysate in total reaction volume of 50 µL. Reactions were incubated at 37° C. for 1 h and then extracted with 100 µl n-hexane and an aliqout spotted on silica-TLC plates with a squalene standard. TLC was developed with n-hexane and the squalene zone was visualized with iodine vapor, scraped and analyzed by scintillation spectroscopy. The amount of total protein in the yeast supernatants was determined by Bradford Dye assays. Enzyme activity (pmole/h/µg total protein) is expressed as a percent of *S. cerevisiae* squalene synthase (YSS) enzyme activity. n=3.

Creation and Expression of Fluorescent Protein Tagged Constructs

An assembly PCR strategy (described above) was used to create constructs in which either efGFP or DsRed1 was fused to the amino terminus of various squalene synthase enzymes connected by a (GSGG)×2 peptide linker sequence. Primers used to create these constructs are listed in Table 3 (restriction sites, if any, in bold). For example, efGFP-YSS was created by using efGFP as a template with the primer set, efGFP AscI For and efGFP 1r, to amplify the efGFP coding sequence with a 3' overhanging linker sequence, and using YSS as the template with the primer set, efGFP-YSS if and YSS XbaI Rev, to amplify YSS with a 5' overhanging linker sequence. These two fragments were both used as templates in a PCR reaction with the primer set, efGFP AscI For and YSS XbaI Rev, to give the efGFP-YSS construct, which was cloned into YEp352 with the corresponding restriction sites. Similarly, efGFP-BYB was created by using efGFP as the template with the primer set, efGFP AscI For and efGFP 1r, and using BSS-YSS-BSS as the template with the primer set, efGFP-BSS if and BSS XbaI Rev, in the initial PCR reaction and cloning the assembled product into YEp352 with the AscI and XbaI sites. DsRed1-BSS was created using DsRed1 as the template with the primer set, DsRed1 XhoI For and DsRed1 1r, and using BSS as the template with the primer set, DsRed1-BSS if and BSS NotI Rev, in the initial PCR reaction and cloning the assembled product into pESC-leu with the XhoI and NotI sites. DsRed1-BSS was also cloned into the YEp352 vector by amplifying the sequence with the primer set, DsRed1 AscI For and BSS XbaI Rev, and cloning into the corresponding restriction sites. efGFP-YSStr was created by using efGFP-YSS as the template with the primer set, efGFP AscI For and YSStr XbaI Rev, and cloning the amplified product into the corresponding sites of YEp352. All constructs were verified by automated DNA sequencing. A CFP-tagged ER-marker (Pho86p) was kindly provided by Dr. Peter Nagy (12).

Various combinations of fluorescent-tagged squalene synthases or a CFP-tagged ER marker were transformed into Cali-7 yeast. Positive transformants were identified by PCR screening and grown in Yeast-synthetic Drop-out media containing 5 mg/L ergosterol for three days. Cells were collected by brief centrifugation at 500×g and applied to glass adhesion microscope slides. Confocal laser scanning micrographs were acquired on an Olympus FV1000 microscope (Olympus America Inc., Melville, N.Y.).

TABLE 3

Fluorescence protein tagged squalene synthase construct primers

| gene/construct | primer | sequence | SEQ ID NO |
|---|---|---|---|
| efGFP | AscI For | AGGCGCGCCAAAACAATGTCTAAAGGTGAAGAATTATTC | 97 |
| DsRed1 | XhoI For | CCGCTCGAGAAAACAATGGTGCGCTCCTCCAAGAACGTC | 98 |
| DsRed1 | AscI For | AGGCGCGCCAAAACAATGGTGCGCTCCTCCAAGAACGTC | 99 |
| efGFP | 1R | CATACCAGAACCACCACCAGAACCACCTTTGTACAATTCATCCATACCATGG | 100 |
| DsRed1 | 1R | CATACCAGAACCACCACCAGAACCACCCAGGAACAGGTGGTGGCGGCCC | 101 |
| efGFP-YSS | 1F | CAAAGGTGGTTCTGGTGGTGGTTCTGGTATGGGAAAGCTATTACAATTGGC | 102 |
| efGFP-BSS | 1F | CAAAGGTGGTTCTGGTGGTGGTTCTGGTATGGGGATGCTTCGCTGGGGAGTGG | 103 |
| DsRed1-BSS | 1F | CCTGGGTGGTTCTGGTGGTGGTTCTGGTATGGGGATGCTTCGCTGGGGAGTGG | 104 |

TABLE 3-continued

Fluorescence protein tagged squalene synthase construct primers

| gene/construct | primer | sequence | SEQ ID NO |
|---|---|---|---|
| YSS | XbaI Rev | GCTCTAGATCACGCTCTGTGTAAAGTGTATATA | 105 |
| YSStr | XbaI Rev | GCTCTAGATCACTTGTACTCTTCTTCTTGTTGGGTTGG | 106 |
| BSS | NotI Rev | ATAAGAATGCGGCCGCTTAGGCGCTGAGTGTGGGTCTAGG | 107 |
| BSS | XbaI Rev | GCTCTAGATTAGGCGCTGAGTGTGGGTCTAGG | 108 |

Creating C-Terminus Squalene Synthase Constructs

Constructs to be tested in *S. cerevisiae* were created using the pESC-Leu vector (Agilent) which harbors the Gal1/Gal10 divergent promoter to allow for galactose induction of gene expression. Primers used to create these constructs are listed in Table 4 (restriction sites, if any, in bold). YSS-92 was created by PCR amplifying a portion of the YSS gene corresponding to the 92 C-terminal amino acids using the primer sets, YSS-92 EcoRI For and YSS NotI Rev, and YSS-92 BamHI For and YSS HindIII Rev, and cloning into pESC-Leu with the corresponding restriction enzyme sites. ASS-66 and YSS-64 were created in the same manner. ASS-YSS and YSS-ASS were created in a similar manner using YSS-ASS-YSS or ASS-YSS-ASS as the templates for PCR, respectively. BSS-YSS and YSS-BSS were created by using YSS-BSS-YSS or BSS-YSS-BSS as the template for PCR, respectively. BSS-YSS was only cloned into pESC-Leu with the EcoRI and NotI restriction sites (Gal10 promotor) due to a native BamHI restriction site in the BSS-YSS coding sequence. All constructs were verified by automated DNA sequencing.

TABLE 4

Primers for creating C-terminus squalene synthase constructs

| primer | sequence | SEQ ID NOS |
|---|---|---|
| YSS-92 EcoRI For | GGAATTCAAAACAATGAAATCTAAATTGGCTGTGCAAGATCC | 109 |
| YSS-92 BamHI For | CGGGATCCAAAACAATGAAATCTAAATTGGCTGTGCAAGATCC | 110 |
| YSS-64 EcoRI For | GGAATTCAAAACAATGTACCAGGATAAATTACCTCC | 111 |
| YSS-64 BamHI For | CGGGATCCAAAACAATGTACCAGGATAAATTACCTCC | 112 |
| YSS NotI Rev | ATAAGAATGCGGCCGCTCACGCTCTGTGTAAAGTGTATATAT | 113 |
| YSS HindIII Rev | AACCCAAGCTTTCACGCTCTGTGTAAAGTGTATATAT | 114 |
| ASS-66 EcoRI For | GGAATTCAAAACAATGAAGACAAAGGTTGACAAGAACGATCC | 115 |
| ASS-66 BamHI For | CGGGATCCAAAACAATGAAGACAAAGGTTGACAAGAACGATCC | 116 |
| ASS NotI Rev | ATAAGAATGCGGCCGCTCAGTTTGCTCTGAGATATGCAAAGAC | 117 |
| ASS HindIII Rev | AACCCAAGCTTTCAGTTTGCTCTGAGATATGCAAAGAC | 118 |
| BSS-109 EcoRI For | GGAATTCAAAACAATGGAAGTCAGATGCAACACCGAGACC | 119 |
| BSS NotI Rev | ATAAGAATGCGGCCGCTTAGGCGCTGAGTGTGGGTCTAGG | 120 |
| BSS HindIII Rev | AACCCAAGCTTTTAGGCGCTGAGTGTGGGTCTAGG | 121 |

*Saccharomyces cerevisiae* Growth Inhibition Assays

Constructs were transformed into BY4741 yeast via the lithium acetate method and plated on Yeast-Synthetic Dropout medium plates lacking uracil. Positive transformants were verified by PCR screening and grown in 2 mL of Yeast-Synthetic Drop-out medium for 4 days ($OD_{600}=9.0\pm0.1$ after 4 days growth). Cultures were serial diluted with water to optical densities (600 nm) equal to 0.5, 0.1, 0.02, and 0.004, and 5 µL of each dilution was spotted on selection media containing either 2% glucose or 2% galactose as the carbon source. Pictures were taken after 4 days growth at 28° C.

The following Table 5 provides a cross reference for this disclosure.

TABLE 5

| New Name | Name on tube |
|---|---|
| YSS-ASS-YSS | YSS-M(f) |
| ASS-YSS-ASS | ASS-M(f) |
| YSS-Ma | YSS-Md |
| YSS-Mb | YSS-Me |
| YSS-Mc | YSS-Ma |
| YSS-Md | YSS-Mb |
| YSS-Me | YSS-Mc |
| ASS-Mf | ASS-Md |
| ASS-Mg | ASS-Me |
| ASS-Mh | ASS-Ma |
| ASS-Mi | ASS-Mb |
| ASS-Mj | ASS-Mc |

It will be understood that various details of the presently disclosed subject matter can be departed from the scope of the subject matter disclosed herein. Furthermore, the foregoing, description is for purposes of illustration only, and not for the purpose of limitation.

REFERENCES

Various references have been cited throughout this disclosure and include ones listed below. All are herein incorporated by reference.

1. Fegueur M, Richard L, Charles A D, Karst F (1991) Isolation and primary structure of the ERG9 gene of *Saccharomyces cerevisiae* encoding squalene synthetase. Current Genetics 20(5), 365-72
2. Jennings S M, Tsay Y H, Fisch T M, Robinson G W (1991) Molecular cloning and characterization of the yeast gene for squalene synthetase. Proceedings of the National Academy of Sciences of the United States of America 88(14), 6038-42
3. Robinson G W, Tsay Y H, Kienzle B K, Smithmonroy C A, Bishop R W (1993) Conservation between human and fungal squalene synthetases—similarities in structure, function, and regulation. Mol Cell Biol 13:2706-2717.
4. Soltis D A, et al. Expression, purification, and characterization of the human squalene synthase: use of yeast and baculoviral systems. Archives of Biochemistry and Biophysics 316(2), 713-23
5. Nakashima T, Inoue T, Oka A, Nishino T, Osumi T, Hata S, (1995) Cloning, expression, and characterization of cDNAs encoding *Arabidopsis thaliana* squalene synthase. Proceedings of the National Academy of Sciences of the United States of America 92(6), 2328-32
6. Hanley K et al. (1996) Molecular cloning, in vitro expression and characterization of a plant squalene synthetase cDNA. Plant Molecular Biology 30(6), 1139-1151
7. Kribii R A et al. (1997) Cloning and characterization of the *Arabidopsis thaliana* SQS1 gene encoding squalene synthase. Involvement of the C-terminal region of the enzyme in the channeling of squalene through the sterol pathway. European Journal of Biochemistry 249(1), 61-69
8. Merkulov S et al. (2000) Cloning and characterization of the *Yarrowia lipolytica* squalene synthase (SQS1) gene and functional complementation of the *Saccharomyces cerevisiae* erg9 mutation. Yeast 16(3), 197-206
9. Busquets A et al. (2008) *Arabidopsis thaliana* contains a single gene encoding squalene synthase. Plant Molecular Biology 67(1-2), 25-36
10. Song L S (2003) Detection of farnesyl diphosphate accumulation in yeast erg9 mutants. Anal Biochem 317: 180-185.
11. Niehaus T D, et al. (2011) Identification of Unique Mechanisms for Triterpene Biosynthesis in *B. braunii*. Proc Natl Acad Sci USA 108(30), 12260-12265.
12. Panavas T, et al. (2005) The role of the p33:p33/p92 interaction domain in RNA replication and intracellular localization of p33 and p92 proteins of Cucumber necrosis tombusvirus. Virology. 338(1):81-95.

The invention claimed is:

1. A compound consisting of an amino acid sequence selected from the group consisting of SEQ ID NOs: 1-12 and 161, wherein the compound inhibits fungal growth.

2. The compound of claim 1, wherein the amino acid sequence is SEQ ID NO: 1.

3. The compound of claim 1, wherein the amino acid sequence is selected from the group consisting of SEQ ID NOs: 2-12.

* * * * *